US012715905B2

(12) United States Patent
Conroy et al.

(10) Patent No.: US 12,715,905 B2
(45) Date of Patent: Aug. 25, 2026

(54) METHODS OF CHARACTERIZING AND PURIFYING VEGF RECEPTOR FUSION PROTEIN

(71) Applicant: Regeneron Pharmaceuticals, Inc., Tarrytown, NY (US)

(72) Inventors: Paul Conroy, Blackford (IE); John Crowley, Castletroy (IE); Marguerita McCarthy, Ballinacurra (IE); Kathleen O'Dwyer, Boher (IE); Shunhai Wang, Scarsdale, NY (US); Sisi Zhang, White Plains, NY (US); Yuetian Yan, Chappaqua, NY (US); Tyler Greer, Elmsford, NY (US); Siobhan Hogan, Raheen (IE); Xiaojing Zheng, Gaithersburg, MD (US); Hui Xiao, Ridgewood, NJ (US); Ning Li, New Canaan, CT (US); Lili Guo, Riverside, CT (US); Yuan Mao, Hartsdale, NY (US); Prerana Mantri, New Rochelle, NY (US); Evan Koufos, Emerson, NJ (US); Kathir Muthusamy, Cheshire, CT (US); Nisha Palackal, White Plains, NY (US); Erica Pyles, New City, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 19/320,739

(22) Filed: Sep. 5, 2025

(65) Prior Publication Data

US 2026/0001935 A1 Jan. 1, 2026

Related U.S. Application Data

(63) Continuation of application No. 18/988,309, filed on Dec. 19, 2024.

(Continued)

(51) Int. Cl.
*C07K 14/71* (2006.01)
*B01D 15/34* (2006.01)
(Continued)

(52) U.S. Cl.
CPC .............. *C07K 14/71* (2013.01); *B01D 15/34* (2013.01); *C07K 1/16* (2013.01); *C12Q 1/37* (2013.01);
(Continued)

(58) Field of Classification Search
CPC ...... C07K 14/71; C07K 1/16; C07K 2317/30; B01D 15/34; C12Q 1/37; G01N 2333/96416
See application file for complete search history.

(56) References Cited

U.S. PATENT DOCUMENTS 5,721,121 A 2/1998 Etcheverry et al.
5,952,199 A 9/1999 Davis-Smyth et al.
(Continued)

FOREIGN PATENT DOCUMENTS

WO 0192337 A2 12/2001
WO 2007077217 A2 7/2007
(Continued)

OTHER PUBLICATIONS

Bee et al., Trace levels of the CHO host cell protease cathepsin D caused particle formation in a monoclonal antibody product, 2015, Biotechnol. Prog. 31(5):1360-1369 (Year: 2015).*
(Continued)

*Primary Examiner* — Robert B Mondesi
*Assistant Examiner* — Naghmeh Nina Moazzami
(74) *Attorney, Agent, or Firm* — BakerHostetler

(57) ABSTRACT

Anti-VEGF proteins including the VEGF trap protein aflibercept can be produced to have a low level of an aspartyl protease (e.g., a low level of cathepsin D), such as less than 1 ppm of the aspartyl protease.

30 Claims, 37 Drawing Sheets

Specification includes a Sequence Listing.

Related U.S. Application Data

(60) Provisional application No. 63/612,573, filed on Dec. 20, 2023.

(51) Int. Cl.
*C07K 1/16* (2006.01)
*C12Q 1/37* (2006.01)

(52) U.S. Cl.
CPC .................... *C07K 2317/30* (2013.01); *G01N 2333/96416* (2013.01)

(56) References Cited

U.S. PATENT DOCUMENTS

| | | | | |
|---|---|---|---|---|
| 6,100,071 | A | 8/2000 | Davis-Smyth et al. | |
| 6,171,825 | B1 | 1/2001 | Chan et al. | |
| 6,383,486 | B1 | 5/2002 | Davis-Smyth et al. | |
| 6,897,294 | B2 | 5/2005 | Davis-Smyth et al. | |
| 7,070,959 | B1 | 7/2006 | Papadopoulos et al. | |
| 7,279,159 | B2 | 10/2007 | Daly et al. | |
| 7,306,799 | B2 | 12/2007 | Wiegand et al. | |
| 7,374,757 | B2 | 5/2008 | Papadopoulos et al. | |
| 7,374,758 | B2 | 5/2008 | Papadopoulos et al. | |
| 7,531,173 | B2 | 5/2009 | Wiegand et al. | |
| 7,608,261 | B2 | 10/2009 | Furfine et al. | |
| 7,771,721 | B2 | 8/2010 | Davis-Smyth et al. | |
| 8,936,441 | B2 | 1/2015 | McKeever et al. | |
| 11,535,663 | B2 * | 12/2022 | Lawrence | C12P 21/06 |
| 2007/0212770 | A1 | 9/2007 | Grillberger et al. | |
| 2008/0009040 | A1 | 1/2008 | Grillberger et al. | |
| 2022/0074950 | A1 | 3/2022 | Nie et al. | |
| 2023/0063116 | A1 | 3/2023 | Martin et al. | |
| 2024/0417442 | A1 | 12/2024 | Luo et al. | |

FOREIGN PATENT DOCUMENTS

| | | | |
|---|---|---|---|
| WO | 2018094316 | A1 | 5/2018 |
| WO | 2020201519 | A1 | 10/2020 |

OTHER PUBLICATIONS

Cui et al., Cathepsin D: Removal strategy on protein A chromatography, near real time monitoring and characterisation during monoclonal antibody production, Journal of Biotechnology, 305: 51-60, 2019. https://doi.org/10.1016/j.jbiotec.2019.08.013.

Hu et al., Sodium caprylate wash during Protein A chromoatography as an effective means for removing proteas(s) responsible for target antibody fragmentation, Protein Expression and Purification, 186 (105907): 1-5, 2021. https://doi.org/10.1016/j.pep.2021.105907.

Hutchinson et al., Improved clearance of host cell protein impurities at the polishing purification step using multimodal chromatography, Journal of Chromoatography A, 1732 (465229): 1-9, 2024. https://doi.org/10.1016/j.chroma.2024.465229.

Arshady et al., Suspension polymerisation and its application to the preparation of polymer supports, Reactive Polymers, Ion Exchangers, Sorbents, 1(3): 159-174, Aug. 1983, https://doi.org/10.1016/0167-6989(83)90015-6.

Babcock et al., Partial Replacement of Chemically Defined Media with Plant-Derived Protein Hydrolysates, BioPharm International, 2010 Supplement (5): 16 pages, https://www.biopharminternational.com/view/partial-replacement-chemically-defined-media-plant-derived-protein-hydrolysates.

Briozzo et al., In Vitro Degradation of Extracellular Matrix with Mr 52,000 Cathepsin D Secreted by Breast Cancer Cells, Cancer Research, 48: 3688-3692, Jul. 1988.

Graham et al., Characteristics of a Human Cell Line Transformed by DNA from Human Adenovirus Type 5, Journal of General Virology 36(1 ), 1977, https://doi.org/10.1099/0022-1317-36-1-59.

Hjerten, Stellan, The preparation of agarose spheres for chromatography of molecules and particles, Biochimica et Biophysica Acta (BBA)—Specialized Section on Biophysical Subjects, 79(2): 393-398, Mar. 1964, https://doi.org/10.1016/0926-6577(64)90020-8.

International Search Report and Written Opinion for International Application No. PCT/US2024/061078, mailed Mar. 31, 2025, 13 pages.

Jones et al., "High-risk" host cell proteins (HCPs): A multi-company collaborative view, Biotechnol Bioeng., 118: 2870-2885, 2021, DOI: 10.1002/bit.27808.

Kolhekar et al., Peptidylglycine a-Hydroxylating Monooxygenase: Active Site Residues, Disulfide Linkages, and a Two-Domain Model of the Catalytic Core, Biochemistry 36(36): 10901-10909, Sep. 1997, https://doi.org/10.1021/bi97087 47.

Mather et al., Culture of Testicular Cells in Hormone-Supplemented Serum-Free Medium, Annals of the New York Academy of Sciences, 383(1 ): 44-68, Jun. 1982, https://doi.org/10.1111/j.17 49-6632.1982.tb23161.x.

Matfier, Jennie P., Establishment and Characterization of Two Distinct Mouse Testicular Epithelial Cell Line, Biology of Reproduction 23(1 ): 243-252, Aug. 1980, https://doi.org/10.1095/biolreprod23.1.243.

O'Brien Johnson et al., Combination of FAIMS, Protein A Depletion, and Native Digest Conditions Enables Deep Proteomic Profiling of Host Cell Proteins in Monoclonal Antibodies, Anal Chem., 92(15): 10478-10484, Aug. 2020, 10.1021/acs.analchem.Oc01175.

Urlub et al., Effect of gamma rays at the dihydrofolate reductase locus: Deletions and inversions, Somatic Cell and Molecular Genetics 12: 555-566, 1986, https://doi.org/10.1007/BF01671941.

Urlaub et al., Isolation of Chinese hamster cell mutants deficient in dihydrofolate reductase activity, Proc. Natl. Acad. Sci. USA 77(7): 4216-4220, Jul. 1980, https://doi.org/10.1073/pnas.77. 7.4216.

Written Opinion for Patent Application No. PCT/US2024/061078 dated Jan. 20, 2026.

United States Pharmacopeia, General Chapter 1132, Residual Host Cell Protein Measurement in Biopharmaceuticals, USP 39-NF 34 (2016) 1416-1436.

* cited by examiner

FIG. 3

FIG. 4
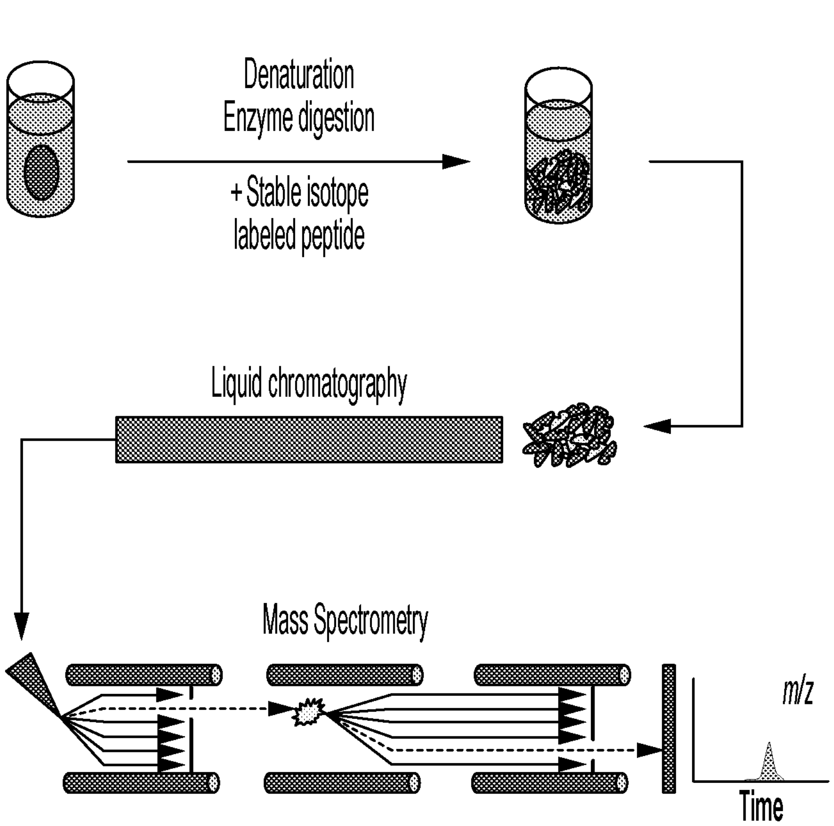
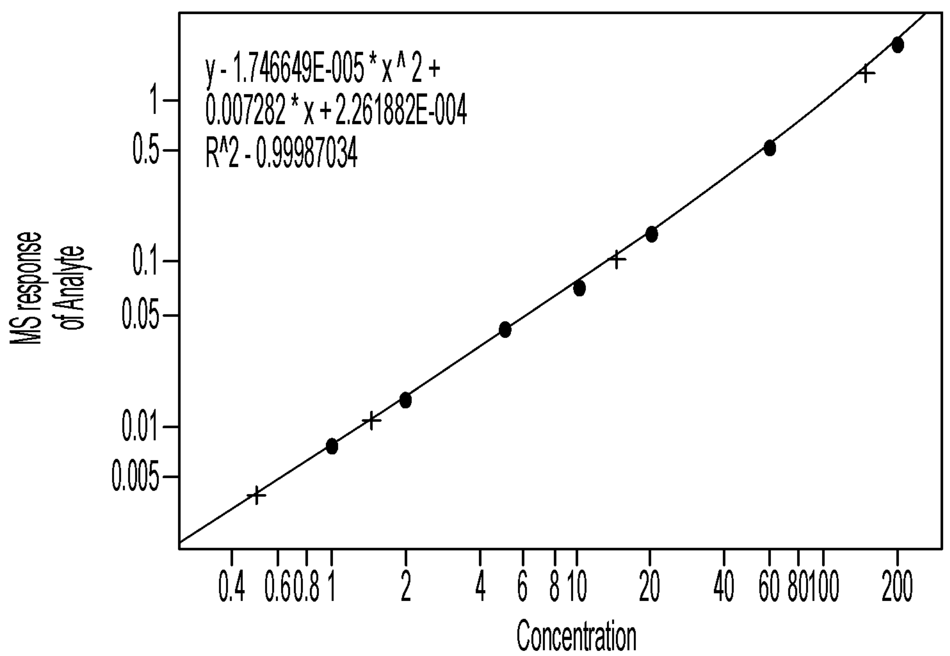

FIG. 5

| Method | LC-MRM-MS absolute quantitation |
|---|---|
| Targets | Cathepsin D |
| Matrix | VEGF Trap |
| Processing | Direct enzymatic digestion with Lys-C under non-reduced condition |
| Sample consumption | 50 μg of protein |
| Dynamic range | 0.5 – 200 ppm (1 ppm = 1 ng HCP / mg drug) |
| QC | LLOQ: 0.5 ppm, LQC: 1.5 ppm, MQC: 15 ppm, HQC: 150 ppm |
| Instrument time | 32 min per sample |

LC-MRM-MS (Liquid Chromatography-Multiple Reaction Monitoring-Mass Spectrometry)

FIG. 6

| Lot Number | Material Full Name | Site | Cathepsin D concentration-duplicate 1 (ppm) | Cathepsin D concentration-duplicate 2 (ppm) | Average Cathepsin D concentration (ppm) * |
|---|---|---|---|---|---|
| I | VEGF Trap DSI | A | 1.46 | 1.38 | 1.42 |
| II | VEGF Trap DSI | A | 1.18 | 1.23 | 1.21 |
| III | VEGF Trap DSI | A | 1.48 | 1.47 | 1.47 |
| I | VEGF Trap DSI | B | 0.82 | 0.85 | 0.84 |
| II | VEGF Trap DSI | B | 1.00 | 1.08 | 1.04 |
| III | VEGF Trap DSI | B | 0.87 | 0.86 | 0.86 |
| IV | VEGF Trap DS | A | BLLQ | BLLQ | BLLQ |
| V | VEGF Trap DS | A | BLLQ | BLLQ | BLLQ |
| VI | VEGF Trap DS | A | BLLQ | BLLQ | BLLQ |
| VII | VEGF Trap DS | A | BLLQ | BLLQ | BLLQ |
| IV | VEGF Trap DS | B | BLLQ | BLLQ | BLLQ |
| V | VEGF Trap DS | B | BLLQ | BLLQ | BLLQ |
| VI | VEGF Trap DS | B | BLLQ | BLLQ | BLLQ |

* Levels were calculated as the mean of the duplicate measurements.

| Low asymptote | Slope | EC50 (ng/mL) | High asymptote | R2 |
|---|---|---|---|---|
| 0.173 | 1.02 | 11.7 | 10.7 | 1 |

Cathepsin D (ng/mL)

35
30
25
20
15
10
5
0

Cathepsin D (PPM)

4.5
4
3.5
3
2.5
2
1.5
1
0.5
0

Depth Filtrate
AEX
HIC ng/mL
PPM

FIG. 11
1. Cathpesin-D Affinity Column
- Binds antibodies targeting the HCP, all other antibodies and proteins flow through
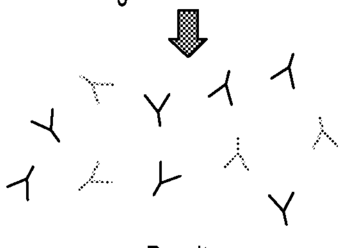
Result:
Anti-cathepsin D + Anti-MMH
2. Affinity Column for mmh tag antibodies
- Binds anti-mmh tag antibodies
- Anti-cathepsin D antibodies flow through
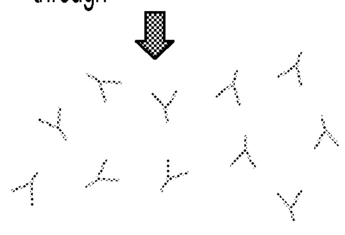
Result:
Anti-cathepsin D (A)
Intact VEGF-Trap
NR1
VEGFR1
VEGFR2
IgG1-FC (B)
Cathepsin D Site
K T N Y L T H R Q T N T
89 90 91 92 93 94 95 96 97 98 99 100
chemical cleavage sites
VEGF-Trap & Cathepsin D
NR1

NR1 %
18
16
14
12
10
8
6
4
2
0
Y92/L93
Y92/L93
Y92/L93
Y92/L93
Replicate 1, 2 & 3
Replicate 1, 2 & 3
D103/V104
N99/T100
Y92L93
N91Y92
T90/N91

FIG. 21
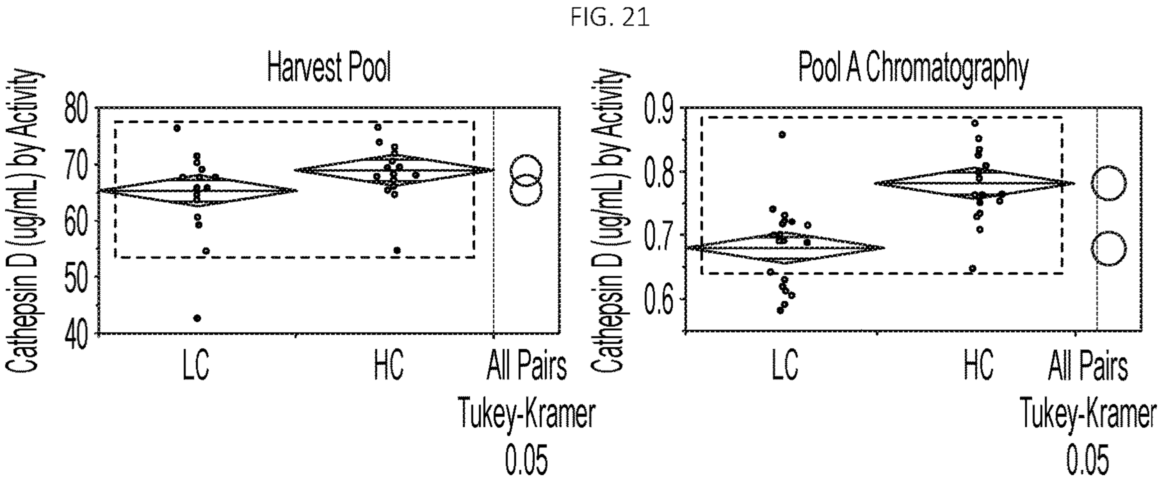
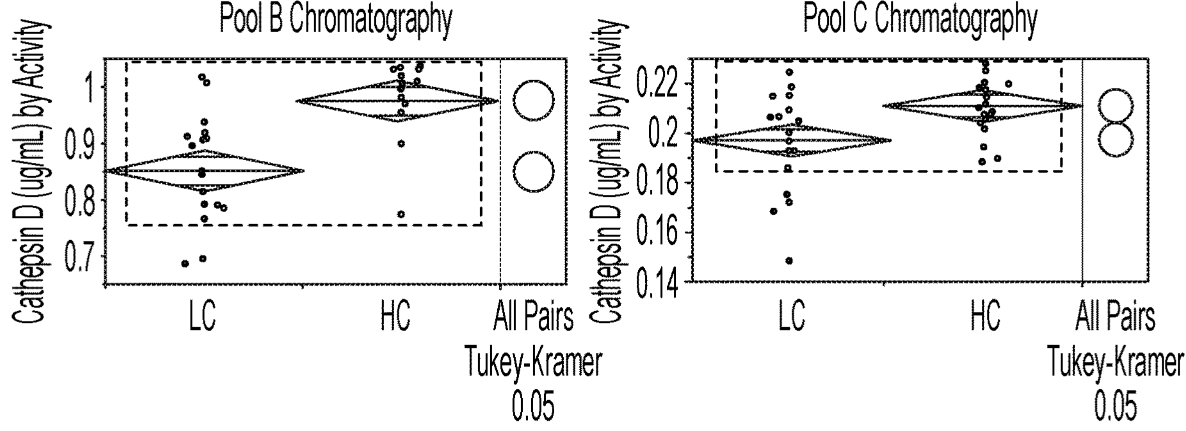
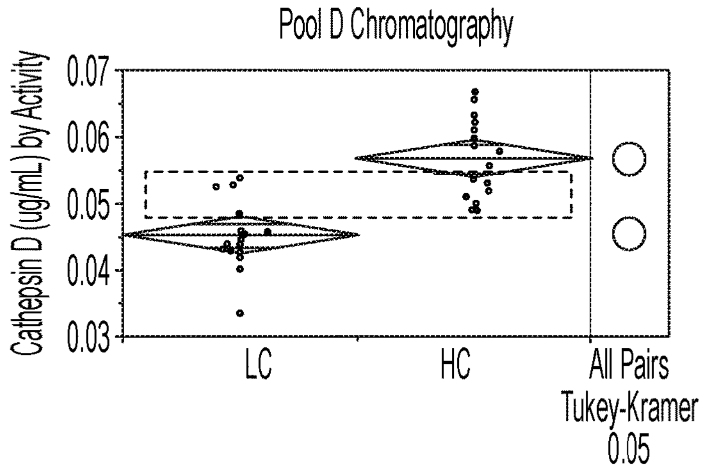

= High Efficiency Column
= Low Efficiency Column
Absorbance (mAu)
mAU
Volume (mL)
Cathepsin D Concentration (ppm)
Collection START
Collection END
2.B.2
2.B.3
2.B.4
2.B.5
2.C.1
2.C.2
2.C.3
2.C.4
2.C.5
3.A.1
3.A.2
3.A.3
3.A.4
3.A.5
3.B.1
3.B.2
3.B.3
3.B.4
3.B.5
3.C.1
3.C.2
3.C.3
3.C.4
3.C.5
4.A.1
4.A.2
4.A.3
4.A.4
4.A.5
4.B.1
4.B.2
4.B.3

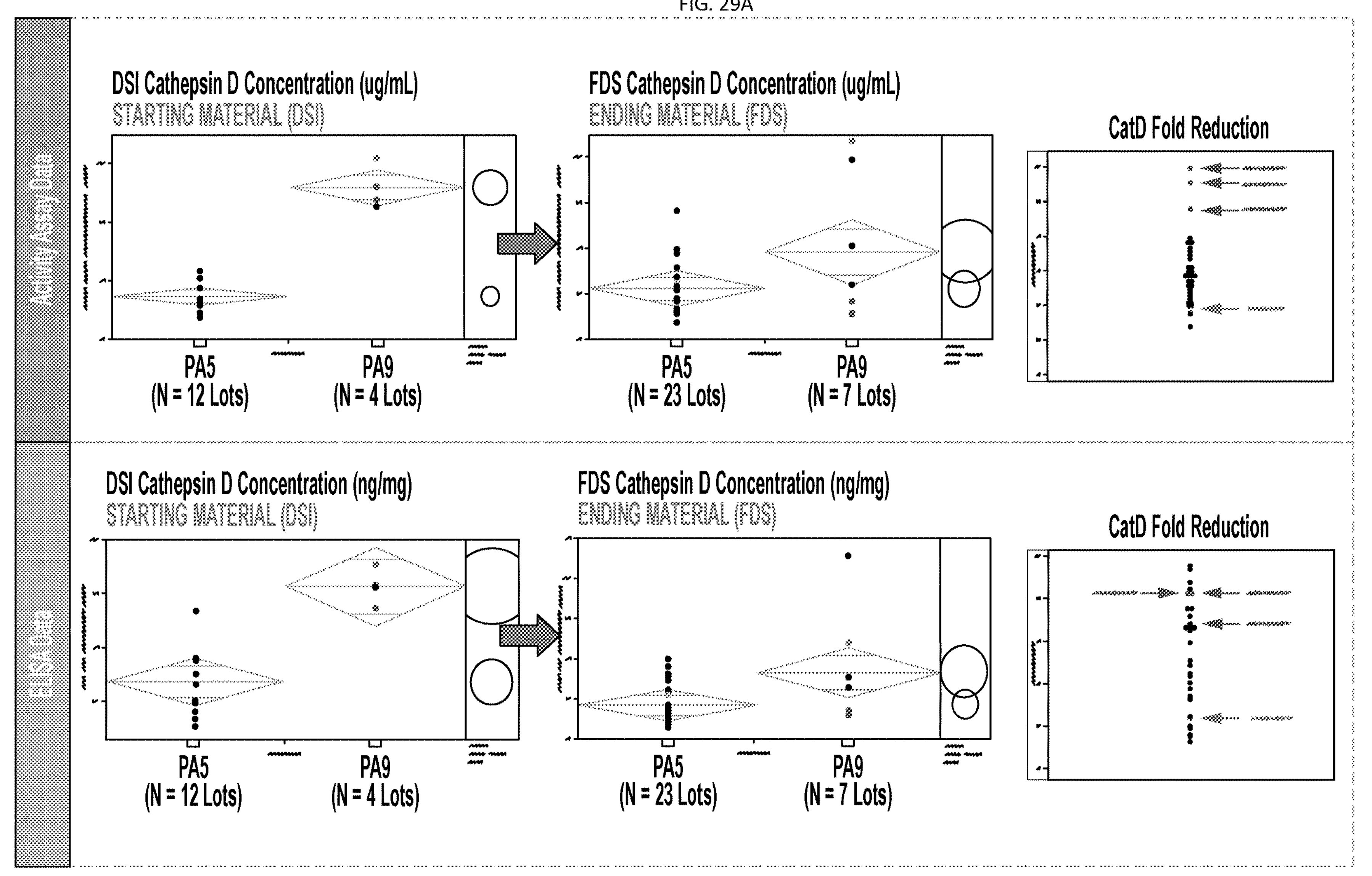
FIG. 29A
Activity Assay Data
DSI Cathepsin D Concentration (ug/mL)
STARTING MATERIAL (DSI)
PA5
(N = 12 Lots)
PA9
(N = 4 Lots)
FDS Cathepsin D Concentration (ug/mL)
ENDING MATERIAL (FDS)
PA5
(N = 23 Lots)
PA9
(N = 7 Lots)
CatD Fold Reduction
ELISA Data
DSI Cathepsin D Concentration (ng/mg)
STARTING MATERIAL (DSI)
PA5
(N = 12 Lots)
PA9
(N = 4 Lots)
FDS Cathepsin D Concentration (ng/mg)
ENDING MATERIAL (FDS)
PA5
(N = 23 Lots)
PA9
(N = 7 Lots)
CatD Fold Reduction FIG. 30A
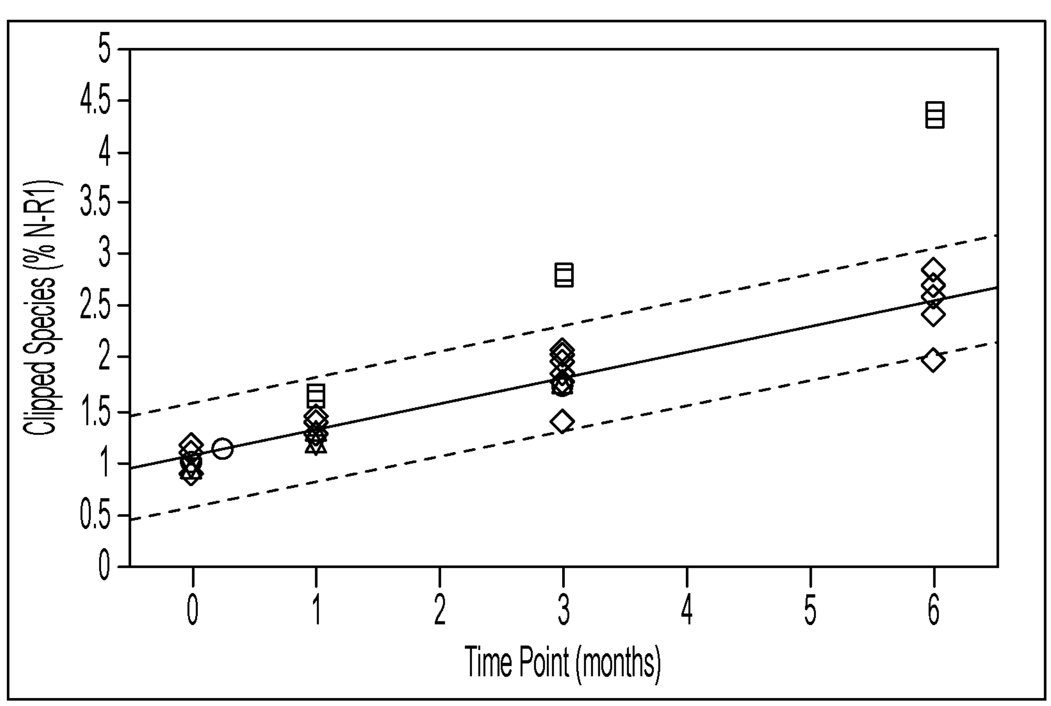
FIG. 30B
Clipped Species Formation at 25°C
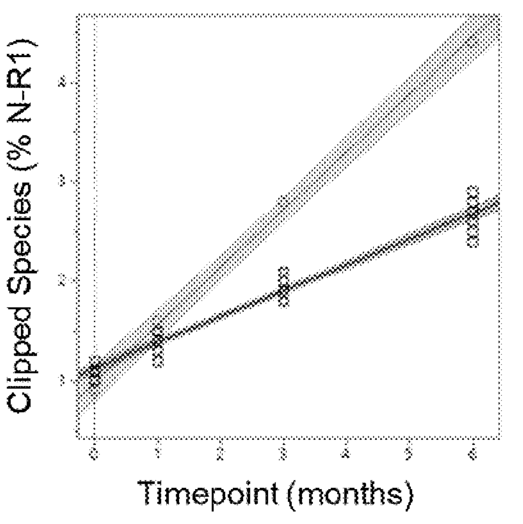
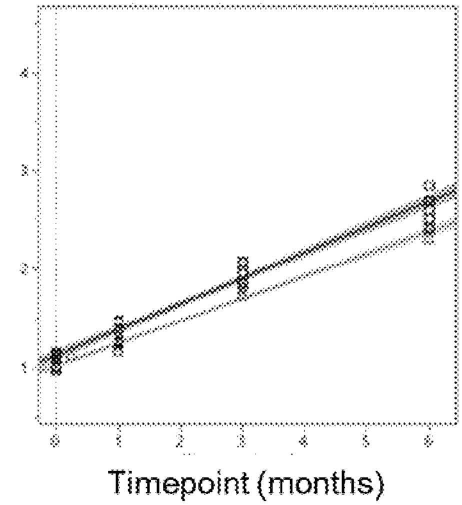
Red: Pre-optimisation,
Green: Post Optimisation,
Black: Comparators

| Assay | Description | R2 | Assay Variability at DS |
|---|---|---|---|
| ELISA | Total Content | 0.59 | 17.1% n=8 (AV) to 30% (SOP) |
| Activity | Activity | 0.63 | 6% n=6 (TD - within a run) |
| MS | Total Content | 0.63 | NA |

Mean CathD Level

Low Cat D

High Cat D

| Fold Change relative to Mean | 0.6× | 0.8× | | 1.2× | 1.4× | 2.3× | 4.3× | 6.0× |
|---|---|---|---|---|---|---|---|---|
| Cat D Conc. (ppm) | 0.02 | 0.04 | 0.053 | 0.06 | 0.07 | 0.12 | 0.23 | 0.32 |

SEQUENCE LISTING

```
Sequence total quantity: 2
SEQ ID NO: 1            moltype = AA  length = 432
FEATURE                 Location/Qualifiers
source                  1..432
                        mol_type = protein
                        organism = synthetic construct
SEQUENCE: 1
SDTGRPFVEM YSEIPEIIHM TEGRELVIPC RVTSPNITVT LKKFPLDTLI PDGKRIIWDS  60
RKGFIISNAT YKEIGLLTCE ATVNGHLYKT NYLTHRQTNT IIDVVLSPSH GIELSVGEKL  120
VLNCTARTEL NVGIDFNWEY PSSKHQHKKL VNRDLKTQSG SEMKKFLSTL TIDGVTRSDQ  180
GLYTCAASSG LMTKKNSTFV RVHEKDKTHT CPPCPAPELL GGPSVFLFPP KPKDTLMISR  240
TPEVTCVVVD VSHEDPEVKF NWYVDGVEVH NAKTKPREEQ YNSTYRVVSV LTVLHQDWLN  300
GKEYKCKVSN KALPAPIEKT ISKAKGQPRE PQVYTLPPSR DELTKNQVSL TCLVKGFYPS  360
DIAVEWESNG QPENNYKTTP PVLDSDGSFF LYSKLTVDKS RWQQGNVFSC SVMHEALHNH  420
YTQKSLSLSP GK                                                     432

SEQ ID NO: 2            moltype = AA  length = 418
FEATURE                 Location/Qualifiers
source                  1..418
                        mol_type = protein
                        organism = synthetic construct
SEQUENCE: 2
SAVIRIPLRK FTSIRRTMTE VGGSVEDLIL KGPITKYSNQ SPAETKGPVS ELLKNYLDAQ  60
YYGEIGIGTP PQCFTVVFDT GSSNLWVPSI HCKLLDIACW IHHKYNSGKS STFVKNGTSF  120
DIHYGSGSLS GYLSQDTVSV PCKSEQPGGL KVEKQIFGEA IKQPGITFIA AKFDGILGMG  180
YPSISVNNVV PVFDNLMQQK LVEKNIFSFF LNRDPTGQPG GELMLGGIDS KYYEGELSYL  240
```

-continued

```
NVTRKAYWQV HMDQLDVANG LTLCKGGCEA IVDTGTSLLV GPVDEVKELQ KAIGAVPLIQ  300
GEYMIPCEKV SSLPSVTLKL GGKDYELSPS KYVLKVSQGG KTICLSGFMG MDIPPPSGPL  360
WILGDVFIGT YYTVFDRDNN RVGFAKAATL EQKLISEEDL GGEQKLISEE DLHHHHHH    418
```

METHODS OF CHARACTERIZING AND PURIFYING VEGF RECEPTOR FUSION PROTEIN

CROSS REFERENCE TO RELATED APPLICATION

The present application is a continuation of U.S. application Ser. No. 18/988,309, filed Dec. 19, 2024, titled "METHODS OF CHARACTERIZING AND PURIFYING VEGF RECEPTOR FUSION PROTEIN", which claims priority to and the benefit of U.S. patent application No. 63/612,573, "AFLIBERCEPT, TRUNCATED FORM OF AFLIBERCEPT AND METHODS OF CHARACTERIZING AND PURIFYING THEREOF," which was filed on Dec. 20, 2023, the disclosures of both of which are hereby incorporated by reference in its entirety.

SEQUENCE LISTING

The instant application contains a Sequence Listing which is being submitted herewith electronically in XML format and is hereby incorporated by reference in its entirety. Said XML copy, created on Dec. 19, 2024, is named 086939-501101-REGN11448US02_Sequencelisting.xml and is 4 kilobytes in size.

FIELD

The present disclosure generally pertains to methods for producing and purifying VEGF receptor fusion proteins including aflibercept.

BACKGROUND

Persistent angiogenesis may cause or exacerbate certain diseases such as psoriasis, rheumatoid arthritis, hemangiomas, angiofibromas, diabetic retinopathy and neovascular glaucoma. An inhibitor of VEGF activity can be useful as a treatment for such diseases and other VEGF-induced pathological angiogenesis and vascular permeability conditions, such as tumor vascularization. The angiopoietins and members of the vascular endothelial growth factor (VEGF) family are the only growth factors thought to be largely specific for vascular endothelial cells.

Several eye disorders are associated with pathological angiogenesis. For example, the development of age-related macular degeneration (AMD) is associated with a process called choroidal neovascularization (CNV). Leakage from the CNV causes macular edema and collection of fluid beneath the macula resulting in vision loss. Diabetic macular edema (DME) is another eye disorder with an angiogenic component. DME is the most prevalent cause of moderate vision loss in patients with diabetes and is a common complication of diabetic retinopathy, a disease affecting the blood vessels of the retina. Clinically significant DME occurs when fluid leaks into the center of the macula, the light-sensitive part of the retina responsible for sharp, direct vision. Fluid in the macula can cause severe vision loss or blindness.

Various VEGF inhibitors, such as the VEGF trap EYLEA® (aflibercept), have been approved to treat such eye disorders. Aflibercept is a fusion protein composed of an IgG1 Fc domain fused to the Ig domain 2 of VEGFR-1 and Ig domain 3 of VEGFR-2. Aflibercept is marketed as Eylea® (Regeneron, Tarrytown, NY) for the treatment of various ocular conditions, including wet type AMD, and is formulated for intravitreal administration. The fusion protein is also marketed as Zaltrap® (z/v-aflibercept) (Regeneron, Tarrytown, NY) for the treatment of certain types of cancer and is formulated for intravenous administration.

It is an important that a drug product meant for intravenous administration satisfy a predetermined level of purity and quality. Impurities can be caused by chemical modifications of a biologic such as aflibercept during its manufacturing, degradation products of formulation excipients, or degradation products formed through the reaction of the biologic and formulation excipients. How such impurities form can be essential in studying the root cause of the problem and to formulate methods to avoid the formation of such impurities.

Moreover, a large variety of factors can affect the safety, efficacy and stability of a protein drug such as its manufacturing process, potential impurities developed during manufacture, excipients used to formulate a drug product of the protein, storage conditions, etc. Changes in any of these various factors can adversely and sometimes unexpectedly affect the safety, efficacy and stability of a protein drug.

SUMMARY

The present disclosure provides processes of preparing and purifying a VEGF receptor fusion protein, e.g., aflibercept. Also disclosed are formulations including a high concentration of the VEGF receptor fusion protein with a low amount of an aspartyl protease, e.g., cathepsin D.

In an embodiment, the process can include flowing a drug substance intermediate that comprises a VEGF receptor fusion protein, a surfactant, and an aspartyl protease through a size exclusion chromatography (SEC) column; collecting a first eluate from the SEC column that comprises the VEGF receptor protein and an amount of less than 1 ppm of the aspartyl protease; and excluding from the collected first eluate a second eluate that comprises the VEGF receptor fusion protein and the aspartyl protease. In some embodiments, the collected first eluate can have even less of the aspartyl protease (e.g., cathepsin D) such as less than 0.7 ppm, 0.5 ppm, 0.3 ppm, 0.1 ppm, 0.07 ppm, 0.05 ppm, etc. of the aspartyl protease (e.g., cathepsin D).

In another embodiment, the process can include purifying aflibercept by flowing a drug substance intermediate that comprises aflibercept, a surfactant, and cathepsin D through a size exclusion chromatography (SEC) column; collecting a first eluate from the SEC column that comprises the aflibercept and an amount of less than 1 ppm of the cathepsin D; and excluding from the collected first eluate a second eluate that comprises the aflibercept and the cathepsin D.

Other embodiments can include a process of purifying a VEGF receptor fusion protein (e.g., aflibercept) by flowing a mixture comprising the VEGF receptor fusion protein, a surfactant, and an aspartyl protease (e.g., cathepsin D) through a size exclusion chromatography (SEC) column; and collecting a first eluate from the SEC column that comprises the VEGF receptor protein and an amount of less than 1 ppm of the aspartyl protease; and excluding a second eluate from the SEC column that comprises the VEGF receptor protein and greater than 1 ppm of the aspartyl protease to thereby purify the VEGF receptor fusion protein. In certain embodiments, the process can include collecting a first eluate from the SEC column that comprises the VEGF receptor protein and even less of the aspartyl protease such as an amount of less than 0.7 ppm of the aspartyl protease, e.g., less than 0.5 ppm, 0.3 ppm, 0.1 ppm, 0.07 ppm, 0.05 ppm, etc. of the aspartyl protease. In other embodiments, the process can include excluding the second eluate from the SEC column that comprises the VEGF receptor protein and greater than the amount of the aspartyl protease collected in the first eluate such as excluding a second eluate from the SEC column that comprises the VEGF receptor protein and greater than 0.05 ppm, 0.07 ppm, 0.1 ppm, 0.3 ppm, 0.5 ppm, 0.7 ppm of the aspartyl protease to thereby purify the VEGF receptor fusion protein.

Also disclosed herein is a process of forming a high concentration aflibercept and low concentration aspartyl protease (e.g., cathepsin D) containing composition. In an embodiment, the process can include flowing a drug substance intermediate, or a mixture comprising the VEGF receptor fusion protein, a surfactant, and an aspartyl protease through a size exclusion chromatography (SEC) column; and collecting a first eluate from the SEC column that comprises the VEGF receptor protein and an amount of less than 1 ppm of the aspartyl protease, e.g., an amount less than 0.7 ppm, 0.5 ppm, 0.3 ppm, 0.1 ppm, 0.07 ppm, 0.05 ppm, etc. The process can further exclude a second eluate that comprises the VEGF receptor protein and greater than 1 ppm of the aspartyl protease, e.g., an amount greater than 0.7 ppm, 0.5 ppm, 0.3 ppm, 0.1 ppm, 0.07 ppm, 0.05 ppm, etc. of the aspartyl protease, to thereby form the high concentration aflibercept and low concentration aspartyl protease containing composition.

Suitable surfactants can include non-ionic surfactants such as those that have a polyoxyethylene moiety, e.g., a polysorbate, such as polysorbate 20, polysorbate 80, a poloxamer, such as poloxamer 188, a polyethylene glycol, a polyglycol ester of hydroxystearic acid, a glycerol polyethylene glycol ricinoleate, and any mixture thereof. Surfactants in the drug substance intermediate or mixture for separation by the SEC column can be present in greater than 0.0003% such as at least about 0.001%, e.g., at least about 0.003%, about 0.01%, about 0.1% and greater amounts such as up to and including at least about 2% and any range thereof such as from greater than 0.0003% to about 2%. The surfactant can be added to the drug substance intermediate, or mixture, as the case maybe, prior to flowing it through the SEC column or concurrently while flowing the DSI or mixture through the SEC column.

Advantageously, the amount of the aspartyl protease in an eluate, e.g., a first and/or second eluate, can be determined by an enzyme-linked immunosorbent assay (ELISA), or an activity assay, or by liquid chromatography-mass spectrometry (LC-MS), or by a combination of two or more thereof. The ELISA can be based on an anti-Chinese hamster ovary cathepsin D antibody, for example. Any one or more than one of these techniques can be used to determine an amount of the aspartyl protease in the first or second eluate.

In addition, any one or more of an enzyme-linked immunosorbent assay (ELISA), or an activity assay, or by liquid chromatography-mass spectrometry (LC-MS), or by a combination of two or more thereof, can be used to determine, prior to collecting an eluate, e.g., a first eluate, an amount of the aspartyl protease in one or more fractions of the drug substance intermediate or mixture eluting from the SEC column. By determining the amount of the aspartyl protease in one or more fractions of the drug substance intermediate or mixture eluting from the SEC column, the SEC purification process can be carried out with a predetermined start and end time of collecting a first eluate from the SEC column.

In some aspects, the process further comprises, prior to purifying a VEGF receptor fusion protein via an SEC column, preparing a drug substance intermediate. The process can include harvesting a preparation of the anti-VEGF protein produced by a host cell genetically engineered to express the anti-VEGF protein in a culture medium, purifying the preparation by liquid chromatography, and adding a surfactant to the purified preparation to form a drug substance intermediate. Advantageously, the preparation can be purified by Protein A chromatography, anion exchange chromatography, cation exchange chromatography, hydrophobic interaction chromatography, or a combination of two or more thereof.

In another embodiment, formulations of the present disclosure can comprise a high concentration VEGF receptor protein, e.g., aflibercept and low concentration aspartyl protease (e.g., cathepsin D). For example, formulations of the present disclosure are suitable for a high concentration of the VEGF receptor fusion protein, e.g., aflibercept, such as a concentration of at least 41 mg/mL of the VEGF receptor fusion protein in the formulation. In some embodiments, the concentration of the VEGF receptor fusion protein in a formulation can range from about 100 mg/mL to about 300 mg/mL. Advantageously, the formulations can have a low amount of an aspartyl protease (e.g., cathepsin D) such as less than 1 ppm, e.g., less than 0.7 ppm, 0.5 ppm, 0.3 ppm, 0.1 ppm, 0.1 ppm, 0.07 ppm, 0.05 ppm, etc. of the aspartyl protease (e.g., cathepsin D) in the formulation. The formulation can further include one or more pharmaceutically acceptable excipients and aflibercept at concentration of from about 100 mg/mL to about 300 mg/mL, wherein the formulation includes less than 0.3 ppm of cathepsin D and has a pH of from 5.5 to 6.1. In some embodiments, the pH of the formulation can range from about 5.0 to about 6.5, such as from about 5.5 to about 6.1.

These and other aspects of the disclosure will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the disclosure.

BRIEF DESCRIPTION OF THE DRAWINGS

FIG. 3 is a chart of NR-1% formed over time when DS samples are incubated with cathepsin D at a pH of 6.3 and 4.5, according to an exemplary embodiment.

FIG. 4 is an exemplary workflow for quantifying the amount of cathepsin D present in a sample, according to an exemplary embodiment.

FIG. 5 show exemplary parameters helpful for quantifying the amount of cathepsin D present in a sample, according to an exemplary embodiment.

FIG. 6 is a table of average level of cathepsin D present in facility A and facility B's DSI samples, which are calculated according to an exemplary embodiment.

FIG. 11 shows details of the purification scheme for anti-cathepsin D antibody shown in FIG. 10.

FIG. 21 shows Cathepsin D activity data for DSI in-process pools produced in low concentration (LC) DSI lots (20 lots) and high concentration (HC) DSI lots (20 lots), according to an exemplary embodiment.

FIG. 29A displays activity assay (top panels) and ELISA data (bottom panels) of cathepsin D concentration in source DSI and at FDS, pre (red) and post (blue) change, with fold reduction, according to an exemplary embodiment.

FIG. 30A shows a chart of CE-SDS stability data at 25° C. for modified high concentration formulated drug substance (FDS) lots (black) at 3 months compared to investigation FDS lot without the modification (blue, rectangles) and comparator lots (red, diamonds), according to an exemplary embodiment.

FIG. 30B shows a chart of stability data at 25° C. for pre-optimization (red, upper line), post-optimization (green), and comparators (black) over 6 months, according to an exemplary embodiment.

DETAILED DESCRIPTION

Figure 1:
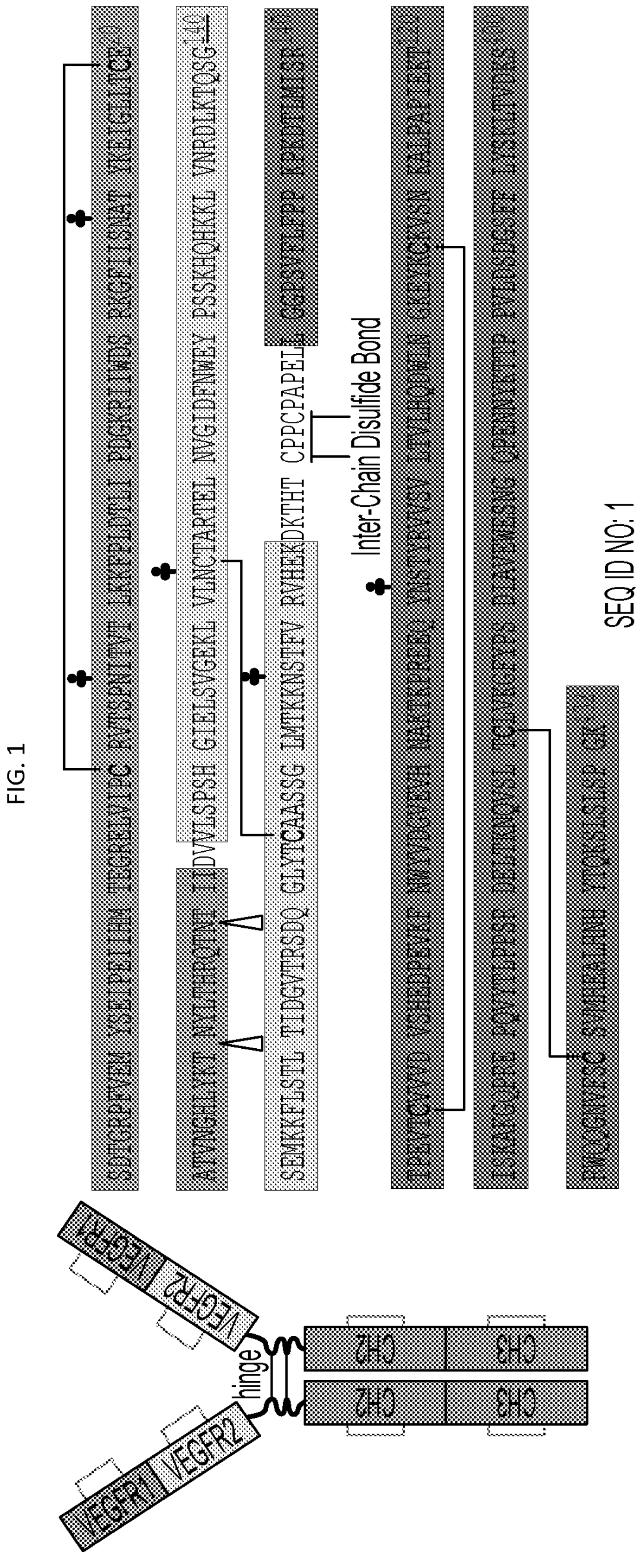
FIG. 1 is a cartoon representation of the structure and sequence of aflibercept (SEQ ID NO:1), according to an exemplary embodiment.

Unless described otherwise, all technical and scientific terms used herein have the same meaning as commonly understood by one of ordinary skill in the art to which this disclosure belongs. Methods and materials similar or equivalent to those described herein known to the skilled artisan can be used in the practice of particular embodiments described herein.

The term "a" should be understood to mean "at least one" and the terms "about" and "approximately" should be understood to permit standard variation as would be understood by those of ordinary skill in the art and where ranges are provided, endpoints are included.

A "sample" refers to a small portion of a larger quantity of material. Generally, testing according to the methods described herein is performed on a sample. The sample is typically obtained from a recombinant polypeptide preparation obtained, for example, from cultured host cells. A sample may be obtained from, for example but not limited to, harvested cell culture fluid, from an in-process pool at a certain step in a purification process, or from the final purified product.

As used herein, the term "angiogenic eye disorder" means any disease of the eye, which is caused by or associated with the growth or proliferation of blood vessels or by blood vessel leakage.

As used herein, the term "chemically defined medium" or "chemically defined media" (both abbreviated "CDM") refers to a synthetic growth medium in which the identity and concentration of all the ingredients are defined. Chemically defined media do not contain bacterial, yeast, animal, or plant extracts, animal serum, or plasma, although individual plant or animal-derived components (e.g., proteins, polypeptides, etc.) may be added. Chemically defined media may contain inorganic salts such as phosphates, sulfates, and the like needed to support growth. The carbon source is defined, and is usually a sugar such as glucose, lactose, galactose, and the like, or other compounds such as glycerol, lactate, acetate, and the like. While certain chemically defined culture media also use phosphate salts as a buffer, other buffers may be employed such as sodium bicarbonate. HEPES, citrate, triethanolamine, and the like. Examples of commercially available chemically defined media include, but are not limited to, various Dulbecco's Modified Eagle's (DME) media (Sigma-Aldrich Co; SAFC Biosciences, Inc.), Ham's Nutrient Mixture (Sigma-Aldrich Co; SAFC Biosciences, Inc.), various EX-CELLs mediums (Sigma-Aldrich Co; SAFC Biosciences, Inc.), various IS CHO-CD mediums (FUJIFILM Irvine Scientific), combinations thereof, and the like. Methods of preparing chemically defined culture media are known in the art, for example, in U.S. Pat. Nos. 6,171,825 and 6,936,441, WO 2007/077217, and U.S. Patent Application Publication Nos. 2008/0009040 and 2007/0212770, the entire teachings of which are herein incorporated by reference.

As used herein, the term "formulation" refers to a protein of interest that is formulated together with one or more pharmaceutically acceptable vehicles or excipients. In one aspect, the protein of interest is aflibercept and/or a truncated aflibercept. In some exemplary embodiments, the amount of protein of interest in the formulation can range from about 0.01 mg/mL to about 600 mg/mL. In some specific embodiments, the amount of the protein of interest in the formulation can be about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 225 mg/mL, about 250 mg/mL about 275 mg/mL, about 300 mg/mL, about 325 mg/mL, about 350 mg/mL, about 375 mg/mL, about 400 mg/mL, about 425 mg/mL, about 450 mg/mL, about 475 mg/mL, about 500 mg/mL, about 525 mg/mL, about 550 mg/mL, about 575 mg/mL, or about 600 mg/mL. In other specific embodiments, the amount of the protein of interest in the formulation can be at least 41 mg/mL, such at least 100 mg/mL. For example, the amount of the protein of interest in the formulation can be at least 41 mg/mL to about 600 mg/mL and any value therebetween. In some exemplary embodiments, pH of the formulation can be greater than about 5.0. In one exemplary embodiment, the pH can be greater than about 5.0, greater than about 5.5, greater than about 6.0, greater than about 6.5, greater than about 7.0, greater than about 7.5, greater than about 8.0, or greater than about 8.5. In another exemplary embodiment, the pH can range from about 5.0 to about 6.5, such as from about 5.5 to about 6.1.

As used herein, the term "database" refers to a bioinformatics tool, which provides for the possibility of searching the uninterpreted MS-MS spectra against all possible sequences in the database(s). Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com//proteinpilot), Phenyx (www.phenyx-ms.com), Sorcerer (www.sagenresearch.com), OMSSA (www.pubchem.ncbi.nilm.nih.gov/omssa/), X!Tandem (www.thegpm.org/TANDEM/), Protein Prospector (www.prospector.ucsf.edu/prospector/mshome.htm). Byonic (www.proteinmetrics.com/products/byonic) or Sequest (fields.scripps.edu/sequest).

A "purification step" may be part of an overall purification process resulting in a "homogeneous" composition, which is used herein to refer to a composition comprising less than about 100 ppm HCP (100 ppm) in a composition comprising the protein of interest, or less than about 90 ppm (90 ppm), or less than about 80 ppm (80 ppm), or less than about 70 ppm (70 ppm), or less than about 60 ppm (60 ppm), or less than about 50 ppm 50 ppm), or less than about 40 ppm (40 ppm), or less than about 30 ppm (30 ppm), or less than about 20 ppm (20 ppm), or less than about 10 ppm (10 ppm), or less than about 5 ppm (5 ppm), or less than about 3 ppm (3 ppm) or less than about 1 ppm (1 ppm). In certain embodiments, the HCP is a single HCP species. In one embodiment, the single HCP species is Cathepsin D. Cathepsin D is an aspartic endo-protease that is ubiquitously distributed in lysosomes. The main function of cathepsin D is to degrade proteins and activate precursors of bioactive proteins in pre-lysosomal compartments. The sequence of cathepsin D is represented in SEQ ID NO: 2.

```
SEQ ID NO: 2:
SAVIRIPLRKFTSIRRTMTEVGGSVEDLILKGPITKYSNQSPAETKGPV

SELLKNYLDAQYYGEIGIGTPPQCFTVVFDTGSSNLWVPSIHCKLLDIA

CWIHHKYNSGKSSTFVKNGTSEDIHYGSGSLSGYLSQDTVSVPCKSEQP

GGLKVEKQIFGEAIKQPGITFIAAKFDGILGMGYPSISVNNVVPVFDNL

MQQKLVEKNIFSFFLNRDPTGQPGGELMLGGIDSKYYEGELSYLNVTRK

AYWQVHMDQLDVANGLTLCKGGCEAIVDTGTSLLVGPVDEVKELQKAIG

AVPLIQGEYMIPCEKVSSLPSVTLKLGGKDYELSPSKYVLKVSQGGKTI

CLSGFMGMDIPPPSGPLWILGDVFIGTYYTVFDRDNNRVGFAKAATLEQ

KLISEEDLGGEQKLISEEDLHHHHHH
```

As used herein, the term "ultrafiltration" or "UF" can include a membrane filtration process similar to reverse osmosis, using hydrostatic pressure to force water through a semi-permeable membrane. Ultrafiltration is described in detail in: LEOS J. ZEMAN & ANDREW L. ZYDNEY, MICROFILTRATION AND ULTRAFILTRATION: PRINCIPLES AND APPLICATIONS (1996), the entire teaching of which is herein incorporated Filters with a pore size of smaller than 0.1 pin can be used for ultrafiltration. By employing filters having such small pore size, the volume of the sample can be reduced through permeation of the sample buffer through the filter while proteins are retained behind the filter.

As used herein, "diafiltration" or "DF" can include a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to a solution being ultrafiltered at a rate approximately equal to the ultrafiltration rate. This washes microspecies from the solution at a constant volume. In certain exemplary embodiments of the present disclosure, a diafiltration step can be employed to exchange various buffers used in connection with the instant disclosure, for example, prior to chromatography or other production steps, as well as to remove impurities from the protein preparation. As used herein, the term "downstream process technology" refers to one or more techniques used after the upstream process technologies to produce a protein. Downstream process technology includes, for example, production of a protein product, using, for example, affinity chromatography, including Protein A affinity chromatography as well as affinity chromatography that uses a solid phase having a well-defined molecule like VEGF that can interact with its cognate like a VEGF receptor (VEGFR), ion exchange chromatography, such as anion or cation exchange chromatography, hydrophobic interaction chromatography, or displacement chromatography.

The phrase "recombinant host cell" (or simply "host cell") includes a cell into which a recombinant expression vector coding for a protein of interest has been introduced. It should be understood that such a term is intended to refer not only to a particular subject cell but to a progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the kingdoms of life. In one aspect, eukaryotic cells include protist, fungal, plant and animal cells. In a further aspect, host cells include eukaryotic cells such as plant and/or animal cells. The cells can be mammalian cells, fish cells, insect cells, amphibian cells or avian cells. In a particular aspect, the host cell is a mammalian cell. A wide variety of mammalian cell lines suitable for growth in culture are available from the American Type Culture Collection (Manassas, Va.) and other depositories as well as commercial vendors. Cells that can be used in the processes of the disclosure include, but not limited to, MK2.7 cells, PER-C6 cells, Chinese hamster ovary cells (CHO), such as CHO-K1 (ATCC CCL-61), DG44 (Chasin et al., 1986, *Som. Cell Molec. Genet.,* 12:555-556: Kolkekar et al., 1997. *Biochemistry,* 36: 10901-10909; and WO 01/92337 A2), dihydrofolate reductase negative CHO cells (CHO/−DHFR, Urlaub and Chasin, 1980, *Proc. Natl. Acad. Sci. USA,* 77:4216), and dp12.CHO cells (U.S. Pat. No. 5,721,121); monkey kidney cells (CV1, ATCC CCL-70); monkey kidney CV1 cells transformed by SV40 (COS cells, COS-7, ATCC CRL-1651); HEK 293 cells, and Sp2/0 cells, 5L8 hybridoma cells. Daudi cells, EL4 cells, HeLa cells, HL-60 cells, K562 cells, Jurkat cells, THP-1 cells, Sp2/0 cells, primary epithelial cells (e.g., keratinocytes, cervical epithelial cells, bronchial epithelial cells, tracheal epithelial cells, kidney epithelial cells and retinal epithelial cells) and established cell lines and their strains (e.g., human embryonic kidney cells (e.g., 293 cells, or 293 cells subcloned for growth in suspension culture, Graham et al., 1977, *J. Gen. Virol.,* 36:59); baby hamster kidney cells (BHK, ATCC CCL-10); mouse sertoli cells (TM4, Mather, 1980. *Biol. Reprod.,* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CR L-1442); TRI cells (Mather, 1982, *Annals NY Acad. Sci.,* 383:44-68); MCR 5 cells; FS4 cells; PER-C6 retinal cells, MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells. WI-28 VA 13, 2RA cells, WISH cells, BS-C-I cells, LLC-$MK_2$ cells, Clone M-3 cells, 1-10 cells, RAG cells, TCMK-1 cells, Y-1 cells, LLC-$PK_1$ cells, PK(15) cells, $GH_1$ cells, $GH_3$ cells, L2 cells, LLC-RC 256 cells, $MH_1C_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., TRG-2 cells, IMR-33 cells, Don cells, GH K-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells. MRC-5 cells. WI-38 cells, WI-26 cells, $MiCl_1$ cells, CV-1 cells, COS-1 cells, COS-3 cells, COS-7 cells, African green monkey kidney cells (VERO-76, ATCC CRL-1587; VERO, ATCC CCL-81); DBS-FrhL-2 cells, BALB/3T3 cells, F9 cells, SV-T2 cells, M-MSV-BALB/3T3 cells, K-BALB cells, BLO-11 cells, NOR-10 cells, $C_3H$/IOTI/2 cells, $HSDM_1C_3$ cells, KLN205 cells. McCoy cells, Mouse L cells, Strain 2071 (Mouse L) cells, L-M strain (Mouse L) cells, L-MTK (Mouse L) cells. NCTFC clones 2472 and 2555, SCC-PSA1 cells, Swiss/3T3 cells, Indian muntac cells, SIRC cells, Cn cells, and Jensen cells, or derivatives thereof) or any other cell type known to one skilled in the art.

As used herein, the term "host cell proteins" (HCP) includes protein derived from a host cell and can be unrelated to the desired protein of interest. Host cell proteins can be a process-related impurity which can be derived from the manufacturing process and can include three major categories: cell substrate-derived, cell culture-derived and downstream derived. Cell substrate-derived impurities include, but are not limited to, proteins derived from a host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

The term "parts per million" or "ppm" are used interchangeably herein to refer to a measure of purity of the protein of interest purified by a method of the disclosure. The unit ppm refers to the amount of HCP or CHOP in nanograms/milliliter per protein of interest in milligrams/milliliter (i.e., CHOP ppm=(CHOP ng/ml)/(protein of interest mg/ml), where the proteins are in solution). Where the proteins are dried (such as by lyophilization), ppm refers to (CHOP ng)/(protein of interest mg)). Impurities may also be expressed as "ppm" which is used interchangeably with ppm.

In some exemplary embodiments, the host cell protein can have a pI in the range of about 4.5 to about 9.0. In an exemplary embodiment, the pI can be about 4.5, about 5.0, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0.

As used herein, the term "liquid chromatography" refers to a process in which a biological/chemical mixture carried by a liquid can be separated into components as a result of differential distribution of the components as they flow through (or into) a stationary liquid or solid phase. Non-limiting examples of liquid chromatography include reverse phase liquid chromatography, ion-exchange chromatography, size exclusion chromatography, affinity chromatography, mixed-mode chromatography or hydrophobic chromatography.

As used herein, "affinity chromatography" can include separations including any method by which two substances are separated based upon their affinity to a chromatographic material. It can comprise subjecting the substances to a column comprising a suitable affinity chromatographic media. Non-limiting examples of such chromatographic media include, but are not limited to, Protein A resin, Protein G resin, affinity supports comprising an antigen against which a binding molecule (e.g., antibody) was produced, protein capable of binding to a protein of interest and affinity supports comprising an Fc binding protein. In one aspect, an affinity column can be equilibrated with a suitable buffer prior to sample loading. An example of a suitable buffer can be a Tris/NaCl buffer, pH around 7.0 to 8.0. A skilled artisan can develop a suitable buffer without undue burden. Following this equilibration, a sample can be loaded onto the column. Following the loading of the column, the column can be washed one or multiple times using, for example, the equilibrating buffer. Other washes, including washes employing different buffers, can be used before eluting the column. The affinity column can then be eluted using an appropriate elution buffer. An example of a suitable elution buffer can be an acetic acid/NaCl buffer, pH around 2.0 to 3.5. Again, the skilled artisan can develop an appropriate elution buffer without undue burden. The eluate can be monitored using techniques well known to those skilled in the art, including UV. For example, the absorbance at 280 nm can be employed, especially if the sample of interest comprises aromatic rings (e.g., proteins having aromatic amino acids like tryptophan).

As used herein, "ion exchange chromatography" can refer to separations including any method by which two substances are separated based on differences in their respective ionic charges, either on the molecule of interest and/or chromatographic material as a whole or locally on specific regions of the molecule of interest and/or chromatographic material, and thus can employ either cationic exchange material or anionic exchange material. Ion exchange chromatography separates molecules based on differences between the local charges of the molecules of interest and the local charges of the chromatographic material. A packed ion-exchange chromatography column or an ion-exchange membrane device can be operated in a bind-elute mode, a flowthrough mode, or a hybrid mode. After washing the column or the membrane device with an equilibration buffer or another buffer, product recovery can be achieved by increasing the ionic strength (i.e., conductivity) of the elution buffer to compete with the solute for the charged sites of the ion exchange matrix. Changing the pH and thereby altering the charge of the solute can be another way to achieve elution of the solute. The change in conductivity or pH may be gradual (gradient elution) or stepwise (step elution). Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange medias or support can include DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow, and Capto™ S are all available from GE Healthcare. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNO-Sphere™ S from BioRad, Hercules, Calif., Eshmuno® S from EMD Millipore, MA.

As used herein, the term "hydrophobic interaction chromatography resin" can include a solid phase, which can be covalently modified with phenyl, octyl, butyl or the like. It can use the properties of hydrophobicity to separate molecules from one another. In this type of chromatography, hydrophobic groups such as, phenyl, octyl, hexyl or butyl can form the stationary phase of a column. Molecules such as proteins, peptides and the like pass through a HIC (hydrophobic interactive chromatography) column that possess one or more hydrophobic regions on their surface or have hydrophobic pockets and are able to interact with hydrophobic groups comprising a HIC's stationary phase. Examples of HIC resins or support include Phenyl sepharose FF, Capto Phenyl (GE Healthcare. Uppsala, Sweden), Phenyl 650-M (Tosoh Bioscience, Tokyo, Japan) and Sartobind Phenyl (Sartorius corporation, New York, USA).

As used herein, the term "Mixed Mode Chromatography" or "multimodal chromatography" (both "MMC") includes a chromatographic method in which solutes interact with a stationary phase through more than one interaction mode or mechanism. MMC can be used as an alternative or complementary tool to traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings, longer column lifetimes and operation flexibility compared to affinity-based methods. In some exemplary embodiments, mixed mode chromatography media can be comprised of mixed mode ligands coupled to an organic or inorganic support, sometimes denoted a base matrix, directly or via a spacer. The support may be in the form of particles, such as essentially spherical particles, a monolith, filter, membrane, surface, capillaries, etc. In some exemplary embodiments, the support can be prepared from a native polymer such as cross-linked carbohydrate material, such as agarose, agPV, cellulose, dextran, chitosan, konjac, carrageenan, gellan, alginate, etc. To obtain high adsorption capacities, the support can be porous and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964), the entire teachings of which are herein incorporated). Alternatively, the support can be prepared from a synthetic polymer such as cross-linked synthetic polymers, for example, styrene or styrene derivatives, divinylbenzene, acrylamides, acrylate esters, methacrylate esters, vinyl esters, vinyl amides and the like. Such synthetic polymers can be produced according to standard methods, for example, "Styrene based polymer supports developed by suspension polymerization" (R Arshady: Chimica e L'Industria 70(9), 70-75 (1988), the entire teachings of which are herein incorporated). Porous native or synthetic polymer supports are also available from commercial sources, such as such as GE Healthcare, Uppsala. Sweden.

As used herein, the term "mass spectrometer" includes a device capable of identifying specific molecular species and measuring their accurate masses. The term is meant to include any molecular detector into which a polypeptide or peptide may be characterized. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends on the application. In some exemplary embodiments, the mass spectrometer can be a tandem mass spectrometer. As used herein, the term "tandem mass spectrometry" includes a technique where structural information on sample molecules is obtained by using multiple stages of mass selection and mass separation. A prerequisite is that the sample molecules be transformed into a gas phase and ionized so that fragments are formed in a predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on, as long as one can obtain meaningful information, or the fragment ion signal is detectable. Tandem MS has been successfully performed with a wide variety of analyzer combinations.

Which analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device.

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited, to sequencing amino acids of the protein fragments, determining protein sequencing, determining protein de novo sequencing, locating post-translational modifications, or identifying post translational modifications, or comparability analysis, or combinations thereof.

As used herein, the term "subject" refers to a mammal (e.g., rat, mouse, cat, dog, cow, sheep, horse, goat, rabbit), preferably a human in need of prevention and/or treatment of a disorder such as a cancer or an angiogenic eye disorder. The subject may have the disorder, e.g., cancer or angiogenic eye disorder, or be predisposed to developing the disorder, e.g., cancer or angiogenic eye disorder.

In terms of protein formulation, the term "stable." as used herein refers to the protein of interest within the formulation being able to retain an acceptable degree of chemical structure or biological function after storage under exemplary conditions defined herein. A formulation may be stable even though the protein of interest contained therein does not maintain 100% of its chemical structure or biological function after storage for a defined amount of time. Under certain circumstances, maintenance of about 90%, about 95%, about 96%, about 97%, about 98% or about 99% of a protein of interest's structure or function after storage for a defined amount of time may be regarded as "stable."

The term "treat" or "treatment" refers to a therapeutic measure that reverses, stabilizes or eliminates an undesired disease or disorder (e.g., an angiogenic eye disorder or cancer), for example, by causing the regression, stabilization or elimination of one or more symptoms or indicia of such disease or disorder by any clinically measurable degree, for example, with regard to an angiogenic eye disorder, by causing a reduction in or maintenance of diabetic retinopathy severity score (DRSS), by improving or maintaining vision (e.g., in best corrected visual acuity, for example, as measured by an increase in ETDRS letters), increasing or maintaining visual field and/or reducing or maintaining central retinal thickness and, with respect to cancer, stopping or reversing the growth, survival and/or metastasis of cancer cells in the subject. Typically, the therapeutic measure is administration of one or more doses of a therapeutically effective amount of VEGF MiniTrap to the subject with the disease or disorder.

As used herein, the term "upstream process technology," in the context of protein preparation, refers to activities involving the production and collection of proteins from cells during or following the cell culture of a protein of interest. As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host cell, the host cell can be maintained under conditions suitable for expression of the relevant nucleotide coding sequences, and the collection and production of the desired recombinant protein.

When using the cell culture techniques of the instant disclosure, a protein of interest can be produced intracellularly, in the periplasmic space, or directly secreted into the medium. In embodiments where the protein of interest is produced intracellularly, particulate debris—either host cells or lysed cells (e.g., resulting from homogenization) can be removed by a variety of techniques, including, but not limited to, centrifugation or ultrafiltration. Where the protein of interest is secreted into the medium, supernatants from such expression systems can be first concentrated using a commercially available protein concentration filter, for example, using an Amicon™ or Millipore Pellicon™ ultrafiltration unit. In one aspect, the protein of interest may be harvested by centrifugation followed by depth filtration and then affinity capture chromatography.

As used herein, a "VEGF antagonist" or "anti-VEGF protein" is any protein or peptide that binds to or interacts with VEGF. Typically, this binding to or interacting with inhibits the binding of VEGF to its receptors (VEGFR1 and VEGFR2), and/or inhibits the biological signaling and activity of VEGF. VEGF antagonists include molecules which interfere with the interaction between VEGF and a natural VEGF receptor, for example, molecules which bind to VEGF or a VEGF receptor and prevent or otherwise hinder the interaction between VEGF and a VEGF receptor. Specific exemplary VEGF antagonists include anti-VEGF antibodies (e.g., ranibizumab [LUCENTIS®]), anti-VEGF receptor antibodies (e.g., anti-VEGFR1 antibodies, anti-VEGFR2 antibodies and the like), and VEGF receptor-based chimeric molecules or VEGF-inhibiting fusion proteins (also referred to herein as "VEGF-Traps" or "VEGF MiniTraps"), such as aflibercept, ziv-aflibercept and a protein having an amino acid having SEQ ID NO: 1. Other examples of VEGF-Traps are ALT-L9, M710, FYB203 and CHS-2020. Additional examples of VEGF-Traps can be found in U.S. Pat. Nos. 7,070,959; 7,306,799; 7,374,757; 7,374,758; 7,531,173; 7,608,261; 5,952,199; 6,100,071; 6,383,486; 6,897,294 & 7,771,721, which are specifically incorporated herein by reference in their entirety.

For purposes herein, a "VEGF receptor fusion protein" refers to a molecule that comprises one or more VEGF receptors or domains thereof, fused to another polypeptide, which interferes with the interaction between VEGF and a natural VEGF receptor, e.g., wherein two of such fusion polypeptides are associated thereby forming a homodimer or other multimer. Such VEGF receptor fusion proteins may be referred to as a "VEGF-Trap" or "VEGF Trap".

VEGF receptor-based chimeric molecules include chimeric polypeptides which comprise two or more immunoglobulin (Ig)-like domains of a VEGF receptor such as VEGFR1 (also referred to as Fit1) and/or VEGFR2 (also referred to as Flk1 or KDR), and may also comprise a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) (also known as aflibercept; marketed under the product name EYLEA®) or conbercept (sold commercially by Chengdu Kanghong Biotechnology Co., Ltd.). See International patent application publication no. WO2005/121176 or WO2007/112675 The terms "aflibercept" and "conbercept" include biosimilar versions thereof. A biosimilar version of a reference product (e.g., aflibercept) generally refers to a product comprising the identical amino acid sequence, but includes products which are biosimilar under the U.S. Biologics Price Competition and Innovation Act.

In certain exemplary embodiments, aflibercept comprises the amino acid sequence set forth as

```
                                            (SEQ ID NO: 1)
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTUDVVLSPSHGIELSVGEKLVLNCTARTELNVGIDENWEYPSSKHQHK

KLVNRDLKTQSGSEMKKFLSTLTIDGVTRSDQGLYTCAASSGLMTKKNS

TFVRVHEKDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPGK.
```

As used herein, "viral filtration" can include filtration using suitable filters including, but not limited to, Planova 20N™, 50 N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

The present disclosure provides methods for treating or preventing a cancer (e.g., whose growth and/or metastasis is mediated, at least in part, by VEGF, for example, VEGF-mediated angiogenesis) or an angiogenic eye disorder, in a subject, comprising administering a therapeutically effective amount of compositions or formulations as disclosed herein.

The present disclosure provides a method for treating cancer whose growth and/or metastasis is mediated, at least in part, by VEGF, for example, VEGF-mediated angiogenesis or an angiogenic eye disorder in a subject in need thereof, the method comprising administering a therapeutically effective amount of the compositions set forth herein (Section III and Section VII above), for example, 2 mg, 4 mg, 6 mg, 8 mg or 10 mg of the protein of interest, in no more than about 100 μl, and optionally a further therapeutic agent, to a subject. In one embodiment of the disclosure, administration is done by intravitreal injection. Non-limiting examples of angiogenic eye disorders that are treatable or preventable using the methods herein, include: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; and diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

The mode of administration of such compositions or formulations can vary and can be determined by a skilled practitioner. Routes of administration include parenteral, non-parenteral, oral, rectal, transmucosal, intestinal, parenteral, intramuscular, subcutaneous, intradermal, intramedullary, intrathecal, direct intraventricular, intravenous, intraperitoneal, intranasal, intraocular, inhalation, insufflation, topical, cutaneous, intraocular, intravitreal, transdermal or intra-arterial.

In one embodiment of the disclosure, intravitreal injection of a pharmaceutical formulation of the present disclosure (which includes a compositions or formulations of the present disclosure) includes the step of piercing the eye with a syringe and needle (e.g., 30-gauge injection needle) comprising the formulation and injecting the formulation (e.g., less than about or equal to about 100 microliters; about 40, 50, 55, 56, 57, 57.1, 58, 60 or 70 microliters) into the vitreous of the eye with a sufficient volume as to deliver a therapeutically effective amount as set forth herein, for example, of about 2, 4, 6, 8.0, 8.1, 8.2, 8.3, 8.4, 8.5, 8.6, 8.7, 8.8, 8.9, 10 or 20 mg of the protein of interest. Optionally, the method includes the steps of administering a local anesthetic (e.g., proparacaine, lidocaine or tetracaine), an antibiotic (e.g., a fluoroquinolone), antiseptic (e.g., povidone-iodine) and/or a pupil dilating agent to the eye being injected. In one aspect, a sterile field around the eye to be injected is established before the injection. Following intravitreal injection, the subject is monitored for elevations in intraocular pressure, inflammation and/or blood pressure.

An effective or therapeutically effective amount of protein of interest for an angiogenic eye disorder refers to the amount of the protein of interest sufficient to cause the regression, stabilization or elimination of the cancer or angiogenic eye disorder, for example, by regressing, stabilizing or eliminating one or more symptoms or indicia of the cancer or angiogenic eye disorder by any clinically measurable degree, for example, with regard to an angiogenic eye disorder, by causing a reduction in or maintenance of diabetic retinopathy severity score (DRSS), by improving or maintaining vision (e.g., in best corrected visual acuity as measured by an increase in ETDRS letters), increasing or maintaining visual field and/or reducing or maintaining central retinal thickness and, with respect to cancer, stopping or reversing the growth, survival and/or metastasis of cancer cells in the subject.

In one embodiment of the disclosure, an effective or therapeutically effective amount of a protein of interest such as aflibercept for treating or preventing an angiogenic eye disorder is about 0.5 mg, 2 mg, 3 mg, 4 mg, 5 mg, 6 mg, 7 mg, 7.25 mg, 7.7 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9 mg, 10 mg, 11 mg, 12 mg, 13 mg, 141 mg, 15 mg, 16 mg, 17 mg, 18 mg, 19 mg or 20 mg, e.g., in no more than about 100 μL. The amount may vary depending upon the age and the size of a subject to be administered, target disease, conditions, route of administration, and the like. In certain exemplary embodiments, the initial dose may be followed by administration of a second or a plurality of subsequent doses of the protein of interest in an amount that can be approximately the same or less or more than that of the initial dose, wherein the subsequent doses are separated by at least 1 day to 3 days; at least one week, at least 2 weeks, at least 3 weeks, at least 4 weeks, at least 5 weeks, at least 6 weeks, at least 7 weeks, at least 8 weeks, at least 9 weeks, at least 10 weeks, at least 12 weeks, or at least 14 weeks.

It is to be noted that dosage values can vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The present disclosure relates to anti-VEGF proteins including the VEGF trap protein aflibercept, which is a fusion protein. The instant disclosure also pertains to truncated forms of aflibercept. Disclosed herein are methods of making an VEGF receptor fusion protein such as aflibercept and truncated aflibercept, including production modalities that provide efficient and effective production of these proteins of interest. Further disclosed herein are methods for purifying a VEGF receptor fusion protein such as aflibercept and compositions thereof.

It was discovered during development of a high dose VEGF receptor fusion protein, such as aflibercept, (e.g., a concentration of at least 41 mg/mL) that the stability of the formulated drug product can be variable. For example, and as further discussed in the Examples below, during routine analysis of 25° C. stability data at 6 months for a high dose lot of formulated aflibercept atypical results were obtained for purity and low molecular weight (LMW) by capillary electrophoresis-sodium dodecyl sulfate (CE-SDS) and main peak and aggregate by size exclusion-ultra performance liquid chromatography (SE-UPLC). This lot showed faster fragmentation and aggregation compared to historical lots put on 25° C. stability. This led to an investigation of over 200 process variables where no laboratory, system, or assay error could be identified. Further investigation determined that the root cause of the atypical results for fragmentation and aggregation was a higher level of the host cell protein cathepsin D in the high dose formulation.

It was discovered that an aspartyl protease such as cathepsin D can associate with VEGF receptor fusion protein such as aflibercept and piggy-back through the purification processes involved in preparing a formulated drug product with variable levels of removal. Further, very low levels of the aspartyl protease such as cathepsin D can significantly adversely affect stability of a VEGF receptor fusion protein such as aflibercept. Additionally, high VEGF receptor fusion protein concentration and lower formulation pH, which is useful for stability of high protein concentrations, are more favorable for cathepsin D enzyme activity. To address some of these problems, a process of purifying a VEGF receptor fusion protein was developed through significant effort that involves size exclusion chromatography.

In an embodiment, a process of purifying a VEGF receptor fusion protein can include flowing a drug substance intermediate (DSI) that comprises the VEGF receptor fusion protein (e.g. aflibercept), a surfactant, and an aspartyl protease (e.g., cathepsin D) through a size exclusion chromatography (SEC) column. The DSI can flow through the SEC column by injecting the DSI into a solvent steam (mobile phase) that is passed through the SEC column with a flow through eluted as the end of the SEC column. As discussed further below and in the examples, including a surfactant with the DSI or mixture advantageously facilitates separation of the aspartyl protease from the VEGF receptor fusion protein while the mixture is flowing through the SEC column.

In an aspect, the process can further include collecting a first eluate from the SEC column that comprises the VEGF receptor protein (e.g., aflibercept) and an amount of less than 1 ppm of the aspartyl protease (e.g., cathepsin D), such as less than 0.7 ppm, 0.5 ppm, 0.3 ppm, 0.1 ppm, etc. of the aspartyl protease. In some aspects, the collected first eluate can have even less of the aspartyl protease (e.g., cathepsin D) such as less than 0.07 ppm, 0.05 ppm, etc. of the aspartyl protease (e.g., cathepsin D). Although the yield for collecting the VEGF receptor protein (e.g., aflibercept) is reduced, a second eluate that also includes the VEGF receptor protein and the aspartyl protease can be excluded from the first eluate by directing the second eluate to waste. That is, a second amount of material that includes the VEGF receptor protein and the aspartyl protease eluting from the SEC column is not included in the collected first eluate. The second eluate can have a high amount of the aspartyl protease than the first eluate such as greater than 1 ppm, greater than 0.7 ppm, 0.5 ppm, 0.3 ppm, 0.1 ppm, etc. for example. As explained above, the unit ppm refers to the amount of the aspartyl protease in nanograms/milliliter per protein of interest in milligrams/milliliter (i.e., aspartyl protease ppm=(aspartyl protease ng/ml)/(protein of interest mg/ml), where the proteins are in solution).

In another aspect, the process can include collecting a first eluate from the SEC column that comprises the VEGF receptor protein (e.g., aflibercept) and a predetermined amount of the aspartyl protease (e.g., cathepsin D), which can be predetermined by an assay or LC-MS. The predetermined amount can be an amount of the aspartyl protease (e.g., cathepsin D) in the collected first eluate of less than 1 ppm, such as less than 0.7 ppm, 0.5 ppm, 0.3 ppm, 0.1 ppm, 0.07 ppm, 0.05 ppm, etc. Other embodiments can include a process of purifying a VEGF receptor fusion protein (e.g., aflibercept) by flowing a mixture comprising the VEGF receptor fusion protein, a surfactant, and an aspartyl protease (e.g., cathepsin D) through a size exclusion chromatography (SEC) column; and collecting a first eluate from the SEC column that comprises the VEGF receptor protein and an amount of less than 1 ppm of the aspartyl protease; and excluding a second eluate from the SEC column that comprises the VEGF receptor protein and greater than 1 ppm of the aspartyl protease to thereby purify the VEGF receptor fusion protein. In certain embodiments, the process can include collecting a first eluate from the SEC column that comprises the VEGF receptor protein and even less of the aspartyl protease such as an amount of less than 0.7 ppm of the aspartyl protease, e.g., less than 0.5 ppm, 0.3 ppm, 0.1 ppm, 0.07 ppm, 0.05 ppm, etc. of the aspartyl protease. In other embodiments, the process can include excluding a second eluate from the SEC column that comprises the VEGF receptor protein and greater than the amount of the aspartyl protease collected in the first eluate such as excluding a second eluate from the SEC column that comprises the VEGF receptor protein and greater than 0.05 ppm, 0.07 ppm, 0.1 ppm, 0.3 ppm, 0.5 ppm, 0.7 ppm of the aspartyl protease to thereby purify the VEGF receptor fusion protein.

Also disclosed herein is a process of forming a high concentration aflibercept and low concentration aspartyl protease (e.g., cathepsin D) containing composition. In an embodiment, the process can include flowing a mixture comprising the VEGF receptor fusion protein, a surfactant, and an aspartyl protease through a size exclusion chromatography (SEC) column; and collecting a first eluate from the SEC column that comprises the VEGF receptor protein and an amount of less than 1 ppm of the aspartyl protease, e.g., an amount less than 0.7 ppm, 0.5 ppm, 0.3 ppm, 0.1 ppm, 0.07 ppm, 0.05 ppm, etc. The process can further exclude a second eluate that comprises the VEGF receptor protein and greater than 1 ppm of the aspartyl protease, e.g., an amount greater than 0.7 ppm, 0.5 ppm, 0.3 ppm, 0.1 ppm, 0.07 ppm, 0.05 ppm, etc. of the aspartyl protease, to thereby form the high concentration aflibercept and low concentration aspartyl protease containing composition.

Any of the purification processes can be repeated to collect a pool of purified eluate. Further, the collected eluate or pool of collected eluates can be concentrated and filtered to form a concentrated eluate or pool.

As discussed above and provided in the examples below, including a surfactant during the SEC separation advantageously facilitates separation of the aspartyl protease from the VEGF receptor fusion protein. Suitable surfactants can include non-ionic surfactants such as those that have a polyoxyethylene moiety. Illustrative surfactants in this category include: a polysorbate, e.g., polysorbate 20, polysorbate 80, a poloxamer, e.g., poloxamer 188, polyethylene glycol 3350, a polyglycol ester of hydroxystearic acid such as Kolliphor HS available from BASF, a glycerol polyethylene glycol ricinoleate, Kolliphor ELP, Kolliphor P188, and any mixture thereof. Surfactants in the drug substance intermediate or mixture for separation by SEC column can be present in greater than 0.0003% such as at least about 0.001%, e.g., at least about 0.003%, about 0.01%, about 0.1% and greater amounts such as up to and including at least about 2% and any range thereof such as from greater than 0.0003% to about 2%. The surfactant can be added to the drug substance intermediate or mixture, as the case maybe, prior to flowing it through the SEC column or concurrently while flowing the DSI or mixture through the SEC column.

Advantageously, the amount of the aspartyl protease in an eluate, e.g., a first or second eluate, can be determined by an enzyme-linked immunosorbent assay (ELISA), or an activity assay, or by liquid chromatography-mass spectrometry (LC-MS), or by a combination of two or more thereof. The ELISA can be based on an anti-Chinese hamster ovary cathepsin D antibody, for example. Any one or more than one of these techniques can be used to determine an amount of the aspartyl protease in the first or second eluate.

In addition, any one or more of an enzyme-linked immunosorbent assay (ELISA), or an activity assay, or by liquid chromatography-mass spectrometry (LC-MS), or by a combination of two or more thereof can be used to determine, prior to collecting a first eluate, an amount of the aspartyl protease in one or more fractions of the drug substance intermediate eluting from the SEC column. By determining the amount of the aspartyl protease in one or more fractions of the drug substance intermediate or mixture eluting from the SEC column, the SEC purification process can be carried out with a predetermined start and end time of collecting a first eluate from the SEC column.

The purification methods of the present disclosure can advantageously employ a high concentration of the VEGF receptor fusion protein in the drug substance intermediate, or mixture, as the case maybe, such as, for example, a concentration of at least 41 mg/mL of the VEGF receptor fusion protein, e.g., a concentration of at least 60 mg/mL, 80 mg/mL, 100 mg/mL, 110 mg/ml, etc. of the VEGF receptor fusion protein.

In some aspects, the size exclusion chromatography column can be a high efficiency column. For example, the SEC column can include about 1000 to about 1500 plates.

Advantageously, the purification methods of the present disclosure can be repeated and collected eluates pooled together to form a purified pool. One or more of the collected eluates can be further processed to a formulated drug product including one or more steps of concentrating, filtering, and/or formulating the collected eluate with one or more pharmaceutically acceptable excipients.

In some aspects, the process further comprises, prior to purifying a VEGF receptor fusion protein via an SEC column, preparing a drug substance intermediate. The process can include harvesting a preparation of the anti-VEGF protein produced by a host cell genetically engineered to express the anti-VEGF protein in a culture medium, purifying the preparation by liquid chromatography, and adding a surfactant to the purified preparation to form the drug substance intermediate. Advantageously, the preparation can be purified by Protein A chromatography, anion exchange chromatography, cation exchange chromatography, hydrophobic interaction chromatography, or a combination of two or more thereof.

Advantageously, the present disclosure further provides a high concentration of the VEGF receptor fusion protein, e.g., aflibercept, such as a concentration of at least 41 mg/mL of the VEGF receptor fusion protein in the formulation. As described earlier when referring to formulations, the concentration of the VEGF receptor fusion protein, e.g., aflibercept, in a formulation can range from about 100 mg/mL to about 300 mg/mL. The formulation of the present disclosure can have a low amount of an aspartyl protease (e.g., cathepsin D) such as less than 1 ppm, e.g., less than 0.7 ppm, 0.5 ppm, 0.3 ppm, 0.1 ppm, 0.1 ppm, 0.07 ppm, 0.05 ppm, etc. of the aspartyl protease (e.g., cathepsin D) in the pharmaceutical formulation. The formulation can include one or more pharmaceutically acceptable excipients.

In one exemplary embodiment, the pH of the formulation can be greater than about 5.0, greater than about 5.5, greater than about 6.0, and less than about 6.5, for example. In another exemplary embodiment, the pH can range from about 5.0 to about 6.5, such as from about 5.5 to about 6.1.

Additional aspects of the purification methods and preparation of VEGF receptor fusion protein are described below.

Production of VEGF Receptor Fusion Protein Such as Aflibercept

An anti-VEGF protein can be produced by providing a host cell genetically engineered to express the anti-VEGF protein and a cell culture medium, such as a culture medium with a pH of more than about 6; and harvesting a preparation of the anti-VEGF protein produced by the cell. In one aspect, the production of an anti-VEGF protein further comprises culturing the host cell in a cell culture medium. Harvesting a preparation of the anti-VEGF protein produced by a host cell genetically engineered to express the anti-VEGF protein in a culture medium, with or without purifying the preparation by liquid chromatography, generates a drug substance intermediate.

The cell culture medium can be a chemically defined medium ("CDM"). A CDM is often used because it is a protein-free, chemically-defined formula using no animal-derived components and there is certainty as to the composition of the medium. The cell culture medium can also be a hydrolysate medium or a chemically-defined medium supplemented with a hydrolysate.

In one aspect, the cell culture medium comprises a chemically defined medium. In some specific aspects, the cell culture medium can be supplemented with one of more of the following: a recombinant growth factor: a buffer: an osmolarity regulator; an energy source; and hydrolysate(s). The hydrolysates can be an additional source of free amino acids along with di- and tri-peptides and can be supplemented to the cell culture medium. See Babcock and Wilcox. Partial Replacement of Chemically Defined Media with Plant-Derived Protein Hydrolysates. 5 BioPharm Intl. (2010).

In one aspect, the anti-VEGF protein is selected from the group consisting of aflibercept and recombinant MiniTrap (examples of which are disclosed in U.S. Pat. No. 7,279,159), an aflibercept scFv and other anti-VEGF proteins. In a preferred aspect, the anti-VEGF is aflibercept.

In another aspect, the anti-VEGF protein such as aflibercept is expressed in a suitable host cell. Non-limiting examples of such host cells include, but are not limited to, CHO, CHO K1, EESYR®, NICE®, NS0, Sp2/0, embryonic kidney cells and BHK.

In one aspect, the preparation has less than about 100 ppm of aspartic protease. In certain embodiments, the amount of aspartic protease is between 0.5 ppm to about 100 ppm, 0.5 ppm to about 90 ppm, 0.5 ppm to about 80 ppm, 0.5 ppm to about 70 ppm, 0.5 ppm to about 60 ppm, 0.5 ppm to about 50 ppm, 0.5 ppm to about 40 ppm, 0.5 ppm to about 30 ppm, 0.5 ppm and 20 ppm, or between 0.5 ppm and 15 ppm, or between 0.5 ppm and 10 ppm, or between 0.5 ppm and 8 ppm, or between 0.5 ppm and 5 ppm, or between 0.5 ppm and 3 ppm, or between 0.5 ppm and 2 ppm, or between 0.5 ppm and 1 ppm, or between the limit of assay quantitation (LOQ) and 1 ppm.

In another aspect, the preparation has amount of aspartic protease between about 0.1 ppm to about 100 ppm. In certain embodiments, the amount of aspartic protease is between, about 0.1 ppm to about 0.5 ppm, about 0.1 ppm to about 1 ppm, about 0.1 ppm to about 1 ppm, about 0.1 ppm to about 5 ppm, about 0.1 ppm to about 10 ppm, about 0.1 ppm to about 15 ppm, about 0.1 ppm to about 20 ppm, about 0.5 ppm to about 1 ppm, about 0.1 ppm to about 5 ppm, about 0.1 ppm to about 10 ppm, about 0.1 ppm to about 15 ppm, about 0.1 ppm to about 20 ppm, about 5 ppm to about 10 ppm, about 5 ppm to about 15 ppm, about 5 ppm to about 20 ppm, about 10 ppm to about 15 ppm, about 10 ppm to about 20 ppm, about 15 ppm to about 20 ppm, about 5 ppm to about 30 ppm, about 10 ppm to about 30 ppm, about 15 ppm to about 30 ppm, about 20 ppm to about 30 ppm, about 25 ppm to about 30 ppm, about 5 ppm to about 40 ppm, about 10 ppm to about 40 ppm, about 15 ppm to about 40 ppm, about 20 ppm to about 40 ppm, about 25 ppm to about 40 ppm, about 30 ppm to about 40 ppm, about 35 ppm to about 40 ppm, about 5 ppm to about 50 ppm, about 10 ppm to about 50 ppm, about 15 ppm to about 50 ppm, about 20 ppm to about 50 ppm, about 25 ppm to about 50 ppm, about 30 ppm to about 50 ppm, about 35 ppm to about 50 ppm, about 40 ppm to about 50 ppm, about 45 ppm to about 50 ppm, about 5 ppm to about 60 ppm, about 10 ppm to about 60 ppm, about 15 ppm to about 60 ppm, about 20 ppm to about 60 ppm, about 25 ppm to about 60 ppm, about 30 ppm to about 60 ppm, about 35 ppm to about 60 ppm, about 40 ppm to about 60 ppm, about 45 ppm to about 60 ppm, about 50 ppm to about 60 ppm, about 55 ppm to about 60 ppm, about 5 ppm to about 70 ppm, about 10 ppm to about 70 ppm, about 15 ppm to about 70 ppm, about 20 ppm to about 70 ppm, about 25 ppm to about 70 ppm, about 30 ppm to about 70 ppm, about 35 ppm to about 70 ppm, about 40 ppm to about 70 ppm, about 45 ppm to about 70 ppm, about 50 ppm to about 70 ppm, about 55 ppm to about 70 ppm, about 60 ppm to about 70 ppm, about 65 ppm to about 70 ppm, about 5 ppm to about 80 ppm, about 10 ppm to about 80 ppm, about 15 ppm to about 80 ppm, about 20 ppm to about 80 ppm, about 25 ppm to about 80 ppm, about 30 ppm to about 80 ppm, about 35 ppm to about 80 ppm, about 40 ppm to about 80 ppm, about 45 ppm to about 80 ppm, about 50 ppm to about 80 ppm, about 55 ppm to about 80 ppm, about 60 ppm to about 80 ppm, about 65 ppm to about 80 ppm, about 70 ppm to about 80 ppm, about 75 ppm to about 80 ppm, about 5 ppm to about 90 ppm, about 10 ppm to about 90 ppm, about 15 ppm to about 90 ppm, about 20 ppm to about 90 ppm, about 25 ppm to about 90 ppm, about 30 ppm to about 90 ppm, about 35 ppm to about 90 ppm, about 40 ppm to about 90 ppm, about 45 ppm to about 90 ppm, about 50 ppm to about 90 ppm, about 55 ppm to about 90 ppm, about 60 ppm to about 90 ppm, about 65 ppm to about 90 ppm, about 70 ppm to about 90 ppm, about 75 ppm to about 90 ppm, about 80 ppm to about 90 ppm, about 85 ppm to about 90 ppm, about 5 ppm to about 100 ppm, about 10 ppm to about 100 ppm, about 15 ppm to about 100 ppm, about 20 ppm to about 100 ppm, about 25 ppm to about 100 ppm, about 30 ppm to about 100 ppm, about 35 ppm to about 100 ppm, about 40 ppm to about 100 ppm, about 45 ppm to about 100 ppm, about 50 ppm to about 100 ppm, about 55 ppm to about 100 ppm, about 60 ppm to about 100 ppm, about 65 ppm to about 100 ppm, about 70 ppm to about 100 ppm, about 75 ppm to about 100 ppm, about 80 ppm to about 100 ppm, about 85 ppm to about 100 ppm, about 90 ppm to about 100 ppm, about 95 ppm to about 100 ppm, and ranges between about 0.1 ppm to about 100 ppm.

In yet another aspect, the preparation has less than about 100 ppm of cathepsin D. In certain embodiments, the amount of cathepsin D is between 0.5 ppm to about 100 ppm, 0.5 ppm to about 90 ppm, 0.5 ppm to about 80 ppm, 0.5 ppm to about 70 ppm, 0.5 ppm to about 60 ppm, 0.5 ppm to about 50 ppm, 0.5 ppm to about 40 ppm, 0.5 ppm to about 30 ppm, 0.5 ppm and 20 ppm, or between 0.5 ppm and 15 ppm, or between 0.5 ppm and 10 ppm, or between 0.5 ppm and 8 ppm, or between 0.5 ppm and 5 ppm, or between 0.5 ppm and 3 ppm, or between 0.5 ppm and 2 ppm, or between 0.5 ppm and 1 ppm, or between the limit of assay quantitation (LOQ) and 1 ppm. In certain aspects, the amount of cathepsin D is quantified using an immunoassay or a mass spectrometry assay. In certain aspects, the immunoassay is a total Chinese hamster ovary protein ELISA or a cathepsin D ELISA. In some specific aspects, the immunoassay is a cathepsin D ELISA. In certain aspects, the mass spectrometry assay is LC-MS/MS.

In yet another aspect, the preparation has amount of cathepsin D between about 0.1 ppm to about 100 ppm. In certain embodiments, the amount of cathepsin D is between, about 0.1 ppm to about 0.5 ppm, about 0.1 ppm to about 1 ppm, about 0.1 ppm to about 1 ppm, about 0.1 ppm to about 5 ppm, about 0.1 ppm to about 10 ppm, about 0.1 ppm to about 15 ppm, about 0.1 ppm to about 20 ppm, about 0.5 ppm to about 1 ppm, about 0.1 ppm to about 5 ppm, about 0.1 ppm to about 10 ppm, about 0.1 ppm to about 15 ppm, about 0.1 ppm to about 20 ppm, about 5 ppm to about 10 ppm, about 5 ppm to about 15 ppm, about 5 ppm to about 20 ppm, about 10 ppm to about 15 ppm, about 10 ppm to about 20 ppm, about 15 ppm to about 20 ppm, about 5 ppm to about 30 ppm, about 10 ppm to about 30 ppm, about 15 ppm to about 30 ppm, about 20 ppm to about 30 ppm, about 25 ppm to about 30 ppm, about 5 ppm to about 40 ppm, about 10 ppm to about 40 ppm, about 15 ppm to about 40 ppm, about 20 ppm to about 40 ppm, about 25 ppm to about 40 ppm, about 30 ppm to about 40 ppm, about 35 ppm to about 40 ppm, about 5 ppm to about 50 ppm, about 10 ppm to about 50 ppm, about 15 ppm to about 50 ppm, about 20 ppm to about 50 ppm, about 25 ppm to about 50 ppm, about 30 ppm to about 50 ppm, about 35 ppm to about 50 ppm, about 40 ppm to about 50 ppm, about 45 ppm to about 50 ppm, about 5 ppm to about 60 ppm, about 10 ppm to about 60 ppm, about 15 ppm to about 60 ppm, about 20 ppm to about 60 ppm, about 25 ppm to about 60 ppm, about 30 ppm to about 60 ppm, about 35 ppm to about 60 ppm, about 40 ppm to about 60 ppm, about 45 ppm to about 60 ppm, about 50 ppm to about 60 ppm, about 55 ppm to about 60 ppm, about 5 ppm to about 70 ppm, about 10 ppm to about 70 ppm, about 15 ppm to about 70 ppm, about 20 ppm to about 70 ppm, about 25 ppm to about 70 ppm, about 30 ppm to about 70 ppm, about 35 ppm to about 70 ppm, about 40 ppm to about 70 ppm, about 45 ppm to about 70 ppm, about 50 ppm to about 70 ppm, about 55 ppm to about 70 ppm, about 60 ppm to about 70 ppm, about 65 ppm to about 70 ppm, about 5 ppm to about 80 ppm, about 10 ppm to about 80 ppm, about 15 ppm to about 80 ppm, about 20 ppm to about 80 ppm, about 25 ppm to about 80 ppm, about 30 ppm to about 80 ppm, about 35 ppm to about 80 ppm, about 40 ppm to about 80 ppm, about 45 ppm to about 80 ppm, about 50 ppm to about 80 ppm, about 55 ppm to about 80 ppm, about 60 ppm to about 80 ppm, about 65 ppm to about 80 ppm, about 70 ppm to about 80 ppm, about 75 ppm to about 80 ppm, about 5 ppm to about 90 ppm, about 10 ppm to about 90 ppm, about 15 ppm to about 90 ppm, about 20 ppm to about 90 ppm, about 25 ppm to about 90 ppm, about 30 ppm to about 90 ppm, about 35 ppm to about 90 ppm, about 40 ppm to about 90 ppm, about 45 ppm to about 90 ppm, about 50 ppm to about 90 ppm, about 55 ppm to about 90 ppm, about 60 ppm to about 90 ppm, about 65 ppm to about 90 ppm, about 70 ppm to about 90 ppm, about 75 ppm to about 90 ppm, about 80 ppm to about 90 ppm, about 85 ppm to about 90 ppm, about 5 ppm to about 100 ppm, about 10 ppm to about 100 ppm, about 15 ppm to about 100 ppm, about 20 ppm to about 100 ppm, about 25 ppm to about 100 ppm, about 30 ppm to about 100 ppm, about 35 ppm to about 100 ppm, about 40 ppm to about 100 ppm, about 45 ppm to about 100 ppm, about 50 ppm to about 100 ppm, about 55 ppm to about 100 ppm, about 60 ppm to about 100 ppm, about 65 ppm to about 100 ppm, about 70 ppm to about 100 ppm, about 75 ppm to about 100 ppm, about 80 ppm to about 100 ppm, about 85 ppm to about 100 ppm, about 90 ppm to about 100 ppm, about 95 ppm to about 100 ppm, and ranges between about 0.1 ppm to about 100 ppm. In certain aspects, the amount of cathepsin D is quantified using an immunoassay or a mass spectrometry assay. In some specific aspects, the immunoassay is a cathepsin D ELISA. In certain aspects, the mass spectrometry assay is LC-MS/MS and ranges between about 0.1 ppm to about 20 ppm. In certain aspects, the amount of cathepsin D is quantified using an immunoassay or a mass spectrometry assay. In certain aspects, the immunoassay is a total Chinese hamster ovary protein ELISA or a cathepsin D ELISA. In certain aspects, the mass spectrometry assay is LC-MS/MS.

Prior to forming a drug substance intermediate, the preparation can be purified by a variety of steps. For example, the preparation can be purified by Protein A chromatography, anion exchange chromatography, cation exchange chromatography, hydrophobic interaction chromatography, or a combination of two or more thereof.

For example, in one aspect, a clarified harvest sample preparation from a culture comprising the anti-VEGF protein is subjected to a capture chromatography procedure. In one aspect, the capture step is an affinity chromatography procedure using, for example, Protein A.

In one aspect, aflibercept is produced from a host cell genetically engineered to express the anti-VEGF protein. In one aspect, other species or variants of the anti-VEGF protein are also produced.

In one aspect, the preparation includes an aspartic acid protease inhibitor. In a specific aspect, the aspartic acid protease inhibitor is pepstatin A.

In one aspect, the cell culture medium includes a cathepsin D inhibitor.

In one aspect, the pH of the cell culture medium is more than about 6.0. In one specific aspect, the pH is about 6.0 to about 6.8. In another specific aspect, the pH is between about 6.1 to about 6.8, about 6.2 to about 6.8, about 6.3 to about 6.8, about 6.4 to about 6.8, about 6.5 to about 6.8, about 6.6 to about 6.8, about 6.7 to about 6.8, about 6.1 to about 6.7, about 6.2 to about 6.7, about 6.3 to about 6.7, about 6.4 to about 6.7, about 6.5 to about 6.7, about 6.6 to about 6.7, about 6.1 to about 6.6, about 6.2 to about 6.6, about 6.3 to about 6.6, about 6.4 to about 6.6, about 6.5 to about 6.6, about 6.1 to about 6.5, about 6.2 to about 6.5, about 6.3 to about 6.5, about 6.4 to about 6.5, about 6.1 to about 6.4, about 6.2 to about 6.4, about 6.3 to about 6.4, about 6.1 to about 6.3, about 6.2 to about 6.3, about 6.1 to about 6.2 and any range between the preceding amounts.

In one aspect, the cell culture medium includes a buffer. In a specific aspect, the buffer is sodium citrate.

In one aspect, the culturing is carried out at a temperature from about 30° C. to about 40° C. In a specific aspect, the culturing is carried out at a temperature of about 35° C.

In one aspect, the culturing is performed for about 7-12 days. In a specific aspect, the culturing is performed for about 8 days.

In one aspect, the preparation includes a truncated aflibercept is formed by clipping at one or more of the following sites of aflibercept: N99T100, T94H95, T90N91, and Y92/L93 In another aspect, the truncated aflibercept is formed by clipping at Y92L93 of aflibercept.

In one aspect, the amount of truncated aflibercept present in the preparation is less than about 10%. In some embodiments, the amount of truncated aflibercept present in the preparation is less than about 9%, less than about 8%, less than about 7%, less than about 6%, less than about 5%, less than about 4%, less than about 3%, less than about 2%, less than about 1%, less than about 0.5%, less than about 0.1%, and ranges between about 0.1% to about 10%.

In one embodiment, the clarified harvest sample from harvesting a preparation is subjected to a capture step such as Protein A affinity chromatography. Subsequent to the affinity step, an affinity eluate can be subjected to ion exchange chromatography. The ion exchange chromatography can be either cation or anion exchange chromatography. Also contemplated to be within the scope of the present embodiment is mixed-mode or multimodal chromatography as well as other chromatographic procedures which are discussed further below. In a particular aspect, the ion exchange chromatography is anion exchange chromatography (AEX). Suitable conditions for employing AEX include, but are not limited to, tris hydrochloride at a pH of about 8.3 to about 8.6. Following equilibration using, for example, tris hydrochloride at a pH of about 8.3 to about 8.6, the AEX column is loaded with sample. Following the loading of the column, the column can be washed one or multiple times using, for example, an equilibrating buffer. In a particular aspect, the conditions used can facilitate the differential chromatographic behavior of aflibercept and its oxidized variants such that a fraction comprising aflibercept absent significant amounts of oxo-variants can be collected in a flowthrough fraction while a significant portion of oxo-variants are retained on the solid-phase of the AEX column and can be obtained upon stripping the column.

The present embodiment can include the addition of one or more steps, in no particular order, such as hydrophobic interaction chromatography (HIC), affinity chromatography, multimodal chromatography, viral inactivation (e.g., using low pH), viral filtration, and/or ultra/diafiltration as well as other well-known chromatographic steps.

In one embodiment, the anti-VEGF protein is glycosylated at one or more asparagines, not limited to G0-GlcNAc glycosylation; G1-GlcNAc glycosylation: G1S-GlcNAc glycosylation; G0 glycosylation; G1 glycosylation; G1S glycosylation: G2 glycosylation; G2S glycosylation: G2S2 glycosylation; GOF glycosylation; G2F2S glycosylation; G2F2S2 glycosylation; G1F glycosylation; G1FS glycosylation; G2F glycosylation; G2FS glycosylation; G2FS2 glycosylation; G3FS glycosylation: G3FS3 glycosylation: G0-2GlcNAc glycosylation; Man4 glycosylation; Man4_A1G1 glycosylation: Man4_A1G1S1 glycosylation; Man5 glycosylation: Man5_A1G1 glycosylation; Man5_A1G1S1 glycosylation; Man6 glycosylation; Man6_G0+Phosphate glycosylation: Man6+Phosphate glycosylation; and/or Man7 glycosylation. In one aspect, the anti-VEGF protein can be aflibercept, or VEGF MiniTrap.

In one embodiment, the process can further comprise formulating a drug substance using a pharmaceutically acceptable excipient. In one aspect of the embodiment, the pharmaceutically acceptable excipient can be selected from one or more of the following: water, buffering agents, sugar, salt, surfactant, amino acid, polyol, chelating agent, emulsifier and preservative. Other well-known excipients to the skilled artisan are within the purview of this embodiment.

In one aspect of the embodiment, the formulation can be suitable for administration to a human subject. In particular, administration can be affected by intravitreal injection. In one aspect, the formulation can have about 10 to about 30) mg/mL of the anti-VEGF protein. In one particular aspect, the formulation can have anti-VEGF at a concentration of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 ng/mL, about 0.9 mg/mL, about 1 ng/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL about 190 mg/mL, about 200 mg/mL, about 225 ng/mL, about 250 mg/mL, about 275 mg/mL, about 300 mg/mL, and ranged between the preceding amounts.

The formulation can be used as a method of treating or preventing angiogenic eye disorders which can include, for example: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; or diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

Production of Truncated Aflibercept

In another implementation, the present disclosure describes the production of modified versions of aflibercept wherein the aflibercept is truncated. This can be produced in any cell culture medium including a chemically defined medium (CDM) or soy hydrolysate medium.

In yet another embodiment, the cell culture medium is a chemically-defined medium supplemented with a hydrolysate.

In one aspect, the cell culture medium comprises chemically defined medium. In some specific aspects, the cell culture medium can be supplemented with one of more of the following: a recombinant growth factor; a buffer; an osmolarity regulator; an energy source; and hydrolysate(s). The hydrolysates can be an additional source of free amino acids along with di- and tri-peptides and can be supplemented to the cell culture medium. In one embodiment, the method for producing a truncated aflibercept comprises culturing a mammalian cell producing aflibercept in a cell culture medium, wherein the cell culture medium has a pH of about 2 to about 6; and harvesting a preparation of the truncated aflibercept produced by the mammalian cell.

In one aspect, the preparation includes a truncated aflibercept.

In one aspect, the amount of truncated aflibercept present in the preparation is less than about 10%. In some embodiments, the amount of truncated aflibercept present in the preparation is less than about 9%, less than about 8%, less than about 7%, less than about 6%, less than about 5%, less than about 4%, less than about 3%, less than about 2%, less than about 1%, less than about 0.5%, less than about 0.1%, and ranges between about 0.1% to about 10%.

In one aspect, the truncated aflibercept is formed by clipping at one or more of the following sites of aflibercept: N99T100, T94H95, T90N91, and Y92/L93 In another aspect, the truncated aflibercept is formed by clipping at Y92L93 of aflibercept.

In one aspect, the pH is between about 2 and about 5. In one aspect, the pH is between about 4 and about 5. In a specific aspect, the pH is between about 4.25 and about 4.75.

In one aspect, the preparation has less than about 100 ppm of aspartic protease. In certain embodiments, the amount of aspartic protease is between 0.5 ppm to about 100 ppm, 0.5 ppm to about 90 ppm, 0.5 ppm to about 80 ppm, 0.5 ppm to about 70 ppm, 0.5 ppm to about 60 ppm, 0.5 ppm to about 50 ppm, 0.5 ppm to about 40 ppm, 0.5 ppm to about 30 ppm, 0.5 ppm and 20 ppm, or between 0.5 ppm and 15 ppm, or between 0.5 ppm and 10 ppm, or between 0.5 ppm and 8 ppm, or between 0.5 ppm and 5 ppm, or between 0.5 ppm and 3 ppm, or between 0.5 ppm and 2 ppm, or between 0.5 ppm and 1 ppm, or between the limit of assay quantitation (LOQ) and 1 ppm. In a specific aspect, the aspartic protease is cathepsin D.

In another aspect, the preparation has an amount of aspartic protease between about 0.1 ppm to about 10 ppm. In certain embodiments, the amount of aspartic protease is between, about 0.1 ppm to about 0.5 ppm, about 0.1 ppm to about 1 ppm, about 0.1 ppm to about 1 ppm, about 0.1 ppm to about 5 ppm, about 0.1 ppm to about 10 ppm, about 0.1 ppm to about 15 ppm, about 0.1 ppm to about 20 ppm, about 0.5 ppm to about 1 ppm, about 0.1 ppm to about 5 ppm, about 0.1 ppm to about 10 ppm, about 0.1 ppm to about 15 ppm, about 0.1 ppm to about 20 ppm, about 5 ppm to about 10 ppm, about 5 ppm to about 15 ppm, about 5 ppm to about 20 ppm, about 10 ppm to about 15 ppm, about 10 ppm to about 20 ppm, about 15 ppm to about 20 ppm, about 5 ppm to about 30 ppm, about 10 ppm to about 30 ppm, about 15 ppm to about 30 ppm, about 20 ppm to about 30 ppm, about 25 ppm to about 30 ppm, about 5 ppm to about 40 ppm, about 10 ppm to about 40 ppm, about 15 ppm to about 40 ppm, about 20 ppm to about 40 ppm, about 25 ppm to about 40 ppm, about 30 ppm to about 40 ppm, about 35 ppm to about 40 ppm, about 5 ppm to about 50 ppm, about 10 ppm to about 50 ppm, about 15 ppm to about 50 ppm, about 20 ppm to about 50 ppm, about 25 ppm to about 50 ppm, about 30 ppm to about 50 ppm, about 35 ppm to about 50 ppm, about 40 ppm to about 50 ppm, about 45 ppm to about 50 ppm, about 5 ppm to about 60 ppm, about 10 ppm to about 60 ppm, about 15 ppm to about 60 ppm, about 20 ppm to about 60 ppm, about 25 ppm to about 60 ppm, about 30 ppm to about 60 ppm, about 35 ppm to about 60 ppm, about 40 ppm to about 60 ppm, about 45 ppm to about 60 ppm, about 50 ppm to about 60 ppm, about 55 ppm to about 60 ppm, about 5 ppm to about 70 ppm, about 10 ppm to about 70 ppm, about 15 ppm to about 70 ppm, about 20 ppm to about 70 ppm, about 25 ppm to about 70 ppm, about 30 ppm to about 70 ppm, about 35 ppm to about 70 ppm, about 40 ppm to about 70 ppm, about 45 ppm to about 70 ppm, about 50 ppm to about 70 ppm, about 55 ppm to about 70 ppm, about 60 ppm to about 70 ppm, about 65 ppm to about 70 ppm, about 5 ppm to about 80 ppm, about 10 ppm to about 80 ppm, about 15 ppm to about 80 ppm, about 20 ppm to about 80 ppm, about 25 ppm to about 80 ppm, about 30 ppm to about 80 ppm, about 35 ppm to about 80 ppm, about 40 ppm to about 80 ppm, about 45 ppm to about 80 ppm, about 50 ppm to about 80 ppm, about 55 ppm to about 80 ppm, about 60 ppm to about 80 ppm, about 65 ppm to about 80 ppm, about 70 ppm to about 80 ppm, about 75 ppm to about 80 ppm, about 5 ppm to about 90 ppm, about 10 ppm to about 90 ppm, about 15 ppm to about 90 ppm, about 20 ppm to about 90 ppm, about 25 ppm to about 90 ppm, about 30 ppm to about 90 ppm, about 35 ppm to about 90 ppm, about 40 ppm to about 90 ppm, about 45 ppm to about 90 ppm, about 50 ppm to about 90 ppm, about 55 ppm to about 90 ppm, about 60 ppm to about 90 ppm, about 65 ppm to about 90 ppm, about 70 ppm to about 90 ppm, about 75 ppm to about 90 ppm, about 80 ppm to about 90 ppm, about 85 ppm to about 90 ppm, about 5 ppm to about 100 ppm, about 10 ppm to about 100 ppm, about 15 ppm to about 100 ppm, about 20 ppm to about 100 ppm, about 25 ppm to about 100 ppm, about 30 ppm to about 100 ppm, about 35 ppm to about 100 ppm, about 40 ppm to about 100 ppm, about 45 ppm to about 100 ppm, about 50 ppm to about 100 ppm, about 55 ppm to about 100 ppm, about 60 ppm to about 100 ppm, about 65 ppm to about 100 ppm, about 70 ppm to about 100 ppm, about 75 ppm to about 100 ppm, about 80 ppm to about 100 ppm, about 85 ppm to about 100 ppm, about 90 ppm to about 100 ppm, about 95 ppm to about 100 ppm, and ranges between about 0.1 ppm to about 100 ppm. In a specific aspect, the aspartic protease is Cathepsin D.

In one aspect, the culturing is carried out at a temperature from about 35° C. to about 37° C. In a specific aspect, the culturing is carried out at a temperature of about 35° C.

In one aspect, the culturing is performed for 7-12 days. In a specific aspect, the culturing is performed for 8 days.

In one aspect of the present embodiment, the aflibercept is expressed in a suitable host cell. Non-limiting examples of such host cells include, but are not limited to, CHO. CHO K1, EESYR®, NICE®, NS0, Sp2/0, embryonic kidney cells and BHK.

Suitable CDMs include Dulbecco's Modified Eagle's (DME) medium, Ham's Nutrient Mixture, EX-CELL medium (SAFC), and IS CHO-CD medium (Irvine). Other CDMs known to those skilled in the art are also contemplated to be within the scope of the present disclosure. In a particular aspect, a suitable CDM is CDM1B (Regeneron) or Excell medium (SAFC).

The present embodiment can include the addition of one or more steps, in no particular order, such as hydrophobic interaction chromatography, affinity chromatography, multimodal chromatography, viral inactivation (e.g., using low pH), viral filtration, and/or ultra/diafiltration.

In one embodiment, the process can further comprise formulating the modified version of aflibercept using a pharmaceutically acceptable excipient. In one aspect, the pharmaceutically acceptable excipient can be selected from one or more of the following: water, buffering agents, sugar, salt, surfactant, amino acid, polyol, chelating agent, emulsifier and preservative. Other well-known excipients to the skilled artisan are within the purview of this embodiment.

The formulation of the present disclosure is suitable for administration to a human subject. In one aspect of the present embodiment, administration can be affected by intravitreal injection. In one aspect, the formulation can have about 40 to about 200 mg/mL of the modified version of aflibercept.

The formulation can be used in a method of treating or preventing angiogenic eye disorders which can include, for example: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; or diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

Methods to Minimize Cathepsin D

The present disclosure also provides methods for purification of a VEGF receptor fusion protein such as aflibercept sample to reduce levels of certain host cell proteins, such as aspartyl protease, e.g., cathepsin D. The method can include harvesting a preparation of aflibercept, wherein the preparation contains an aspartic protease and subjecting the preparation to a size exclusion chromatography column, where the size exclusion chromatography column includes at least about 1000 plates of 100 cm thickness and the size exclusion chromatography column provides fractions including the aflibercept and fractions including the aspartic protease inhibitor, thereby purifying the aflibercept sample.

In some embodiments, the preparation includes a truncated aflibercept.

In some embodiments, the aspartic protease is cathepsin D.

In some embodiments, the pH of the aflibercept sample is about 6.3 to about 6.6.

In some embodiments, a surfactant is added to the aflibercept sample prior to subjecting it to the size exclusion chromatography column. In specific embodiments, the surfactant is polysorbate 20.

In some embodiments, the method further comprises use of at least one other chromatography selected from the group consisting of anion exchange chromatography, cation exchange chromatography, and hydrophobic interaction chromatography.

In some embodiments, the size exclusion chromatography column includes at about 1000 to about 1500 plates. In other embodiments, the size exclusion chromatography column includes at least about 1100 plates.

Methods to Quantify Cathepsin D

The present disclosure also provides methods for quantitative measurement of aspartyl protease, e.g., cathepsin D in a sample. The method can include, for example, obtaining isolated an antibody specific for a protein with an amino acid sequence comprising an amino acid sequence of aspartyl protease, e.g., cathepsin D; attaching said isolated antibody to a solid support; reacting attached isolated antibody with said sample including the aspartyl protease, e.g., cathepsin D; providing a detector capable of recognizing an amino acid sequence which is separate and distinct from the amino acid sequence recognized by the attached isolated antibody; effecting an immunoreaction; and detecting said immunoreaction to quantitatively measure the aspartyl protease, e.g., cathepsin D, in the sample.

In some embodiments, the isolated antibody is a polyclonal antibody. In another embodiments, the isolated antibody is a monoclonal antibody. The isolated antibody can be obtained from any animal, for example, the animal can be a rabbit or a goat.

In some embodiments, the isolated antibody is obtained by immunizing an animal to the protein with an amino acid sequence comprising an amino acid sequence of aspartyl protease, e.g., cathepsin D, to obtain serum from the animal: contacting the serum to a chromatography column including the aspartyl protease, e.g., cathepsin D; and collecting an eluate from the chromatography including the isolated antibody.

In some embodiments, the protein with the amino acid sequence comprising the amino acid sequence of aspartyl protease, e.g., cathepsin D, comprises a mmh tag.

In some embodiments, the isolated antibody is obtained by immunizing an animal to the protein with an amino acid sequence comprising an amino acid sequence of aspartyl protease, e.g., cathepsin D to obtain serum from the animal: contacting the serum to a chromatography column including cathepsin D; and collecting an eluate from the chromatography including the isolated antibody. In such cases, the method can comprise contacting the eluate from the chromatography including the isolated antibody to a second chromatography column including anti-mmh antibodies and collecting the flowthrough including the isolated antibody.

VEGF Receptor Fusion Protein, e.g., Aflibercept, Composition

The present disclosure also provides aflibercept composition comprising aflibercept isolated from CHO cells, wherein the composition comprises the aflibercept and a residual amount of an aspartic protease.

In some embodiments, the aflibercept composition can be prepared by culturing a mammalian cell producing aflibercept in a cell culture medium, wherein the cell culture medium has a pH of about 2 to about 6.8. This can be produced in any cell culture medium including a chemically defined medium (CDM) or soy hydrolysate medium. The cell culture medium can also be chemically-defined medium supplemented with a hydrolysate. The cell culture medium can also be supplemented with one of more of the following: a recombinant growth factor; a buffer; an osmolarity regulator; an energy source; and hydrolysate(s). The hydrolysates can be an additional source of free amino acids along with di- and tri-peptides and can be supplemented to the cell culture medium.

Non-limiting examples of such host cells include, but are not limited to, CHO, CHO K1, EESYR®, NICE®, NS0, Sp2/0, embryonic kidney cells and BHK. Suitable CDMs include Dulbecco's Modified Eagle's (DME) medium, Ham's Nutrient Mixture, EX-CELL medium (SAFC), and IS CHO-CD medium (Irvine). Other CDMs known to those skilled in the art are also contemplated to be within the scope of the present disclosure. In a particular aspect, a suitable CDM is CDM1B (Regeneron) or Excell medium (SAFC).

In certain embodiments, the amount of the aspartic protease is less than about 100 ppm. In certain embodiments, the amount of the aspartic protease is less than about 1 ppm. In certain embodiments, the amount of cathepsin D is between 0.5 ppm to about 100 ppm, 0.5 ppm to about 90 ppm, 0.5 ppm to about 80 ppm, 0.5 ppm to about 70 ppm, 0.5 ppm to about 60 ppm, 0.5 ppm to about 50 ppm, 0.5 ppm to about 40 ppm, 0.5 ppm to about 30 ppm, 0.5 ppm and 20 ppm, or between 0.5 ppm and 15 ppm, or between 0.5 ppm and 10 ppm, or between 0.5 ppm and 8 ppm, or between 0.5 ppm and 5 ppm, or between 0.5 ppm and 3 ppm, or between 0.5 ppm and 2 ppm, or between 0.5 ppm and 1 ppm, or between the limit of assay quantitation (LOQ) and 1 ppm. In one specific aspect, the aspartic protease is cathepsin D.

In some embodiments, the amount of the aspartic protease in the composition is between about 0.1 ppm to about 100 ppm. In certain embodiments, the aspartic protease is between, about 0.1 ppm to about 0.5 ppm, about 0.1 ppm to about 1 ppm, about 0.1 ppm to about 1 ppm, about 0.1 ppm to about 5 ppm, about 0.1 ppm to about 10 ppm, about 0.1 ppm to about 15 ppm, about 0.1 ppm to about 20 ppm, about 0.5 ppm to about 1 ppm, about 0.1 ppm to about 5 ppm, about 0.1 ppm to about 10 ppm, about 0.1 ppm to about 15 ppm, about 0.1 ppm to about 20 ppm, about 5 ppm to about 10 ppm, about 5 ppm to about 15 ppm, about 5 ppm to about 20 ppm, about 10 ppm to about 15 ppm, about 10 ppm to about 20 ppm, about 15 ppm to about 20 ppm, about 5 ppm to about 30 ppm, about 10 ppm to about 30 ppm, about 15 ppm to about 30 ppm, about 20 ppm to about 30 ppm, about 25 ppm to about 30 ppm, about 5 ppm to about 40 ppm, about 10 ppm to about 40 ppm, about 15 ppm to about 40 ppm, about 20 ppm to about 40 ppm, about 25 ppm to about 40 ppm, about 30 ppm to about 40 ppm, about 35 ppm to about 40 ppm, about 5 ppm to about 50 ppm, about 10 ppm to about 50 ppm, about 15 ppm to about 50 ppm, about 20 ppm to about 50 ppm, about 25 ppm to about 50 ppm, about 30 ppm to about 50 ppm, about 35 ppm to about 50 ppm, about 40 ppm to about 50 ppm, about 45 ppm to about 50 ppm, about 5 ppm to about 60 ppm, about 10 ppm to about 60 ppm, about 15 ppm to about 60 ppm, about 20 ppm to about 60 ppm, about 25 ppm to about 60 ppm, about 30 ppm to about 60 ppm, about 35 ppm to about 60 ppm, about 40 ppm to about 60 ppm, about 45 ppm to about 60 ppm, about 50 ppm to about 60 ppm, about 55 ppm to about 60 ppm, about 5 ppm to about 70 ppm, about 10 ppm to about 70 ppm, about 15 ppm to about 70 ppm, about 20 ppm to about 70 ppm, about 25 ppm to about 70 ppm, about 30 ppm to about 70 ppm, about 35 ppm to about 70 ppm, about 40 ppm to about 70 ppm, about 45 ppm to about 70 ppm, about 50 ppm to about 70 ppm, about 55 ppm to about 70 ppm, about 60 ppm to about 70 ppm, about 65 ppm to about 70 ppm, about 5 ppm to about 80 ppm, about 10 ppm to about 80 ppm, about 15 ppm to about 80 ppm, about 20 ppm to about 80 ppm, about 25 ppm to about 80 ppm, about 30 ppm to about 80 ppm, about 35 ppm to about 80 ppm, about 40 ppm to about 80 ppm, about 45 ppm to about 80 ppm, about 50 ppm to about 80 ppm, about 55 ppm to about 80 ppm, about 60 ppm to about 80 ppm, about 65 ppm to about 80 ppm, about 70 ppm to about 80 ppm, about 75 ppm to about 80 ppm, about 5 ppm to about 90 ppm, about 10 ppm to about 90 ppm, about 15 ppm to about 90 ppm, about 20 ppm to about 90 ppm, about 25 ppm to about 90 ppm, about 30 ppm to about 90 ppm, about 35 ppm to about 90 ppm, about 40 ppm to about 90 ppm, about 45 ppm to about 90 ppm, about 50 ppm to about 90 ppm, about 55 ppm to about 90 ppm, about 60 ppm to about 90 ppm, about 65 ppm to about 90 ppm, about 70 ppm to about 90 ppm, about 75 ppm to about 90 ppm, about 80 ppm to about 90 ppm, about 85 ppm to about 90 ppm, about 5 ppm to about 100 ppm, about 10 ppm to about 100 ppm, about 15 ppm to about 100 ppm, about 20 ppm to about 100 ppm, about 25 ppm to about 100 ppm, about 30 ppm to about 100 ppm, about 35 ppm to about 100 ppm, about 40 ppm to about 100 ppm, about 45 ppm to about 100 ppm, about 50 ppm to about 100 ppm, about 55 ppm to about 100 ppm, about 60 ppm to about 100 ppm, about 65 ppm to about 100 ppm, about 70 ppm to about 100 ppm, about 75 ppm to about 100 ppm, about 80 ppm to about 100 ppm, about 85 ppm to about 100 ppm, about 90 ppm to about 100 ppm, about 95 ppm to about 100 ppm, and ranges between about 0.1 ppm to about 100 ppm. In one specific aspect, the aspartic protease is cathepsin D.

In one embodiment, the composition of formulation can include a pharmaceutically acceptable excipient. In one aspect, the pharmaceutically acceptable excipient can be selected from the following: water, buffering agents, sugar, salt, surfactant, amino acid, polyol, chelating agent, emulsifier and preservative. Other well-known excipients to the skilled artisan are within the purview of this embodiment.

The composition of the present disclosure is suitable for administration to a human subject. In one aspect of the present embodiment, administration can be affected by intravitreal injection. In one aspect, the formulation can have about 40 to about 200 mg/mL of the modified version of aflibercept.

The composition can be used in a method of treating or preventing angiogenic eye disorders which can include: age-related macular degeneration (e.g., wet or dry), macular edema, macular edema following retinal vein occlusion, retinal vein occlusion (RVO), central retinal vein occlusion (CRVO), branch retinal vein occlusion (BRVO), diabetic macular edema (DME), choroidal neovascularization (CNV), iris neovascularization, neovascular glaucoma, post-surgical fibrosis in glaucoma, proliferative vitreoretinopathy (PVR), optic disc neovascularization, corneal neovascularization, retinal neovascularization, vitreal neovascularization, pannus, pterygium, vascular retinopathy, diabetic retinopathy in a subject with diabetic macular edema; or diabetic retinopathies (e.g., non-proliferative diabetic retinopathy (e.g., characterized by a Diabetic Retinopathy Severity Scale (DRSS) level of about 47 or 53) or proliferative diabetic retinopathy; e.g., in a subject that does not suffer from DME).

In some embodiments, the composition further comprises a truncated aflibercept. In one aspect, the truncated aflibercept is formed by clipping at Y92/L93 of aflibercept.

In one aspect, the amount of truncated aflibercept present in the aflibercept composition is less than about 10%. In some embodiments, the amount of truncated aflibercept present in the aflibercept composition is less than about 9%, less than about 8%, less than about 7%, less than about 6%, less than about 5%, less than about 4%, less than about 3%, less than about 2%, less than about 1%, less than about 0.5%, less than about 0.1%, and ranges between about 0.1% to about 10%.

In one aspect, the amount of truncated aflibercept present in the aflibercept composition is between about 0.1% to about 10%. In some embodiments, the amount of truncated aflibercept present in the aflibercept composition is between about 0.1% to about 1%, about 0.1% to about 2%, about 0.1% to about 3%, about 0.1% to about 4%, about 0.1% to about 5%, about 0.1% to about 6%, about 0.1% to about 7%, about 0.1% to about 8%, about 0.1% to about 9%, about 0.1% to about 10%, about 0.5% to about 1%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 9%, about 0.5% to about 10%, about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 2% to about 3%, about 2% to about 4%, about 2% to about 5%, about 2% to about 6%, about 2% to about 7%, about 2% to about 8%, about 2% to about 9%, about 2% to about 10%, about 3% to about 4%, about 3% to about 5%, about 3% to about 6%, about 3% to about 7%, about 3% to about 8%, about 3% to about 9%, about 3% to about 10%, about 4% to about 5%, about 4% to about 6%, about 4% to about 7%, about 4% to about 8%, about 4% to about 9%, about 4% to about 10%, about 5% to about 6%, about 5% to about 7%, about 5% to about 8%, about 5% to about 9%, about 5% to about 10%, about 6% to about 7%, about 6% to about 8%, about 6% to about 9%, about 6% to about 10%, about 7% to about 8%, about 7% to about 9%, about 7% to about 10%, about 8% to about 9%, about 9% to about 10%, and ranges between.

VEGF Receptor Fusion Protein, e.g., Aflibercept, Formulation

As described above, a drug substance intermediate can be purified by an SEC column and an eluate collected having a VEGF receptor fusion protein and a low amount of an aspartyl protease. One or more of the collected eluates can be further processed to a formulated drug product, e.g., including one or more steps of concentrating, filtering, and/or formulating the collected eluate(s) with one or more pharmaceutically acceptable excipients. Formulations of the present disclosure are suitable for a high concentration of the VEGF receptor fusion protein, e.g., aflibercept, such as a concentration of at least 41 mg/mL of the VEGF receptor fusion protein in the formulation. As described earlier when referring to formulations, the concentration of the VEGF receptor fusion protein, e.g., aflibercept, in a formulation can range from about 100 mg/mL to about 300 mg/mL. The pH of the formulation can range from about 5.0 to about 6.5, such as from about 5.5 to about 6.1.

Advantageously, formulations of the present disclosure can have a low amount of an aspartyl protease (e.g., cathepsin D) such as less than 1 ppm, e.g., less than 0.7 ppm, 0.5 ppm, 0.3 ppm, 0.1 ppm, 0.1 ppm, 0.07 ppm, 0.05 ppm, etc. of the aspartyl protease (e.g., cathepsin D) in the formulation.

In an aspect, the pharmaceutically acceptable excipient can be selected from the following: water, buffering agents, a sugar, a salt, a surfactant, an amino acid, a polyol, a chelating agent, an emulsifier, a preservative, or a combination of two or more thereof.

The formulations of the present disclosure can be introduced into a vessel or device e.g., a vial, or delivery device, e.g., a pre-filled syringe. The formulations of the present disclosure are suitable for administration to a human subject. In one aspect of the present embodiment, administration can be affected by intravitreal injection.

EMBODIMENTS

The following list of embodiments is intended to complement, rather than displace or supersede, the previous descriptions.

Embodiments Set I

Embodiment I-1. A composition of aflibercept isolated from Chinese hamster ovary host cells, the composition comprising:
- aflibercept and a residual amount of an aspartic protease; and
- wherein the residual amount of the aspartic protease is between about 0.1 ppm to about 100 ppm.

Embodiment I-2. The composition of embodiment 1, wherein the aspartic protease is cathepsin D.

Embodiment I-3. The composition of any of the preceding embodiments, wherein the residual amount of cathepsin D is quantified using an immunoassay or a mass spectrometry assay.

Embodiment I-4. The composition of any of the preceding embodiments, wherein the immunoassay is cathepsin D ELISA.

Embodiment I-5. The composition of any of the preceding embodiments, wherein the mass spectrometry assay is LC-MS/MS.

Embodiment I-6. The composition of any of the preceding embodiments, further comprising truncated aflibercept.

Embodiment I-7. The composition of any of the preceding embodiments, wherein amount of truncated aflibercept is less than about 5%.

Embodiment I-8. The composition of any of the preceding embodiments, wherein amount of truncated aflibercept is less than about 4%.

Embodiment I-9. The composition of any of the preceding embodiments, wherein amount of truncated aflibercept is less than about 3%.

Embodiment I-10. The composition of any of the preceding embodiments, wherein amount of truncated aflibercept is less than about 2%.

Embodiment I-11. The composition of any of the preceding embodiments, wherein amount of truncated aflibercept is less than about 1%.

Embodiment I-12. The composition of any of the preceding embodiments, wherein amount of truncated aflibercept is less than about 0.5%.

Embodiment I-13.

Embodiment I-14. The composition of any of the preceding embodiments, wherein the truncated aflibercept is formed by truncating aflibercept between Tyrosine residue at 92 position and Leucine at 93 position.

Embodiment I-15. A method for producing aflibercept, the method comprising:
- providing a host cell genetically engineered to express aflibercept;
- culturing the host cell in a cell culture medium, wherein the cell culture medium has a pH between about 6 to about 6.8; and
- harvesting a preparation of the aflibercept produced by the cell.

Embodiment I-16. The method of embodiment 15, wherein the cell culture medium includes an aspartic protease inhibitor.

Embodiment I-17. The method of embodiment 16, wherein the aspartic acid protease inhibitor is pepstatin A.

Embodiment I-18. The method of embodiment 15, wherein the preparation includes a cathepsin D inhibitor.

Embodiment I-19. The method of embodiment 15, wherein the pH is about 6.3 to about 6.6.

Embodiment I-20. The method of embodiment 15, wherein the cell culture medium includes a buffer.

Embodiment I-21. The method of embodiment 20, wherein the buffer is sodium citrate.

Embodiment I-22. The method of embodiment 15, wherein the culturing is carried out at a temperature from about 30° C. to about 40° C.

Embodiment I-23. The method of embodiment 22, wherein the culturing is carried out at a temperature of about 35° C.

Embodiment I-24. The method of embodiment 15, wherein the culturing is performed for about 7-12 days.

Embodiment I-25. The method of embodiment 15, wherein the culturing is performed for about 8 days.

Embodiment I-26. The method of embodiment 15, wherein the preparation includes truncated aflibercept.

Embodiment I-27. The method of embodiment 26, wherein amount of truncated aflibercept is less than about 5%.

Embodiment I-28. The method of embodiment 26, wherein amount of truncated aflibercept is less than about 4%.

Embodiment I-29. The method of embodiment 26, wherein amount of truncated aflibercept is less than about 3%.

Embodiment I-30. The method of embodiment 26, wherein amount of truncated aflibercept is less than about 2%.

Embodiment I-31. The method of embodiment 26, wherein amount of truncated aflibercept is less than about 1%.

Embodiment I-32. The method of embodiment 26, wherein amount of truncated aflibercept is less than about 0.5%.

Embodiment I-33. The method of embodiment 26, wherein amount of truncated aflibercept is less than about 5%.

Embodiment I-34.

Embodiment I-35. A method for producing aflibercept, the method comprising:
- providing a host cell genetically engineered to express aflibercept;
- culturing the host cell in a cell culture medium, wherein the cell culture medium has a pH greater than about 6; and
- harvesting a preparation of the aflibercept produced by the cell, wherein the preparation contains an aspartic protease inhibitor.

Embodiment I-36. The method of embodiment 35, wherein the preparation includes truncated aflibercept.

Embodiment I-37. A method for producing a truncated aflibercept, said method comprising:
- culturing a mammalian cell producing aflibercept in a cell culture medium, wherein the cell culture medium has a pH of about 2 to about 6; and
- harvesting a preparation of the truncated aflibercept produced by the mammalian cell.

Embodiment I-38. The method of embodiment 36, wherein the preparation includes aflibercept.

Embodiment I-39. The method of embodiment 36, wherein the pH is between 2 and 5.

Embodiment I-40. The method of embodiment 36, wherein the preparation includes an aspartic protease.

Embodiment I-41. The method of embodiment 39, wherein the aspartic protease is cathepsin D.

Embodiment I-42. The method of embodiment 40, wherein concentration of cathepsin D in the cell culture medium is less than about 100 ppm.

Embodiment I-43. The method of embodiment 29, wherein concentration of cathepsin D in the cell culture medium is less than about 10 ppm.

Embodiment I-44. The method of embodiment 36, wherein the culturing is carried out at a temperature from about 35° C. to about 37° C.

Embodiment I-45. The method of embodiment 36, wherein the culturing is carried out at a temperature of about 35° C.

Embodiment I-46. The method of embodiment 36, wherein the culturing is performed for 7-12 days.

Embodiment I-47. The method of embodiment 36, wherein the culturing is performed for 8 days.

Embodiment I-48. A method for producing a truncated aflibercept, said method comprising:
- culturing a mammalian cell producing aflibercept in a cell culture medium, wherein the cell culture medium includes cathepsin D; and
- harvesting a preparation of the truncated aflibercept from the cell culture medium and produced by the mammalian cell.

Embodiment I-49. The method of embodiment 48, wherein the preparation includes aflibercept.

Embodiment I-50. A method for quantitative measurement of Cathepsin D in a sample, comprising:

obtaining isolated antibody specific for a protein with an amino acid sequence comprising an amino acid sequence of Cathepsin D;

attaching said isolated antibody to a solid support;

reacting attached isolated antibody with said sample including cathepsin D;

providing a detector capable of recognizing an amino acid sequence which is separate and distinct from the amino acid sequence recognized by the attached isolated antibody;

effecting an immunoreaction; and detecting said immunoreaction to quantitatively measure the cathepsin D in the sample.

Embodiment I-51. The method of embodiment 50, wherein the isolated antibody is a polyclonal antibody.

Embodiment I-52. The method of embodiment 50, wherein the isolated antibody is a rabbit isolated rabbit polyclonal antibody.

Embodiment I-53. The method of embodiment 50, wherein the isolated antibody is a goat isolated rabbit polyclonal antibody.

Embodiment I-54. The method of embodiment 50, wherein the isolated antibody is obtained by immunizing an animal to the protein with an amino acid sequence comprising an amino acid sequence of Cathepsin D to obtain serum from the animal: contacting the serum to a chromatography column including cathepsin D; and collecting an eluate from the chromatography including the isolated antibody.

Embodiment I-55. The method of embodiment 50, wherein the protein with the amino acid sequence comprising the amino acid sequence of Cathepsin D comprises a mmh tag.

Embodiment I-56. The method of embodiment 51, wherein the isolated antibody is obtained by immunizing an animal to the protein with an amino acid sequence comprising an amino acid sequence of Cathepsin D to obtain serum from the animal; contacting the serum to a chromatography column including cathepsin D; and collecting an eluate from the chromatography including the isolated antibody.

Embodiment I-57. The method of embodiment 56, wherein the eluate from the chromatography including the isolated antibody is contacted to a second chromatography column including anti-mmh antibodies and collecting the flowthrough including the isolated antibody.

Embodiment I-58. A method for purification of aflibercept sample, the method comprising:

harvesting a preparation of aflibercept, wherein the preparation contains an aspartic protease and subjecting the preparation to a size exclusion chromatography column, where the size exclusion chromatography column includes at least about 1000 plates of 100 cm thickness and the size exclusion chromatography column provides fractions including the aflibercept and fractions including the aspartic protease inhibitor, thereby purifying the aflibercept sample.

Embodiment I-59. The method of embodiment 58, wherein the preparation includes a truncated aflibercept.

Embodiment I-60. The method of embodiment 58, wherein the aspartic protease is cathepsin D.

Embodiment I-61. The method of embodiment 58, wherein the pH of the aflibercept sample is about 6.3 to about 6.6.

Embodiment I-62. The method of embodiment 58, wherein a surfactant is added to the aflibercept sample prior to subjecting it to the size exclusion chromatography column.

Embodiment I-63. The method of embodiment 62, wherein a surfactant is polysorbate 20.

Embodiment I-64. The method of embodiment 58 further comprising at least one other chromatography selected from the group consisting of anion exchange chromatography, cation exchange chromatography, and hydrophobic interaction chromatography.

Embodiment I-65. The method of embodiment 58, where the size exclusion chromatography column includes at about 1000 to about 1500 plates.

Embodiment I-66. The method of embodiment 58, where the size exclusion chromatography column includes at least about 1100 plates.

Embodiments Set II

Embodiment II-1. A process of purifying a VEGF receptor fusion protein, comprising:

flowing a drug substance intermediate that comprises the VEGF receptor fusion protein, a surfactant, and an aspartyl protease through a size exclusion chromatography (SEC) column;

collecting a first eluate from the SEC column that comprises the VEGF receptor protein and an amount of less than 1 ppm of the aspartyl protease; and excluding from the collected first eluate a second eluate that comprises the VEGF receptor protein and the aspartyl protease.

Embodiment II-2. The process of embodiment 1, wherein the first eluate has less than 0.3 ppm of the aspartyl protease and the second eluate has greater than 0.3 ppm of the aspartyl protease.

Embodiment II-3. The process of embodiment 1 or 2, wherein the process comprises, prior to collecting the first eluate, determining an amount of the aspartyl protease in one or more fractions of the drug substance intermediate eluting from the SEC column Embodiment II-4. The process of any one of embodiments 1-3, wherein the amount of the aspartyl protease is determined by an activity assay or by liquid chromatography-mass spectrometry (LC-MS).

Embodiment II-5. The process of any one of embodiments 1-3, wherein the amount of the aspartyl protease is determined by an enzyme-linked immunosorbent assay (ELISA).

Embodiment II-6. The process of embodiment 5, wherein the aspartyl protease is a cathepsin D and the ELISA is based on an anti-Chinese hamster ovary cathepsin D antibody.

Embodiment II-7. The process of any one of embodiments 1-6, wherein the drug substance intermediate comprises the VEGF receptor fusion protein at a concentration of at least 41 mg/mL.

Embodiment II-8. The process of any one of embodiments 1-7, wherein the drug substance intermediate comprises the surfactant at a concentration of at least 0.003%.

Embodiment II-9. The process of any one of embodiments 1-8, wherein the surfactant comprises a non-ionic surfactant having a polyoxyethylene moiety.

Embodiment II-10. The process of any one of embodiments 1-9, further comprising, prior to the SEC column, harvesting a preparation of the anti-VEGF protein produced by a host cell genetically engineered to express the anti-VEGF protein in a culture medium, purifying the preparation by liquid chromatography, and adding a surfactant to the purified preparation to form the drug substance intermediate.

Embodiment II-11. The process of embodiment 10, wherein the preparation is purified by Protein A chromatography, anion exchange chromatography, cation exchange chromatography, hydrophobic interaction chromatography, or a combination of two or more thereof.

Embodiment II-12. The process of any one of embodiments 1-11, further comprising concentrating and filtering the first eluate to form a concentrated pool.

Embodiment II-13. The process of any one of embodiments 1-12, further comprising formulating the first eluate with one or more pharmaceutically acceptable excipients, wherein the VEGF receptor fusion protein has a concentration of at least 41 mg/mL in the formulation.

Embodiment II-14. The process of any one of embodiments 1-13, wherein the aspartyl protease is cathepsin D.

Embodiment II-15. The process of any one of embodiments 1-14, wherein the surfactant is a polysorbate.

Embodiment II-16. The process of any one of embodiments 1-15, wherein the surfactant is added to the drug substance intermediate prior to flowing it through the SEC column.

Embodiment II-17. The process of any one of embodiments 1-16, wherein the VEGF receptor fusion protein is aflibercept.

Embodiment II-18. A process of purifying aflibercept, comprising:

- flowing a drug substance intermediate that comprises aflibercept, a surfactant, and cathepsin D through a size exclusion chromatography (SEC) column;
- collecting a first eluate from the SEC column that comprises the aflibercept and an amount of less than 1 ppm of the cathepsin D; and
- excluding from the collected first eluate a second eluate that comprises the aflibercept and the cathepsin D.

Embodiment II-19. The process of embodiment 18, wherein the surfactant comprises a non-ionic surfactant having a polyoxyethylene moiety.

Embodiment II-20. A formulation comprising one or more pharmaceutically acceptable excipients and aflibercept at concentration of from about 100 mg/mL to about 300 mg/mL, wherein the formulation includes less than 0.3 ppm of cathepsin D and has a pH of from 5.5 to 6.1.

Embodiment II-21. The formulation of embodiment 20, comprising less than 0.05 ppm of cathepsin D.

Embodiment II-22. The formulation of embodiment 20 or 21, wherein the formulation is prepared from collecting a first eluate of a drug substance intermediate by a process comprising:

- flowing a drug substance intermediate that comprises aflibercept, a surfactant, and cathepsin D through a size exclusion chromatography (SEC) column;
- collecting a first eluate from the SEC column that comprises the aflibercept and an amount of less than 1 ppm of the cathepsin D; and excluding from the collected first eluate a second eluate that comprises the aflibercept and the cathepsin D.

EXAMPLES

Example 1. Assessment of Degradation Products During Aflibercept Manufacturing A sample of an aflibercept drug substance intermediate (DSI) was analyzed for various attributes during its stability testing. The DSI sample was obtained from the downstream purification process after carrying out protein A chromatography, CEX, AEX, and HIC. An accelerated stability (25° C. over 6 Months) and stressed stability (45° C. over 1.2 Months) was carried out on lots of DSI from different facilities (facility A and facility B). The results from the two lots were compared and it was found that a greater rate of degradation was observed in DSI of the Lot from facility A than of the Lot from facility B.

Example 2. Assessment of Degradation Products in Aflibercept Drug Substance

Aflibercept drug substance (DS) was taken from drug substance lots i.e., after the manufactured aflibercept was purified and formulated into a pharmaceutically acceptable form and this DS was analyzed for various attributes during its stability testing.

An accelerated stability (25° C. over 6 Months) was carried out on two lots of DS from different facilities. The results from the two lots were compared and it was found that the rate of degradation for both lots from facility A and B, was comparable.

This was in contrast to the results from Example 1.

Example 3. Evaluation of the NR-1 Band

Figure 2:
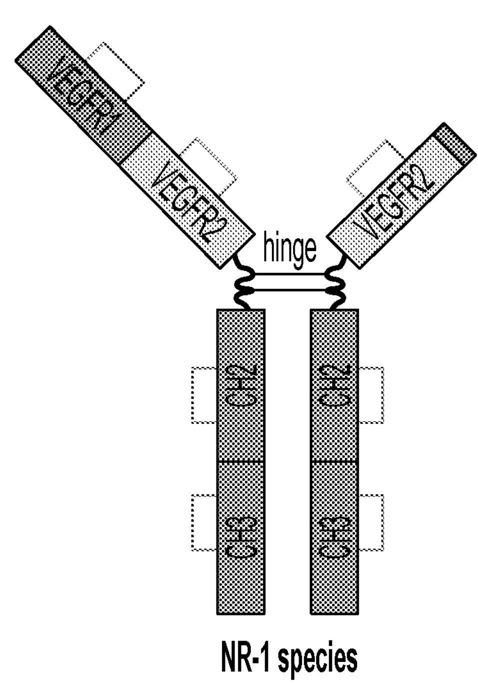
FIG. 2 is a cartoon representation of the structure of NR-1 species, according to an exemplary embodiment.

In order to examine the truncations in aflibercept that forms the NR-1 band, SDS-PAGE was performed. The general sequence of aflibercept is shown in FIG. 1. It was known based on earlier studies that NR-1 species (a cartoon of which is shown in FIG. 2) were formed when the full-length aflibercept lost almost the entire VEGFR1 domain on one arm due to the truncation at the following two sites toward the C-terminal region of the VEGFR1 domain: between T90 and N91 between N99 and T100.

To improve the sensitivity and fidelity, the analysis was performed by changing usual mass analysis technique by (a) performing FABRICATOR digestion to remove the Fc portion of aflibercept, (b) complete deglycosylation was necessary to remove the heterogeneity from up to 10×N-glycosylation from the analytes and (c) denaturing the samples using Rapigest, a mild denaturing condition which does not deactivate PNGaseF enzyme for deglycosylation. The analysis was performed by denaturing SEC-MS, which can provide (partial) liquid chromatography separation between the intact receptor domain and NR1 species (with Fc removed) for the successful detection of the low levels of NR1 species. The DS and DSI sample from lots A and B were analyzed using a modified mass analysis (samples 1-7 are representative of both DS and DSI samples from both the lots). The modification made is possible to differentiate the peaks of the receptor domain of aflibercept and truncated aflibercept. The assessment of the receptor domain of the truncated aflibercept further revealed the different positions that led to truncations.

On assessing the truncations due to each of the positions (N99T100, Y94H95, and T90N91) in the DSI and DS samples from Lot of A and Lot of B, it became clear that the NR-1 due to these truncations was not that appreciable in nature. This led to the revelation that the NR-1 band in the DSI and DS samples was predominantly due to a novel clipping site Y92/L93.

The dSEC-MS Analysis of Selected lot of A and lot of B DSI and DS material under accelerated stability revealed a novel clipping site Y92/L93 responsible for faster NR-1 growth. The effect of truncation due to Y92/L93 is predominant in Lots A and B DSI samples. The level of truncation between Y92 and L93 was very low in all DS samples as well as DSI samples from both facilities taken at time=0. The level of truncation between Y92 and L93 increased in the DSI accelerated stability samples, but not in the DS accelerated stability samples from both sites. Under accelerated stability conditions, the rate of truncation between Y92 and L93 in Lot of A was higher than that in the Lot of B.

Example 4. Investigation of the Cause of Truncation Between Y92 and L93 of Aflibercept in DSI Lots As illustrated from Examples 1-3, the NR-1 band was predominant in DSI samples compared to DS samples.

Due to the distinction in the number of HCPs in the samples. HCPs from the samples were characterized by the method developed by Johnson et al. See O'Brien Johnson et al. (2020). Combination of FAIMS, Protein A Depletion, and Native Digest Conditions Enables Deep Proteomic Profiling of Host Cell Proteins in Monoclonal Antibodies. Analytical Chemistry, 92(15), 10478-10484. It was also observed that there was a substantial overlap between HCPs found in Lot of A DSI and Lot of B DSI. Additionally, HICPs were also consistent between DS and DSI lots from the same facility.

The characterization of the HCPs revealed a total of 132 HCPs (data not shown). But cathepsin D was detected in all the lots for DS and DSI from both the facilities. The comparative analysis also revealed that DSI lot from facility A had the highest amount of cathepsin D levels.

This led to the hypothesis that cathepsin D is likely responsible for the NR-1 band formation. Other proteases detected were C1rA and Cathepsin Z. However, their levels were very low and not substantially different between the two facilities, nor DS and DSI lots, and observed cleavages did not match protease specificity.

Example 5. Confirmation Study of Cathepsin D LED to Truncation of Aflibercept at Y92L93

Once cathepsin D was identified to be a potential reason for the cleavage of aflibercept, a cathepsin D inhibitor was used to confirm the finding. AEBSF and Aprotinin bovine lung (serine protease inhibitors), E64 and Leupeptin hemisulfate (cysteine protease inhibitors) and pepstatin A (an aspartic protease inhibitor) were evaluated for their ability to inhibit activity of cathepsin D.

To the samples from lots from both the facilities containing DSI at t=0, pepstatin A was added at 37° C. and % of NR-1 band formed was assessed at day 3 and day 5. For both the samples, NR-1 band increase stopped, and Y/L clipping ceased after incubating the DSI samples with pepstatin A, suggesting cathepsin D is likely the cause for NR-1 band formation.

Example 6. Production of Y92L93 Clipping of Aflibercept Using Cathepsin D

Production of the Y92L93 clipping was attempted using cathepsin D. To a sample of aflibercept DS, cathepsin D was added and incubated at 37° C. at pH 6.1. Different concentrations of cathepsin D were evaluated, including 1 ppm, 2 ppm, 5 ppm, and 10 ppm. Increased NR-1 band did not correspond to the amount of Cathepsin D (CatpD) spiked in at pH 6.1 (data not shown). Negligible Y/L clipping was observed with 10 ppm Cathepsin D spiked in at pH 6.1 even for 8 days and <1% of Y/L clipping was observed with 100 ppm Cathepsin D spiked in at pH 6.1 for 8 days.

Since the failure of cathepsin D to affect the truncation could be due to reaction conditions, the experiment was repeated at a lower pH since cathepsin D needs to be activated by lower pH for conformational switch to mature cathepsin D. Cathepsin-D is an aspartic protease that depends critically on protonation of its active site Asp residue. Along with Asp-protonation, lower pH also leads to conformational switch in mature cathepsin-D. See Briozzo P et al. (1988). Cancer Research. 48 (13): 3688-92.

To test the DS samples with the presence of activated cathepsin D, to a sample from DS at t=0, 100 ppm acidified cathepsin D was added at 37° C. and incubated for 5 hours. As suspected, the activated cathepsin D led to Y/L clipping of aflibercept and the truncating effect increases over time.

The clipping activity was also observed at neutral condition when acidified cathepsin 1) was added. For example, when 0.5-20 ppm of acidified cathepsin D is added to an aflibercept DS sample and incubated for 7 days at 37° C. the results demonstrated a correlation between spiked-in cathepsin D and NR-1 band formation, and Y/L cleavage.

Example 7. Impact of pH on NR-1 Band Formation

Figure 3:
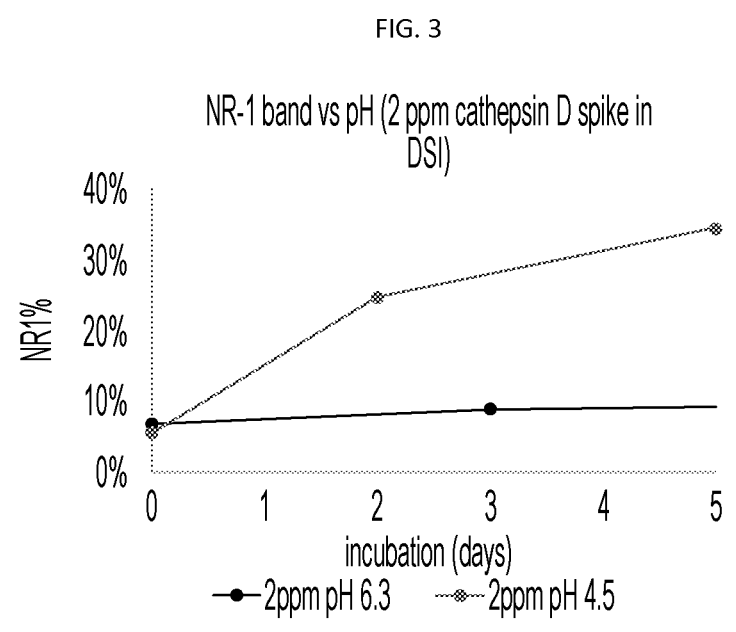

Since cathepsin D is an acidic protease (optimal pH between 2 and 5), experiments to test the impact of pH on the activity of cathepsin D on a DSI sample revealed that the lower pH (4.5) produces significant NR-1 band compared to a slightly acidic pH (6.3). See FIG. 3. Testing of DSI samples from both facilities A and B for aflibercept production also show similar results.

The impact of pH is so significant that use of different buffers can also show a difference in the Y92L93 clipping observed during the production of aflibercept. For example, citric acid was employed at facility B to achieve a pH of 6.1 and sodium citrate was employed at facility A to achieve a pH of 6.2, despite other conditions remaining the same (i.e., incubation of DSI at 37° C. for 12 days, intermediate time point taken at 3$^{rd}$ and 6$^{th}$ day). While the difference in the pH is 0.1, the effect through cathepsin D based clipping is notable over time (data not shown).

When the pH is increased to 6.45 by adding sodium citrate, the formation of NR-1 band formation decreased i.e., it stopped the 92Y93L clipping of aflibercept. All samples were incubated at 37° C. for 12 days, intermediate time point taken at 3rd and 6th day.

Results demonstrated pH 6.45 can effectively slow down NR1 band increase and prevent YL cleavage. Effectively no NR-1 band is formed during aflibercept manufacturing when the pH is 6.45 (data not shown).

Example 8. Absolute Quantitation of Cathepsin D

The quantification procedure as shown in FIG. 4 was followed. The exact parameters as listed in FIG. 5 were followed. Based on this method, it was determined that the average level of cathepsin D in facility A DSI (1.37 ppm) was about 1.5 times that in facility B DSI (0.09 ppm). See FIG. 6.

Example 9A. Detection of Cathepsin D Levels

The quantification procedure as shown in FIGS. 4 and 5, while adequate, had some limitations. For example, the sensitivity of Cathepsin D was limited to 0.5 ppm, e.g., (cathepsin D ng/mL)/(aflibercept mg/mL). See FIG. 6. Given the low levels of Cathepsin D that were found to be present coupled in the lots with the method of detection and quantitation by mass spec, a more sensitive method was required. As evident from FIG. 6, many lots had Cathepsin D at levels close to or at 0.5 ng/mL.

A Cathepsin D host cell protein (HCP) ELISA assay was developed to overcome the above-mentioned challenges.

Figure 7:
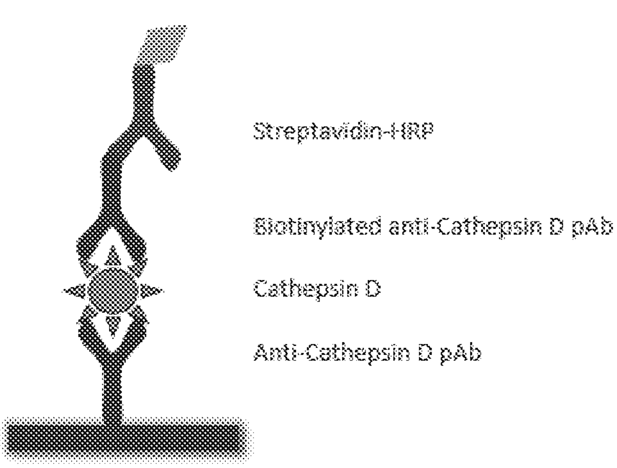
FIG. 7 displays an ELISA assay for quantifying cathepsin D in a sample, according to an exemplary embodiment.
Figure 8:
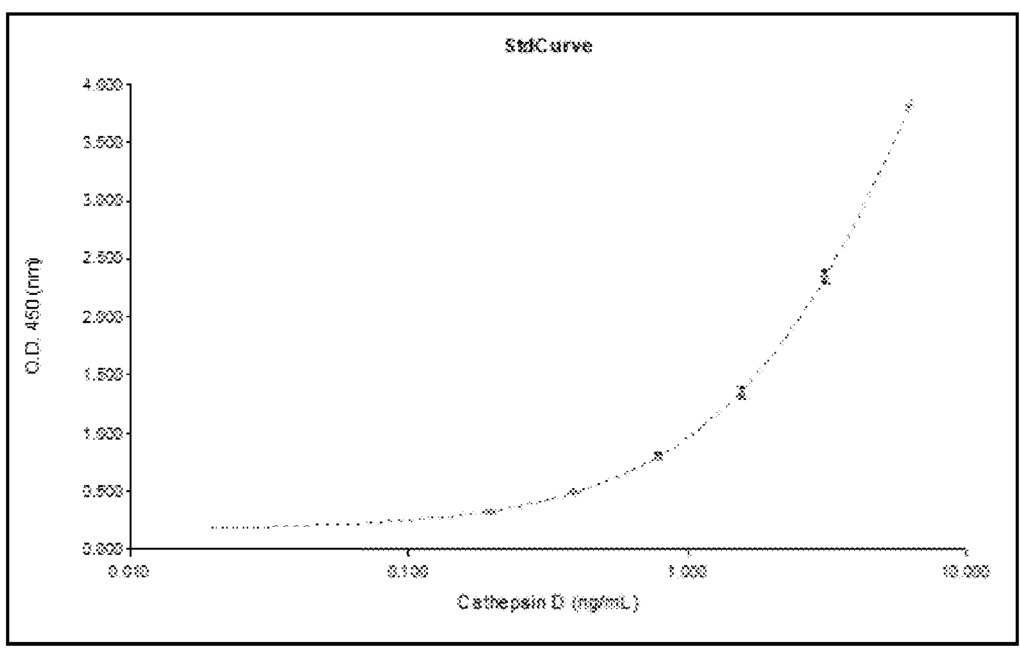
FIG. 8 shows a chart presenting the limit of detection (LOD) for an ELISA assay for quantifying cathepsin D in a sample, according to an exemplary embodiment.

A schematic of the assay developed is outlined in FIG. 7. The assay was developed using Cathepsin D expressed from CHO cells with mmh tag. A polyclonal anti-cathepsin D antibody was generated in rabbit and was affinity purified against recombinant cathepsin D. The assay so developed has a LOD of 0.2 ng/mL. See FIG. 8. This ELISA assay is more amenable to laboratory quality control analysis, compared to mass spectrometry.

This assay used an indirect sandwich ELISA approach to quantify the Cathepsin D protein. A 96-well plate was coated with anti-CHO Cathepsin D polyclonal antibody. After overnight incubation at 4° C., the plate was blocked, and then standards, controls and samples were loaded to the coated plate. Cathepsin D that is present will be bound and immobilized. Next, biotinylated polyclonal antibody against CHO Cathepsin D was added as the primary antibody detection agent. Subsequently, streptavidin-HRP was added as the detection reagent. Lastly, Tetramethylbenzidine (TMB) was added as the substrate. The absorbance at 450 nm was then measured using the NEO plate reader. The data was then imported for data analysis.

Coating Antibody and Plate Coating: Working solutions of Cathepsin D HCP coating antibody were prepared in 1×PBS spanning a range of concentrations. These coating concentrations were tested by adding 100 μL/U well of each Cathepsin D antibody coating concentration solution and subsequently stored overnight at 4° C. The optimal condition was selected after testing.

Plate Blocking: Plate blocking used blocking buffer (BSA in 1×PBST) at 300 μL/well and incubated with shaking for a set amount of time.

Standard Preparation and Assay Range: The standard curve was prepared using the CHO Cathepsin D protein that was produced. A variety of standard ranges were tested to determine the appropriate range to be used in the assay.

Primary Antibody: A range of working solutions of the primary antibody were prepared in Assay buffer (BSA in 1×PBST) and incubated for one hour with shaking. The optimal condition was determined after testing was complete.

Streptavidin-HRP: A range of working solutions of Streptavidin-HRP were prepared in Assay buffer (BSA in 1×PBST) and incubated for one hour with shaking. The optimal dilution was determined after testing was complete.

Figures 9, 10:
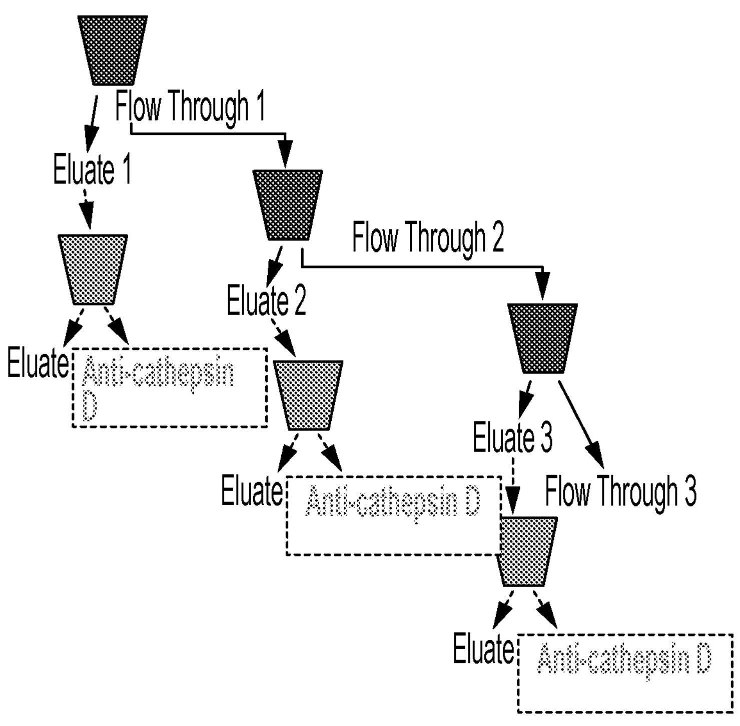
FIG. 9 is a chart that shows levels of cathepsin D (in ppm) in different pools for the manufacturing process of a VEGF Trap1, according to an exemplary embodiment.
FIG. 10 shows a purification scheme for anti-cathepsin D antibody, according to an exemplary embodiment.

VEGF Trap 1 (a full-length VEGF Trap) process was analyzed for levels of cathepsin D. The process steps/pools during the production of the VEGF Trap 1 were depth filtrate pool, AEX pool and HIC pool. The ELISA assay was able to detect up to 4 ppm in the samples (Table 1 and FIG. 9).

TABLE 1

| Process | Sample Conc | Cathepsin D | | |
|---|---|---|---|---|
| Step Process step | (mg/mL) Sample | ng/ml | PPM (ng/mg) | PPM (nmol/mmol ) |
| Depth Filtrate | 7.6 | 31.3 | 4.1 | 13.5 |
| AEX | 9.43 | 31.2 | 3.3 | 10.8 |
| HIC | 3.88 | <LOQ | <LOQ | <LOQ |

Example 9B. Generation of Anti-Cathepsin D Antibody in Goat

Instead of rabbit anti-cathepsin D pAb, goat anti-cathepsin D pAb were generated. The purification scheme for anti-cathepsin D pAb from goat sera included use of series of affinity purifications with an affinity column including cathepsin D generated in-house. See the purifications described in FIG. 10 and FIG. 11.

Goats were immunized using the CHO Cathepsin D protein as the immunogen. Goats were boosted with the CHO Cathepsin D protein on a regular interval to both increase antibody titer and to generate enough bleeds.

Bleed Purification: Bleeds were purified using two separate affinity column purifications. One was prepared by using the CHO Cathepsin D protein while the other was prepared using a protein that contains a histidine tag. Purifications were performed on an AKTA FPLC system.

Antibody Characterization and Labeling: Antibody concentration was measured using a protein concentration method. A portion of the purified antibody was subsequently labelled with biotin. After biotin labelling, the antibody concentration was measured using a protein concentration method.

Figure 12:
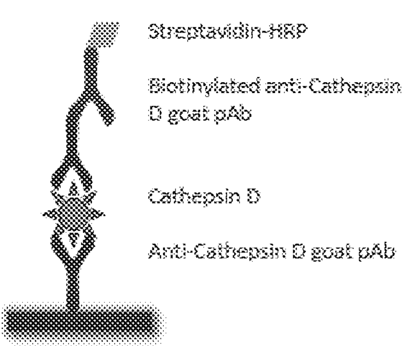
FIG. 12 displays an ELISA assay for quantifying cathepsin D in a sample, according to an exemplary embodiment.
Figure 13:
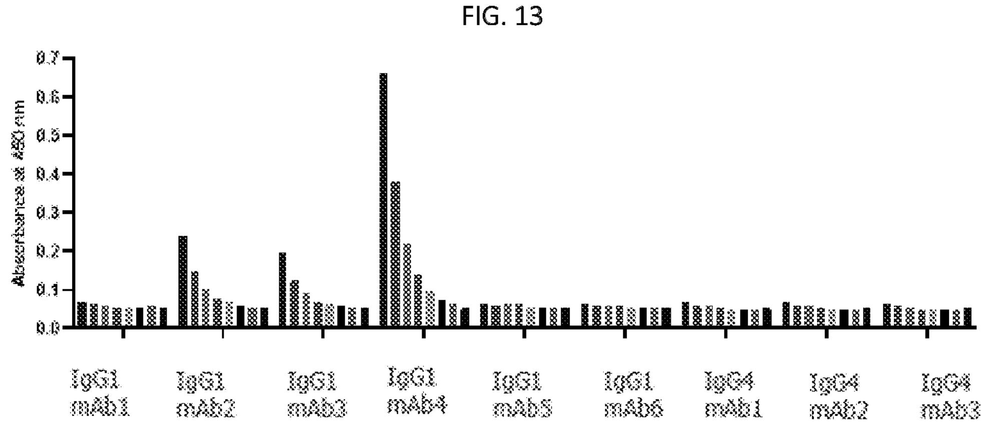
FIG. 13 shows a chart of levels of cathepsin D quantified as absorbance levels in samples with serially diluted IgG1 and IgG4 antibodies, wherein the levels are quantifying using an assay according to an exemplary embodiment.

Using this goat anti-cathepsin pAb, the ELISA method described above was used. The ELISA method using goat anti-cathepsin pAb is shown in FIG. 12. This ELISA method was able to detect 0.05 ng/ml (LOD) and quantitate 0.3 ng/mli (LOQ). For 6 IgG1 mAbs and 3 IgG4 mAbs, the ELISA method using goat anti-cathepsin pAb detected low levels of cathepsin D in the IgG1 mAbs and none in the IgG4 mAbs. See FIG. 13. The LOD and LOQ in ppm (ng/ml) varied based on the concentration of the drug sample tested.

Figure 14:
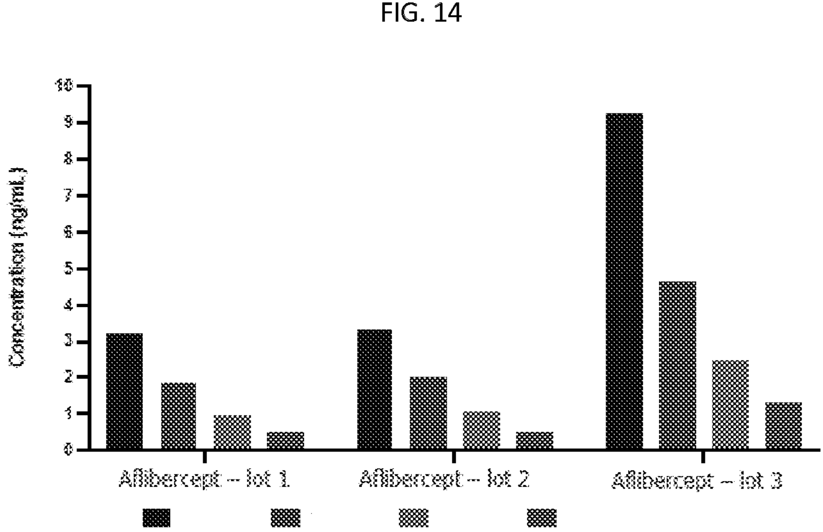
FIG. 14 shows a chart of levels of cathepsin D in different lots of aflibercept manufacture, wherein the levels are quantifying using an assay according to an exemplary embodiment.

Similar detections were observed for aflibercept process lots i.e., the LOD and LOQ in ppm (ng/ml) varied based on the concentration of the drug sample tested (FIG. 14).

Example 10. Stability Study on Drug Substance Intermediate Lots at Varying Concentrations This study investigated how a residual HCP can piggyback through the aflibercept DSI manufacturing process. Unexpected, a high dose formulation of aflibercept (e.g., a 114.3 mg/mL formulated drug substance (FDS)) lot showed unacceptable stability during an accelerated stability test (25° C. for 6 months). The test showed increased rates of aggregation and fragmentation under the 25° C. condition.

Through this investigation it was found that variation in fragmentation and aggregation rates under the accelerated stability condition for DSI and 114.3 mg/mL FDS are likely attributable to low, variable, levels of a Chinese hamster ovary (CHO) host cell protease, cathepsin D. In addition, the purification process for aflibercept has an inherent variability where differences in the clearance of cathepsin D was observed from lot to lot. Small differences in the levels of cathepsin D have a greater impact on aggregation and fragmentation rates for a high concentration (e.g., 114.3 mg/mL) FDS under the accelerated condition compared to 40 mg/mL FDS. It is believed the buffer used with the high dose formulation is more favorable for cathepsin D activity, due to the higher protein concentration and lower formulation pH.

Figure 15A:
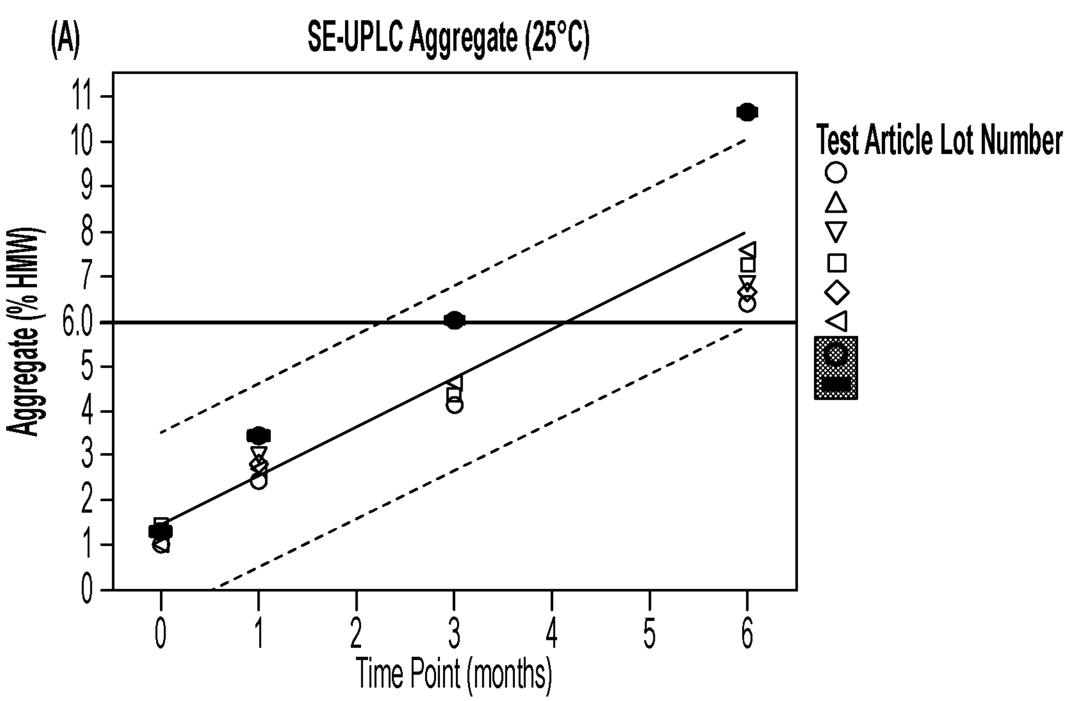
FIG. 15A shows a chart of accelerated stability trends for LMW species at 6 months at 25° C. (black circle and box) and comparator lots, according to an exemplary embodiment.
Figure 15B:
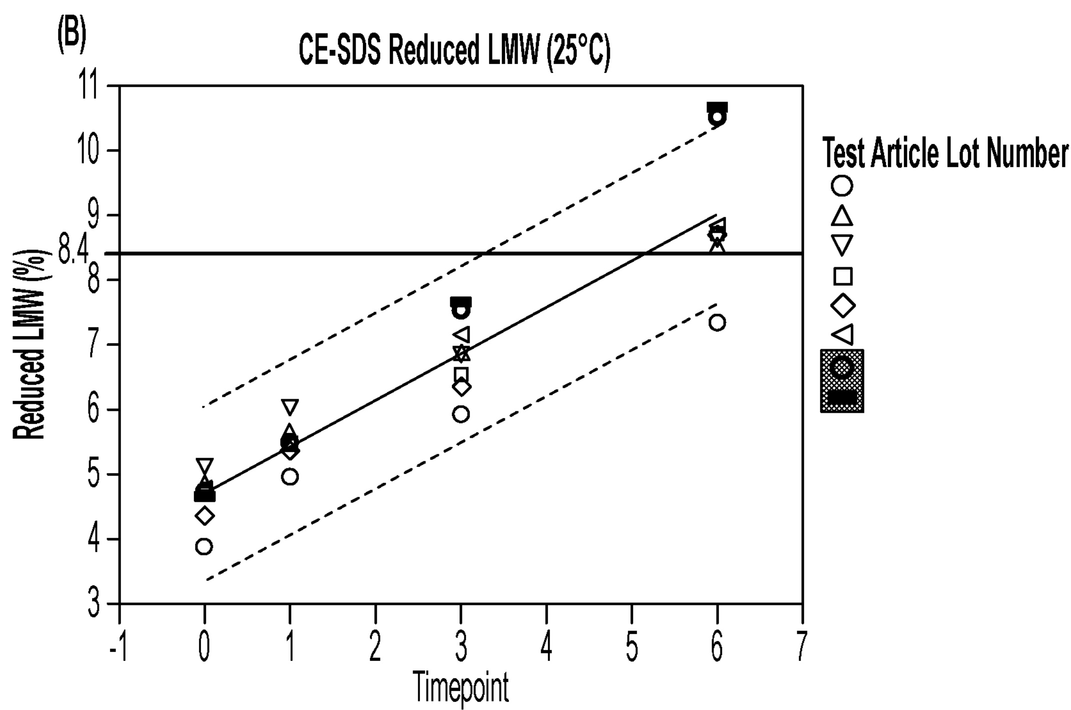
FIG. 15B shows a chart of accelerated stability trends for SE-UPLC aggregate species at 6 months at 25'C (black circle and box) and comparator lots, according to an exemplary embodiment.

Drug substance intermediate (DSI) lots containing aflibercept at two different concentrations (40 mg/ml and 114.3 mg/ml) were evaluated at 5° C. and 25° C. It was observed that accelerated stability results at 6 months at 25° C. showed reduced CE-SDS purity, low molecular weight (LMW) purity, low SE-UPLC main peak purity and high molecular weight (HMW) species for the of aflibercept lots with higher concentration (114.3 mg/mL) (FIG. 15A and FIG. 15B).

Figure 16A:
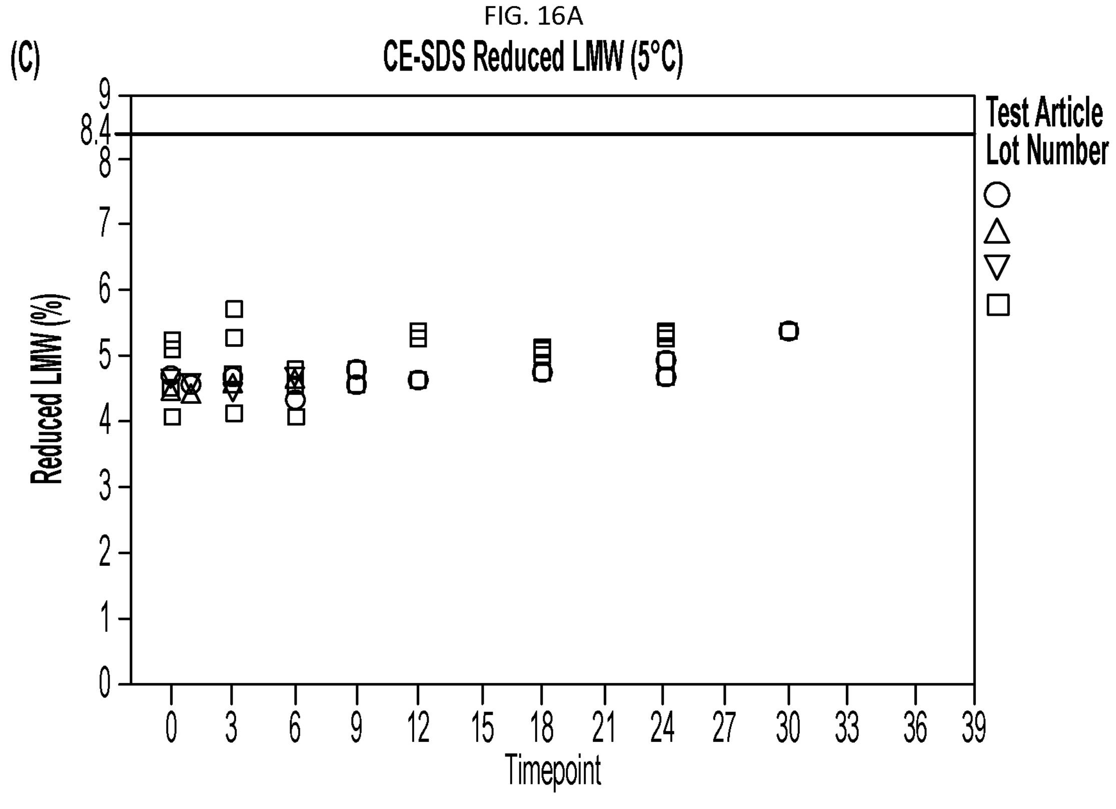
FIG. 16A shows a chart of accelerated stability trends for LMW species at 6 months at 5° C., according to an exemplary embodiment.
Figure 16B:
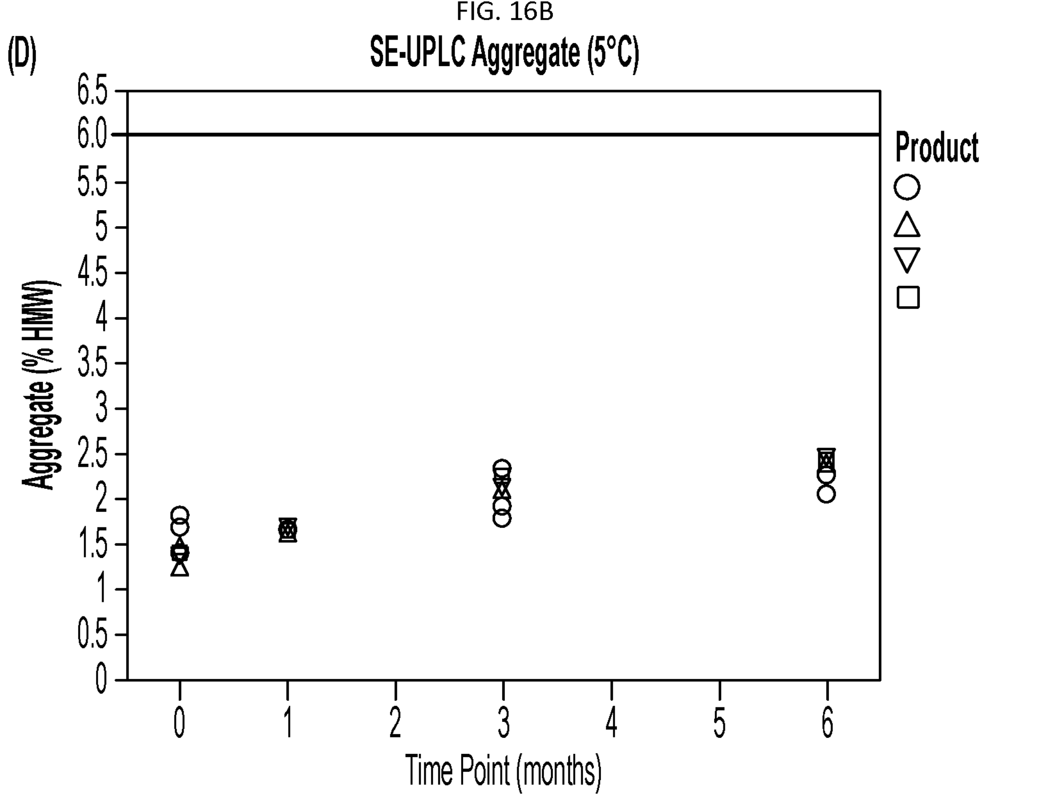
FIG. 16B shows a chart of accelerated stability trends for SE-UPLC aggregate species at 6 months at 5° C., according to an exemplary embodiment.

The stability testing at 5° C. did not show an unexpected stability result (FIGS. 16A and 16B). Notably, under the 5° C. condition, an absence of fragmentation was observed through the 12-month time point, while modelling of the SE-UPLC purity and aggregate data indicated that the faster rate was not anticipated.

Figures 17A, 17B, 18:
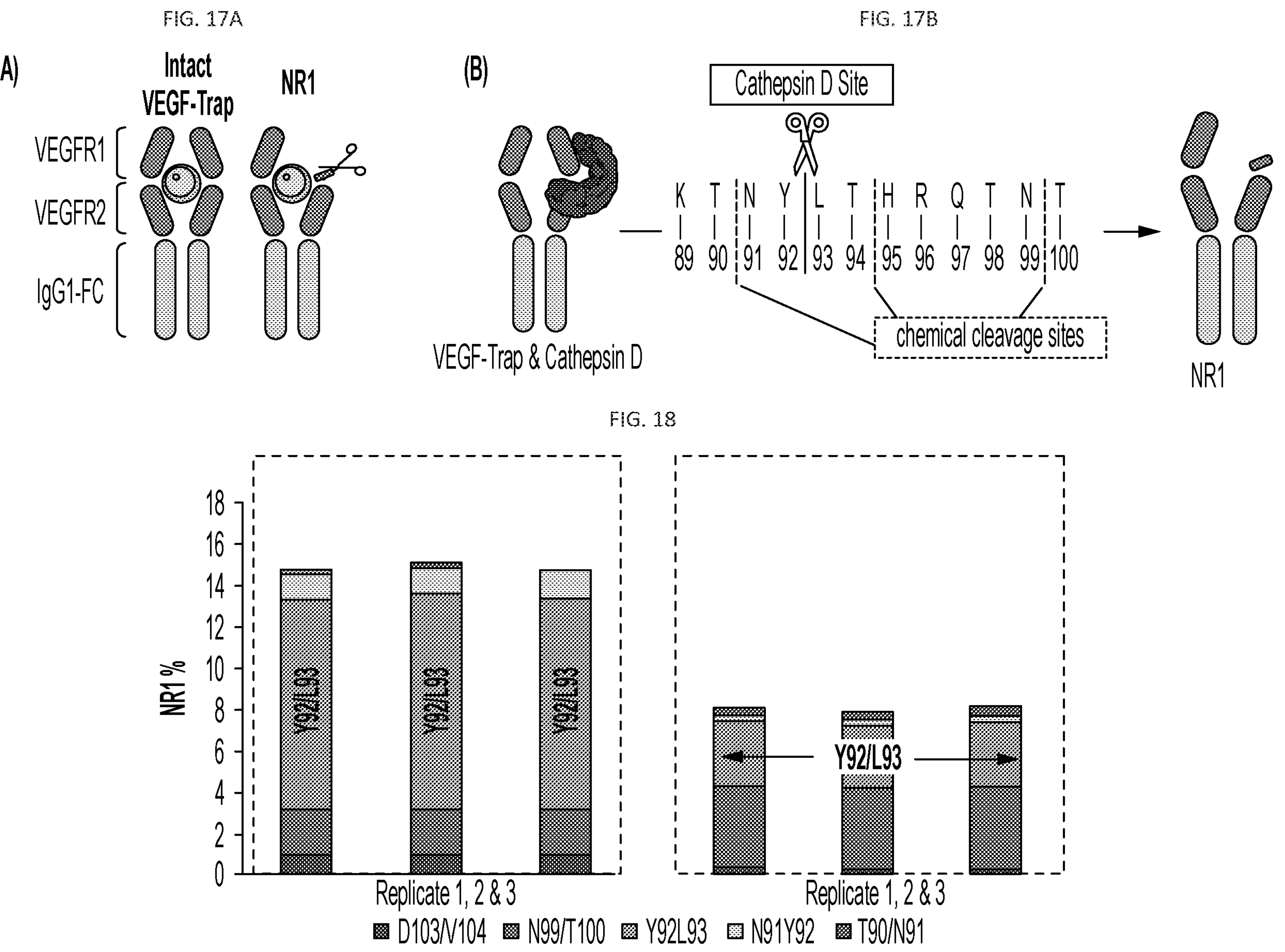
FIG. 17A is a schematic of intact VEGF-Trap trap (aflibercept) and the NR1 variant, according to an exemplary embodiment.
FIG. 17B shows the known VEGF-Trap cleavage sites from K89 to T100, according to an exemplary embodiment.
FIG. 18 are charts which display cleavage of VEGF-Trap (aflibercept) per sites quantified with increased Y92/L93 digestion confirmed for high concentration (HC) DSI derived Final drug substance (FDS), according to an exemplary embodiment.

VEGF-Trap can be cleaved in its R1D2 region, resulting in LMW species denoted NR1 (FIG. 17A). Cleavage at residues Y92/L93 was previously confirmed to be driven by CHO Host Cell Protein (HCP) cathepsin D (FIG. 17B).

Investigation into the deviation revealed that variation in fragmentation and aggregation rates under the accelerated stability condition for these lots is likely attributable to low, variable, levels of cathepsin D. The higher concentration lots (114.3 mg/ml) comprised higher amounts of cathepsin causing more cleavage of aflibercept at the Y93/L93 site forming the NR-1 species. See FIG. 17.

Figure 19:
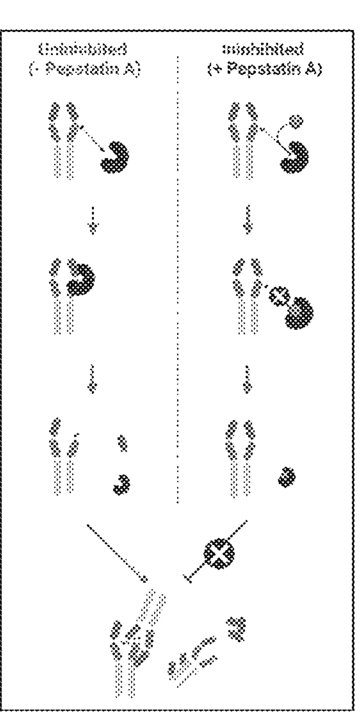
FIG. 19 is a schematic showing Cathepsin D-mediated VEGF-Trap aggregation.
Figure 20:
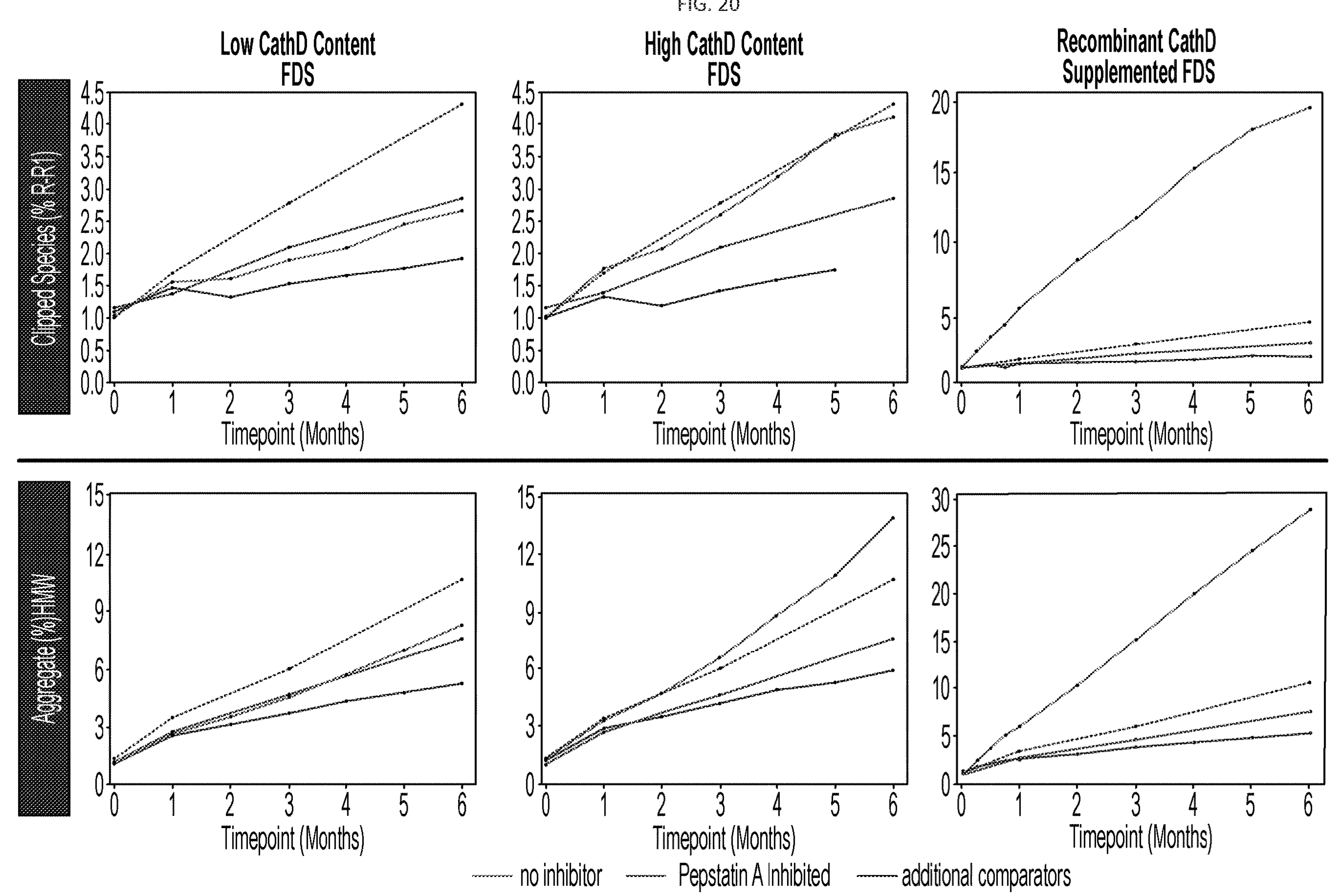
FIG. 20 is a panel of graphs showing Cathepsin D-mediated formation of NR1 linked to increased, according to an exemplary embodiment.

Mass spectrometry analysis further confirmed (3.4×) higher levels of Y92/L93 clipping for the unexpected aflibercept high concentration lot when compared to Y92/L92 clipping observed for low concentration lots (FIG. 18). Increased NR1 due to cathepsin D cleavage at Y92/L93 of aflibercept was linked to increased aggregate formation (FIG. 19 and FIG. 20).

Figure 22A:
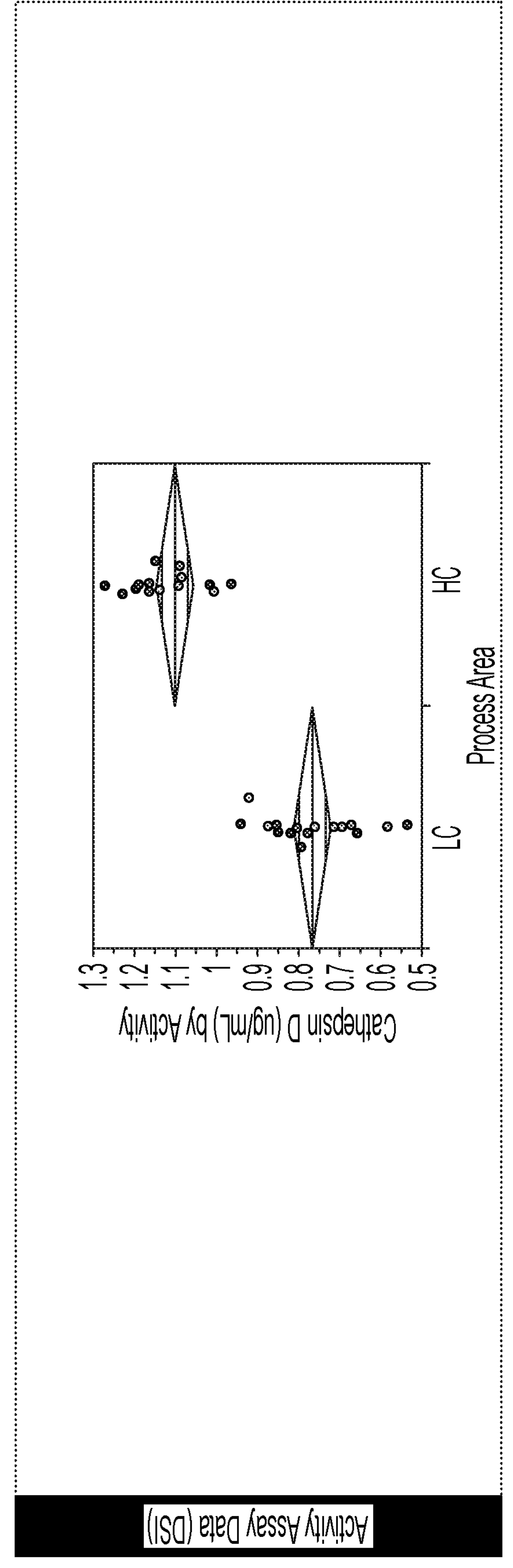
FIG. 22A and FIG. 22B display the results of activity assay (green box) and ELISA data (red box) of cathepsin D concentration at DSI and FDS, with fold reduction, according to an exemplary embodiment.
Figure 22B:
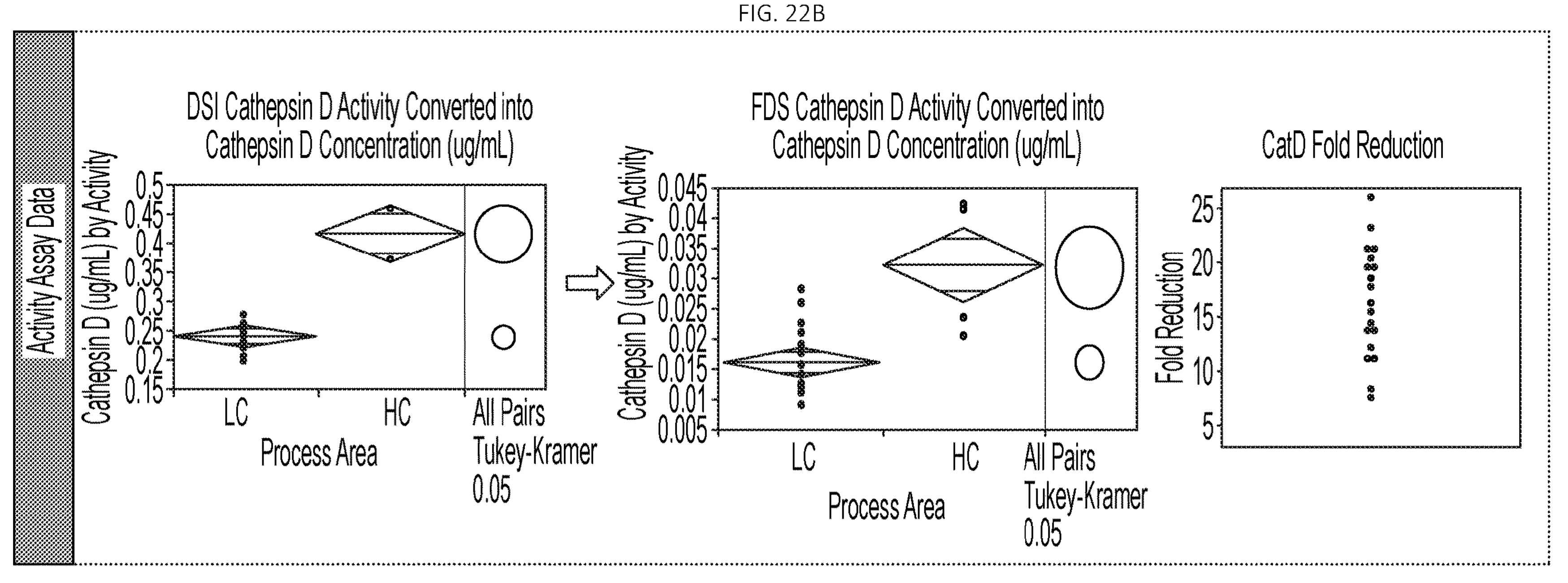
Figure 22C:
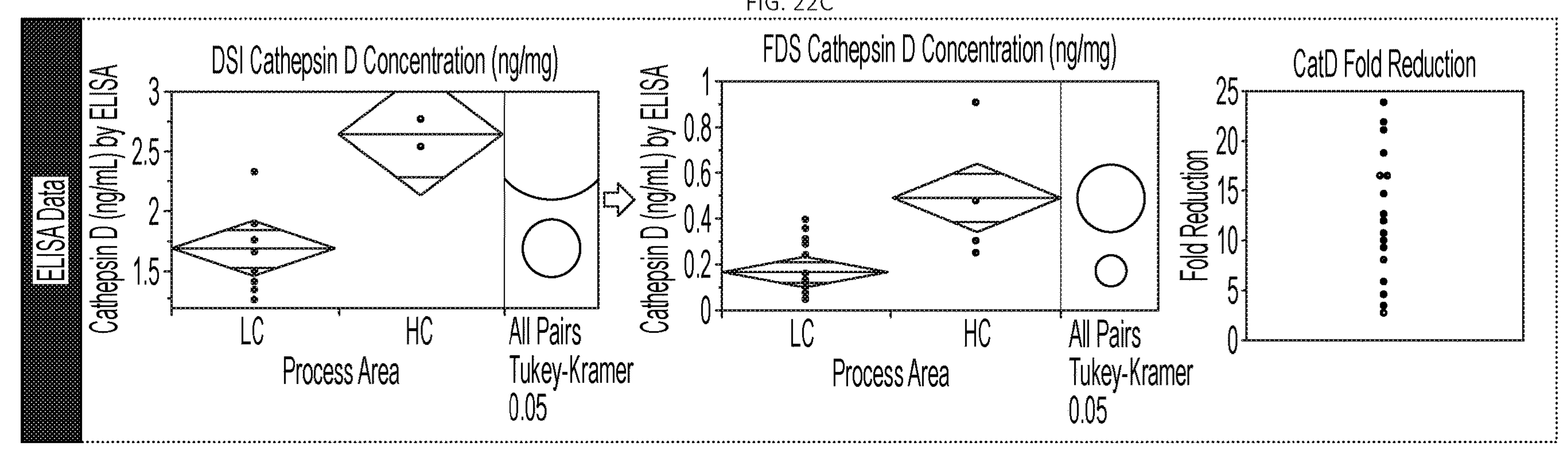

In addition, downstream process on the DSI lots showed an inherent variability where differences in the clearance of cathepsin D was observed from lot to lot (FIG. 21 and FIG. 22). FIG. 21 shows a statistically significant differences in cathepsin D concentrations between the downstream process pools for high concentration DSI lots and low concentration DSI lots (VI pool, CEX pool, AEX pool and HIC pool). The amount of cathepsin D in these pools was also calculated and showed higher levels of Cathepsin D in downstream process pools for high concentration DSI lots (FIG. 22).

Small differences in the levels of cathepsin D showed a greater impact on the high concentration DSI lots (20 lots, 114.3 mg/mL) in terms of aggregation and fragmentation rates under the accelerated condition compared to lower concentration DSI lots (20 lots, 40 mg/mL). It was observed that cathepsin D levels were more in the higher concentration DSI lots because of the higher protein concentration and the type of specific buffer used in those DSI lots.

Example 11. Interactions Between Aflibercept and Cathepsin D

Figures 23, 24:
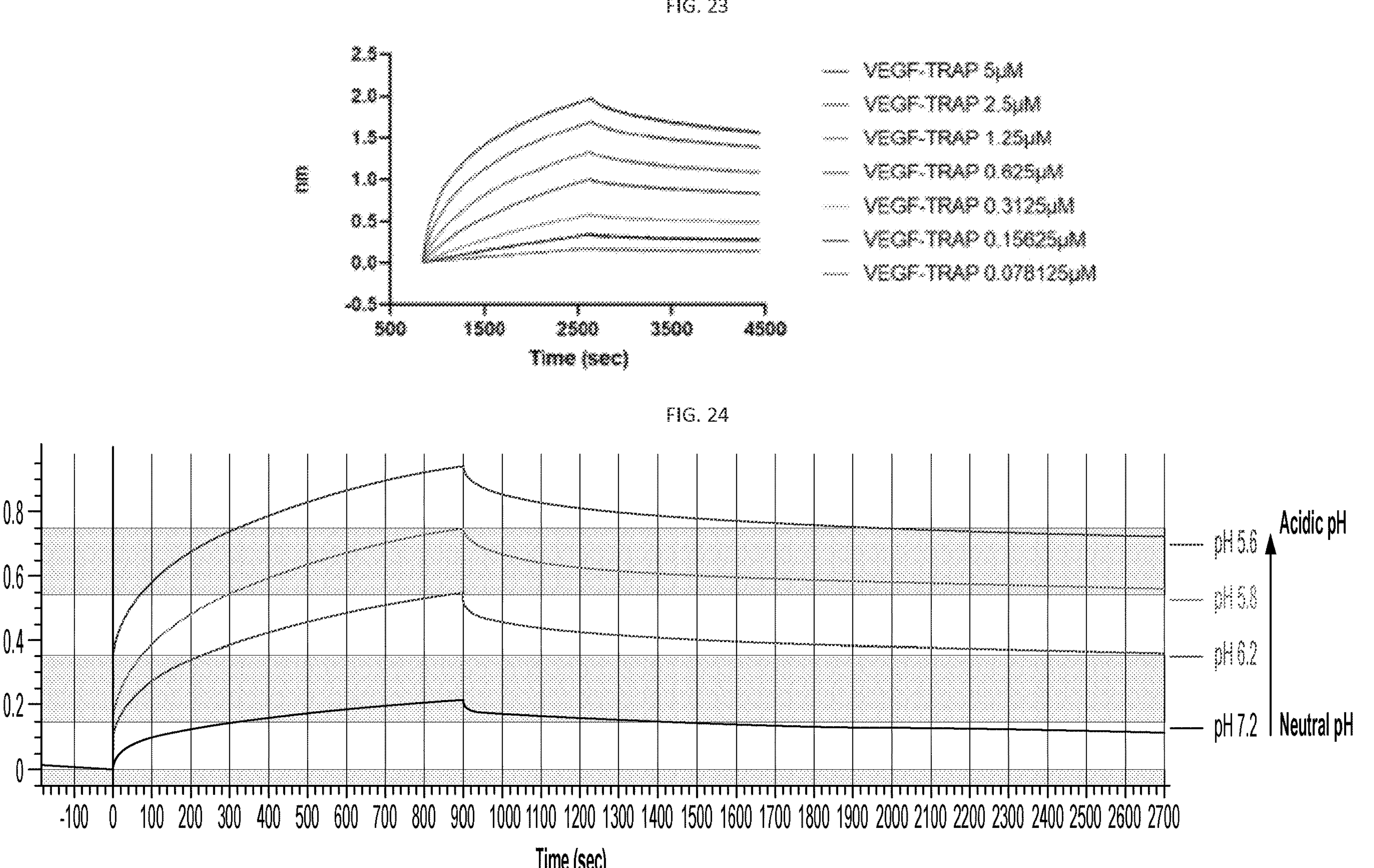
FIG. 23 displays Octet HTX sensorgrams of VEGF-Trap and cathepsin D interactions across a range of VEGF-Trap concentration, according to an exemplary embodiment.
FIG. 24 displays Octet HTX sensorgrams of VEGF-Trap and cathepsin D association and disassociation across a range of buffer pH, according to an exemplary embodiment.

Interaction analysis was carried out using OCTET HTX sensorgram. The results from the sensor showed that there was an aflibercept concentration dependent binding to Cathepsin D (FIG. 23). It was also shown that interaction between aflibercept and cathepsin D increased with reducing buffer pH (FIG. 24).

Example 12. Downstream Process for Cathepsin D Removal

Figure 25:
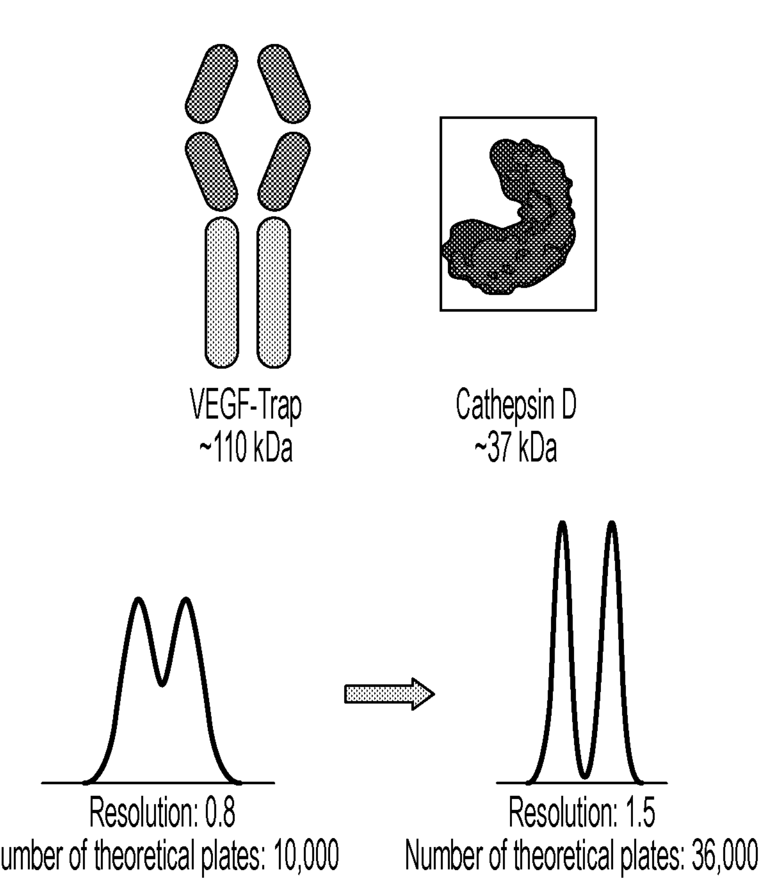
FIG. 25 is a schematic of VEGF-Trap (aflibercept) and cathepsin D with molecular weight differences, thereby showing enabling separation by SEC which is aided by higher number of plates (column efficiency), according to an exemplary embodiment.

Since cathepsin D was not sufficiently removed during the upstream process of producing aflibercept, including purification with chromatography, it was believed that the downstream operations provided an opportunity for cathepsin D removal from the product stream. For example, due to differences in molecular weight of aflibercept and cathepsin D it was believed that size exclusion chromatography (SEC) could adequately separate cathepsin D from aflibercept (FIG. 25). In particular, it was observed that a parameter in developing modified SEC process was increasing the number of plates for SEC to more than about 1000 plates. For the experiment, plates with 100 cm packing were evaluated (data not shown). In particular, comparing the number of plates for SEC purification, it was observed that the SEC column has an efficiency criterion of >1134 plates.

Using the modified SEC purification, the high concentration DSI lot was purified downstream using SEC. The optimization of the SEC purification showed a reduction in the levels of lower molecular weight HCPs, including cathepsin D. The levels of cathepsin D observed in all three final drug substance (FDS) lots post optimization of the DSI lots were below those levels observed in lots which resulted in HMW and LMW profiles at 6 months stability at 25° C. (as mentioned in Example 10). In addition, stability data up to the 3-month data point at 25° C. for these lots also showed profiles for LMW which further supports cathepsin D clearance following implementation of the changes.

Figure 26:
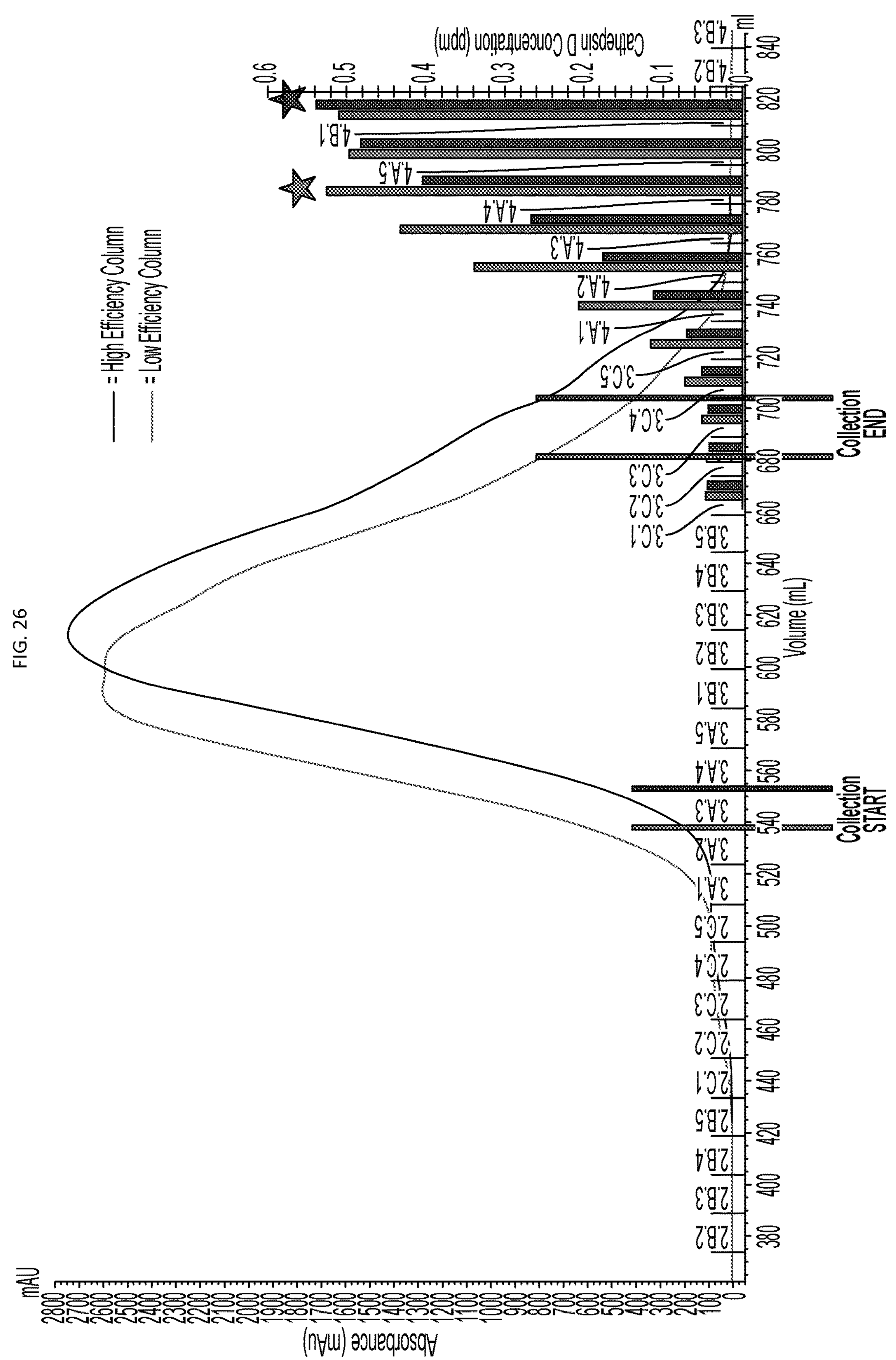
FIG. 26 shows a small-scale SEC run on high (blue, right curve) and low (red, left curve) efficiency columns to confirm shifts in cathepsin D retention time (peak fraction denoted by star and determined by activity assay) and therefore resolution from the VEGF-Trap main peak, according to an exemplary embodiment.
Figure 27A:
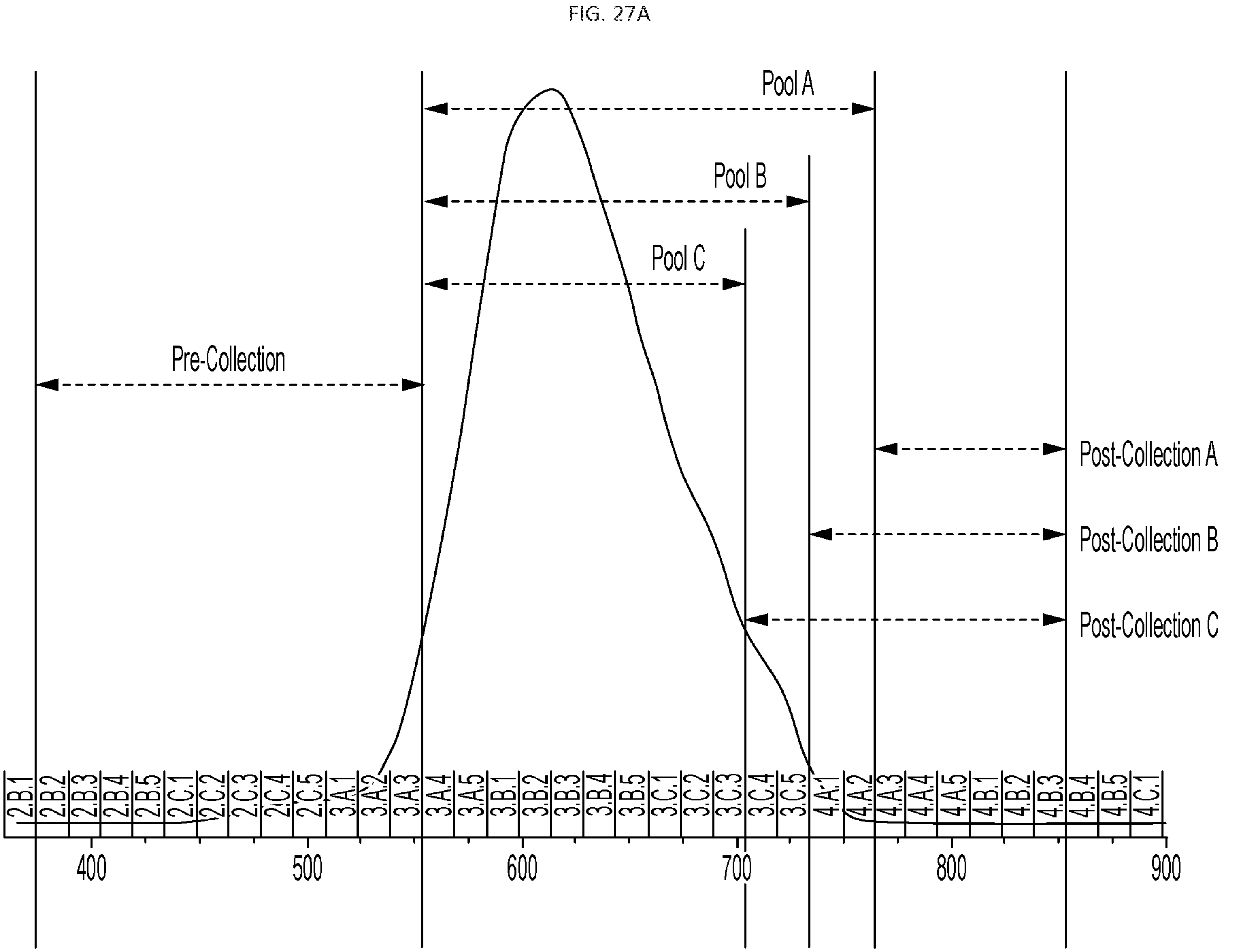
FIG. 27A shows the fractions, which were analyzed for cathepsin D activity, wherein fractions that would be removed from the pool by an earlier collection end, are represented by dashed lines, according to an exemplary embodiment.
Figure 27B:
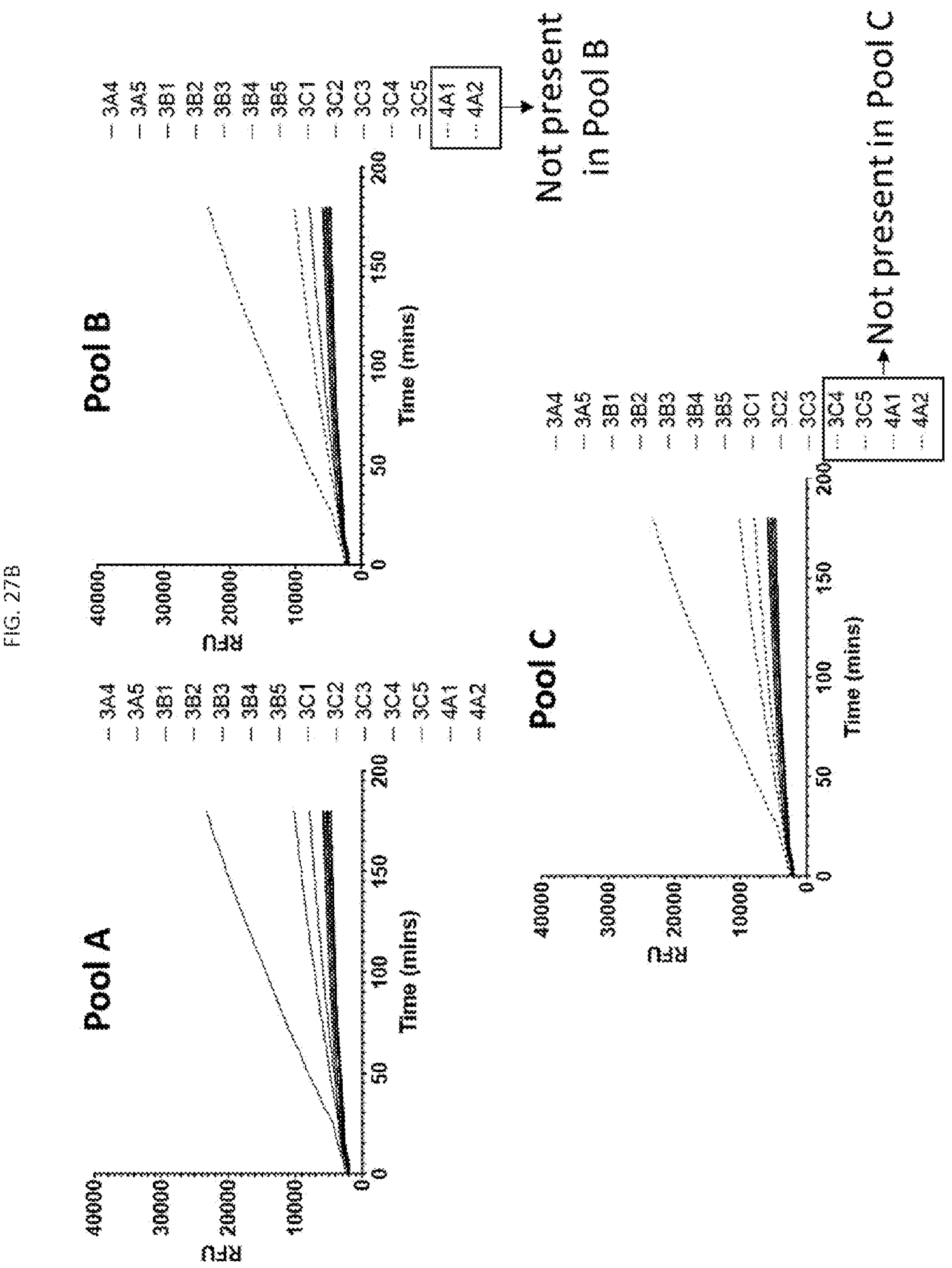
FIG. 27B is a panel of graphs showing cathepsin D activity in the fractions shown in FIG. 27A.

In order to confirm the findings, higher efficiency SEC columns were evaluated. As shown in FIG. 26, these columns provided a greater aflibercept and cathepsin D resolution. Activity of cathepsin D increases across fractions that overlap with peak end collection criteria of 0.05 AU (FIG. 27), indicating increased cathepsin D levels across those fractions. The fractions marked as “Not present in Pool B/Not present in Pool C” in FIG. 27B are designations relative to all of the fractions (i.e., they are all present in Pool A).

Figure 33B:
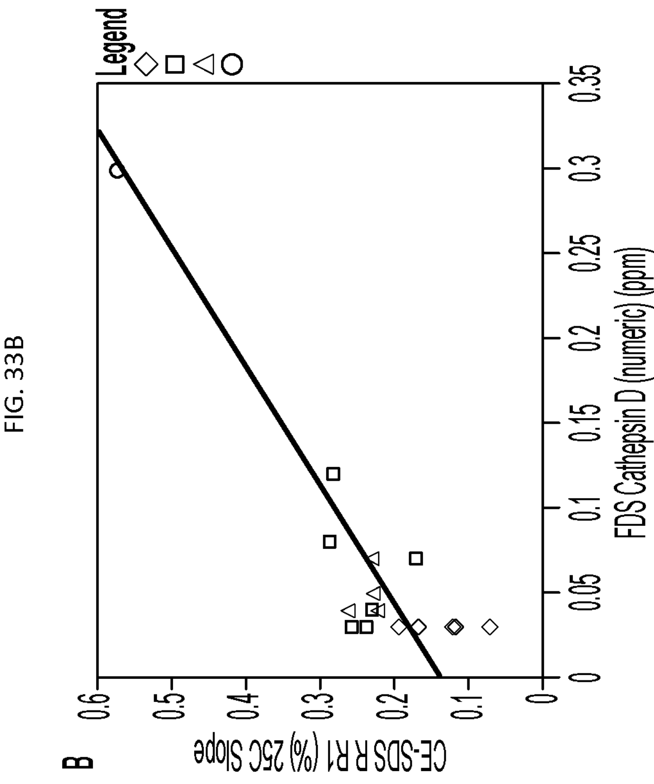
FIG. 33A and FIG. 33B show the Formulated Drug Substance from multiple process areas Pre- and Post-SEC optimization.
Figure 33A:
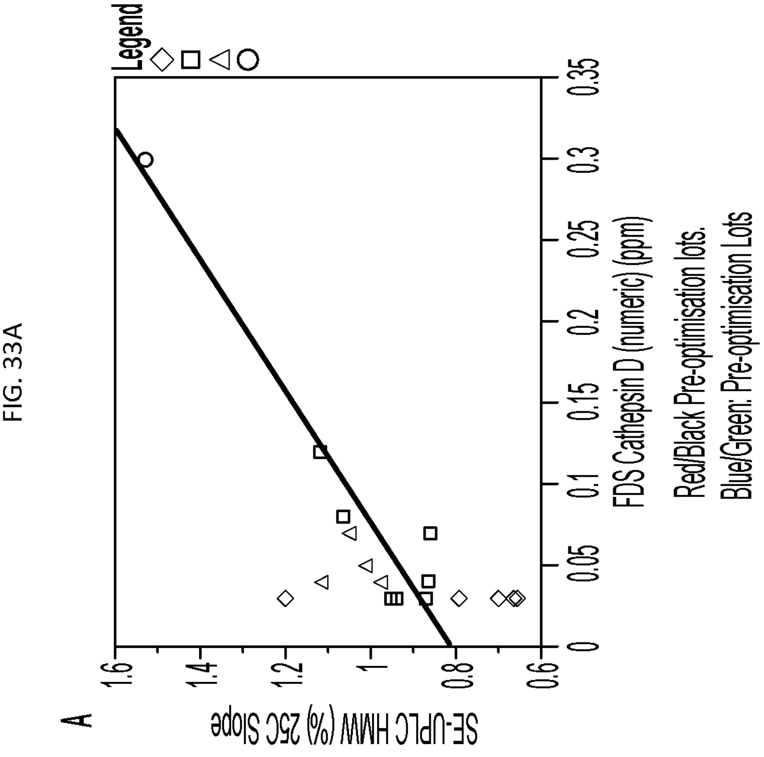
Figure 34:
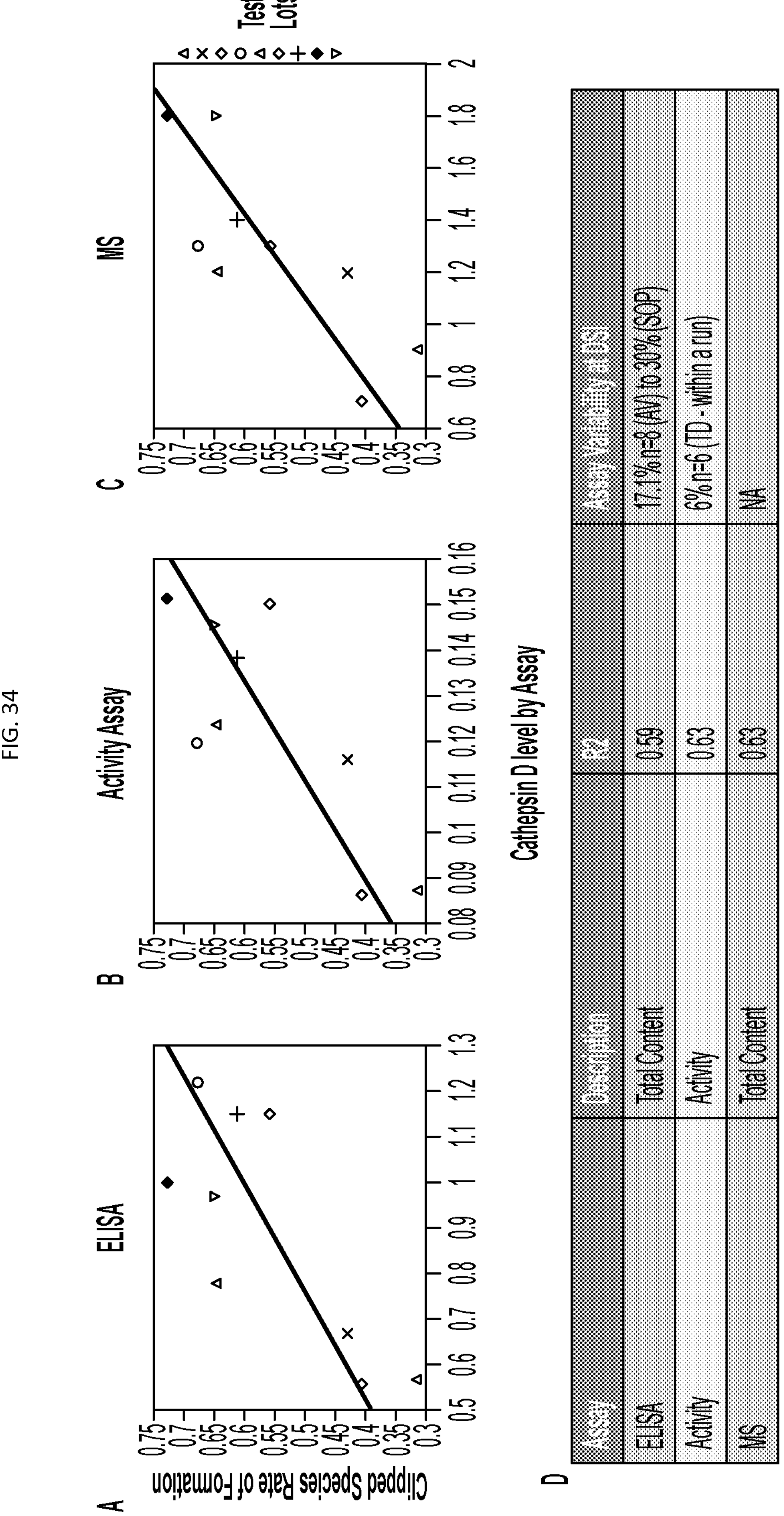
FIG. 34 shows the capability of an ELISA assay, an Activity Assay and LC-MS to correlate cathepsin D concentration to accelerated stability behavior for a given Drug Substance Intermediate. These techniques can also be used to correlate cathepsin D concentration to accelerated stability behavior for a given FDS.

Three lots were processed with the modified purification method and the results show increased clearance and subsequently lower levels of cathepsin D in the final drug substance post the change. An earlier cut in time for the eluting peak was implemented for the SEC step for the higher concentration DSI lots (FIG. 28) resulting in increased clearance and subsequently lower levels of cathepsin D at FDS (FIG. 29). Lastly, the stability data at 25° C. at 3 months for those FDS lots showed LMW levels in line with comparators i.e., FDS obtained from low concentration DSI lots (FIG. 30). Accelerated stability (25'C for 6 months) was investigated. The cumulative increase in HMW (FIG. 33A) and R1 (FIG. 33B) was represented over that 6 months by calculation of the slope. This slope was then plotted against the amount of cathepsin D (in ppm by ELISA) and showed a relationship between cathepsin D pre-optimisation (open square and open circle) and post-optimisation (open diamond and open triangle) from several process areas. The cathepsin D mediated NR1 species showed a higher variability pre-optimization as compared to post-optimization. The DSI was analyzed for stability at 25° C. for 6 months. The rate of NR1 species was calculated from T0 to T6 months and plotted against the cathepsin D value obtained by ELISA (FIG. 34A), Activity Assay (FIG. 34B) and Mass Spectrometry (FIG. 34C). The data show that irrespective of the method of analysis, the stability can be predicted based on the cathepsin D level (FIG. 34D).

Figure 35A:
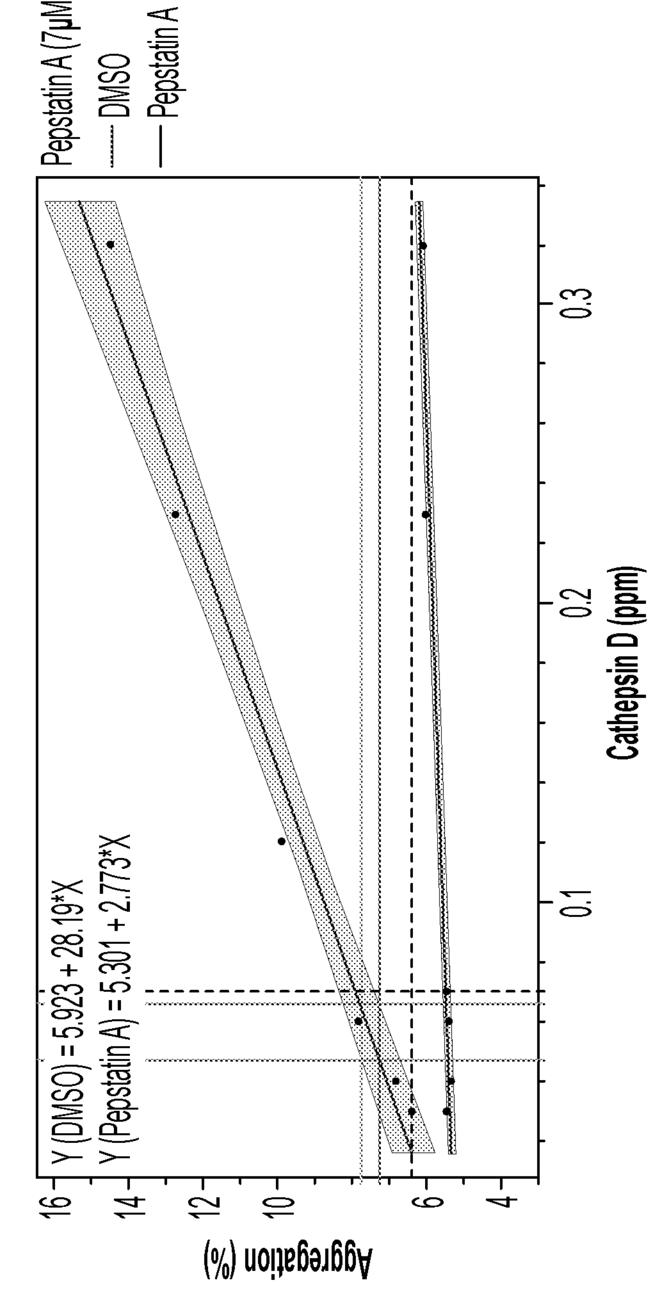
FIG. 35A illustrates a chart showing development stability at FDS and demonstrates that the aggregate is linked to clipped species formation. The DMSO line is FDS with various concentrations of Cathepsin D and the Total HMW at 6 months. The Pepstatin A line is the same material with the Cathepsin D inhibitor (pepstatin A).
Figures 35B, 36A:
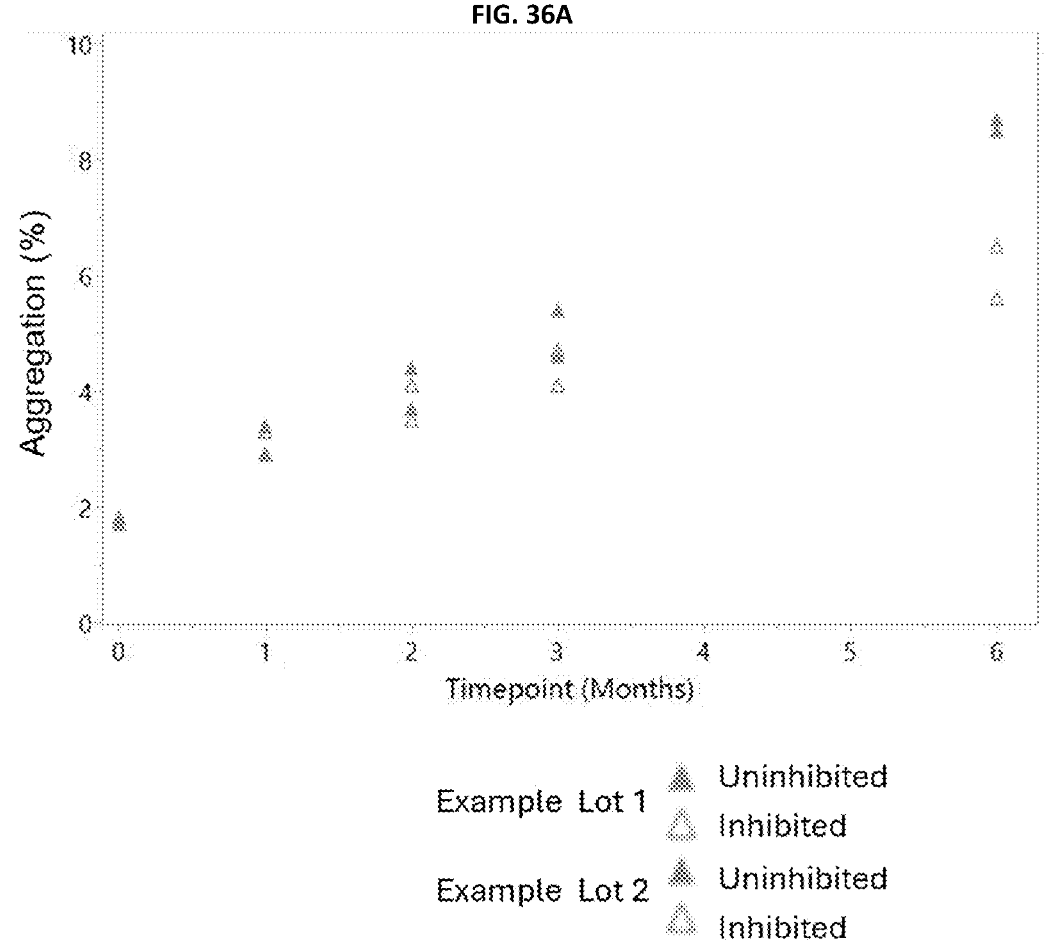
FIG. 35B shows a diagram of blending of pre-optimization and post-optimization cathepsin D to correlate cathepsin D concentration to aflibercept stability.
FIG. 36A and FIG. 36B show development stability at FDS demonstrates that the aggregate is linked to clipped species formation. Closed triangles represent two DSI lots with cathepsin D present. Open triangles represent the same two DSI lots with cathepsin D present but inhibited by the inhibitor (pepstatin A) LHS: Aggregation RHS: NR1 (clipped species).

Formulated Drug Substance with high (pre-optimization) and low (post-optimization) cathepsin D were blended to achieve various levels of cathD (FIG. 35B). These mixtures were prepared to compare to cathepsin D levels below, at, and above the highest known levels that were observed post-optimized IVT and had acceptable stability performance. The blended material was put on 25° C. stability observation in both the presence and absence of the inhibitor pepstatin A (FIG. 35A). HMW formation was tracked (SE-UPLC); FIG. 35A shows the total HMW aggregate formation was associated with each blend (i.e. various levels of cathepsin D) and demonstrates that cathepsin D activity is responsible for HMW formation (blue shading) and that the presence of cathepsin D does not induce HMW formation (red=inhibited with pepstatin A).

Figure 36B:
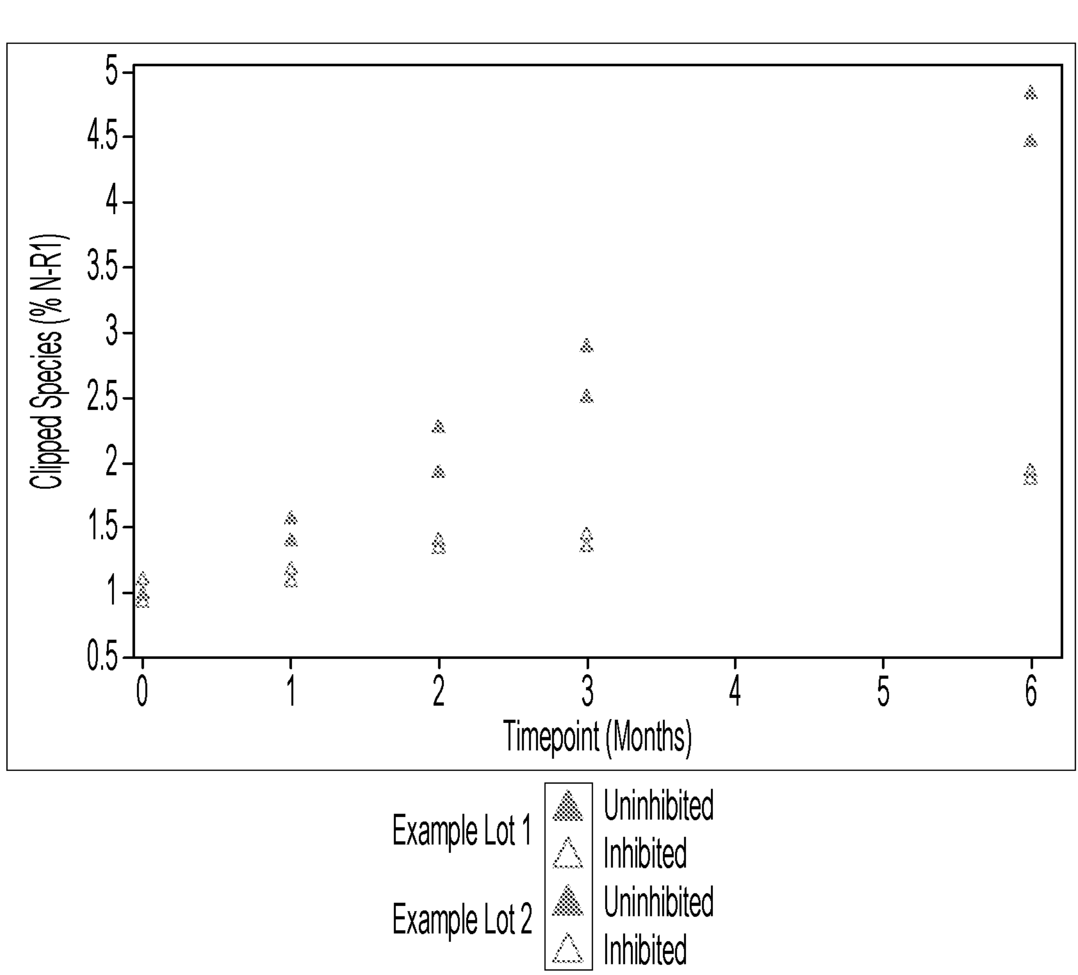

The Drug Substance Intermediate from two Lots was placed on stability observation at 25° C. in the presence (open triangle) and absence (closed triangle) of the inhibitor pepstatin A for 6 months (FIG. 36). The data shows the HMW (FIG. 36A; SE-UPLC) and NR1 species (FIG. 36B; CE-SDS) were associated with the activity of cathepsin D and not attributed to its presence alone. Pepstatin A inhibitor presence showed reduced NR1 formation and reduced HMW formation (FIG. 36).

FIG. 37 shows that FDS from MFG process had high and low cathepsin D levels. Samples were placed on 25° C. and 5° C. stability observation in the presence and absence of cathepsin D inhibitor. HMW formation was analyzed by SE-UPLC and NR1 formation was analyzed by CE-SDS.

Figures 37A, 37B, 37C, 37D:
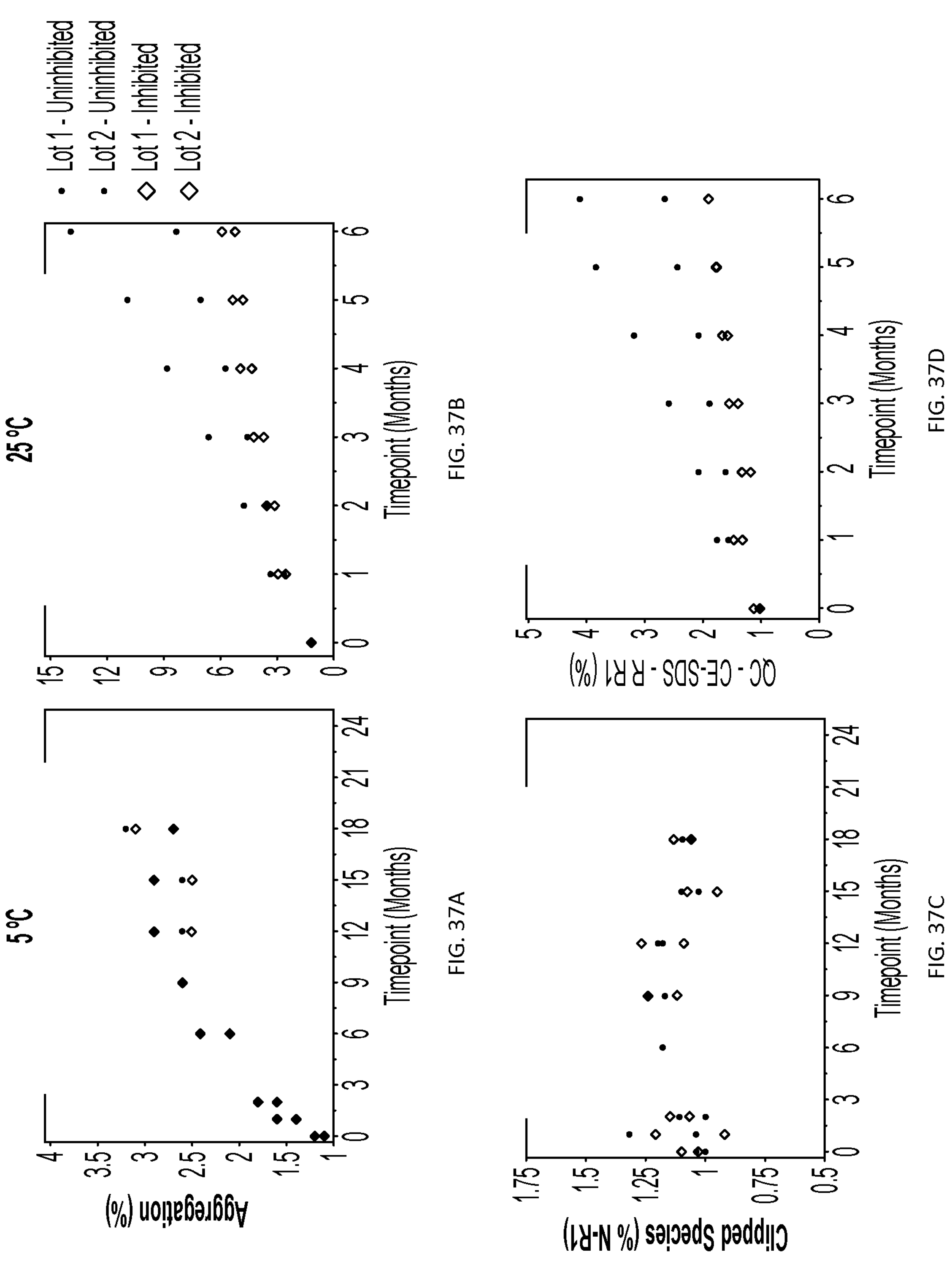
FIG. 37A, FIG. 37B, FIG. 37C, and FIG. 37D show stability pre-optimization. Higher levels of Cathepsin D (red) have minimal impact on NR1 formation at 5° C. Higher levels of Cathepsin D (red) impact observed at 25° C. Presence of inhibitor (open symbols) prevents effect of Cathepsin D at 25° C. Presence of inhibitor (open symbols) at 5° C. shows that activity (not just presence) of Cathepsin D is important for stability behavior.

The data shows that preoptimized FDS processing in cathepsin D presence causes NR1 formation and HMW formation and this could be attributed to cathepsin D activity (FIGS. 37B and 37D; 25° C. Condition). The analysis was also performed at 5° C. to show that the presence of inactive cathepsin D (via inhibitor and or low temperature) resulted in no formation of NR1 for up to 18 months (FIGS. 37A and 37C).

Figure 28:
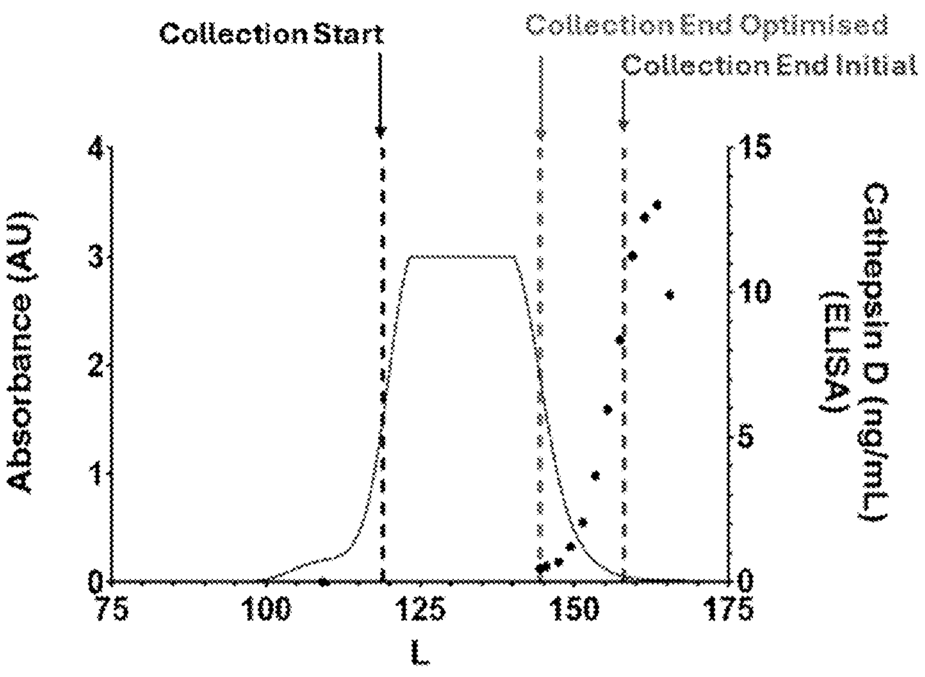
FIG. 28 displays a peak associated with a mixture aflibercept and cathepsin D eluting from an SEC column and earlier collection end (cut) implemented during the SEC purification step to reduce cathepsin D levels, according to an exemplary embodiment.
Figure 29B:
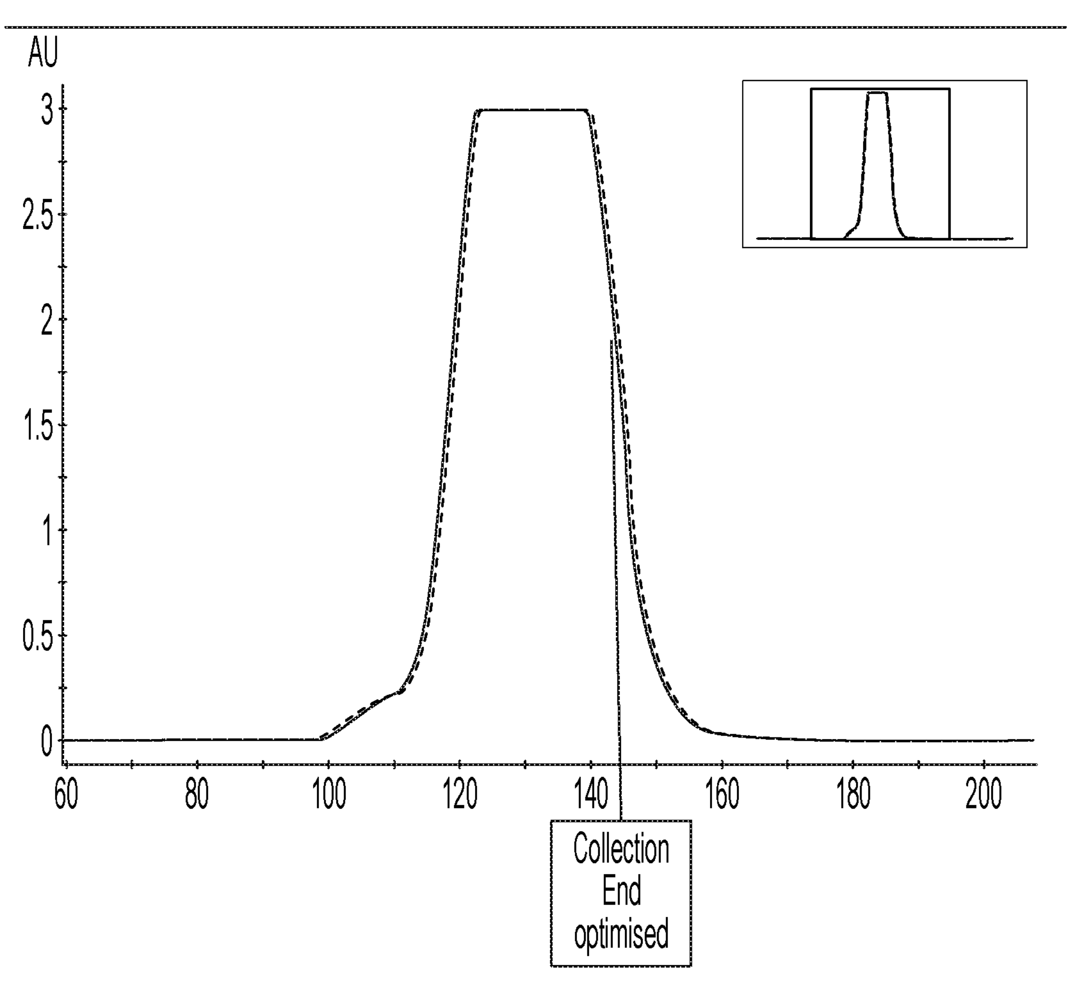
FIG. 29B is a graph of the experiment led earlier cut implemented during the SEC purification step to reduce Cathepsin D levels, according to an exemplary embodiment.
Figure 29C:
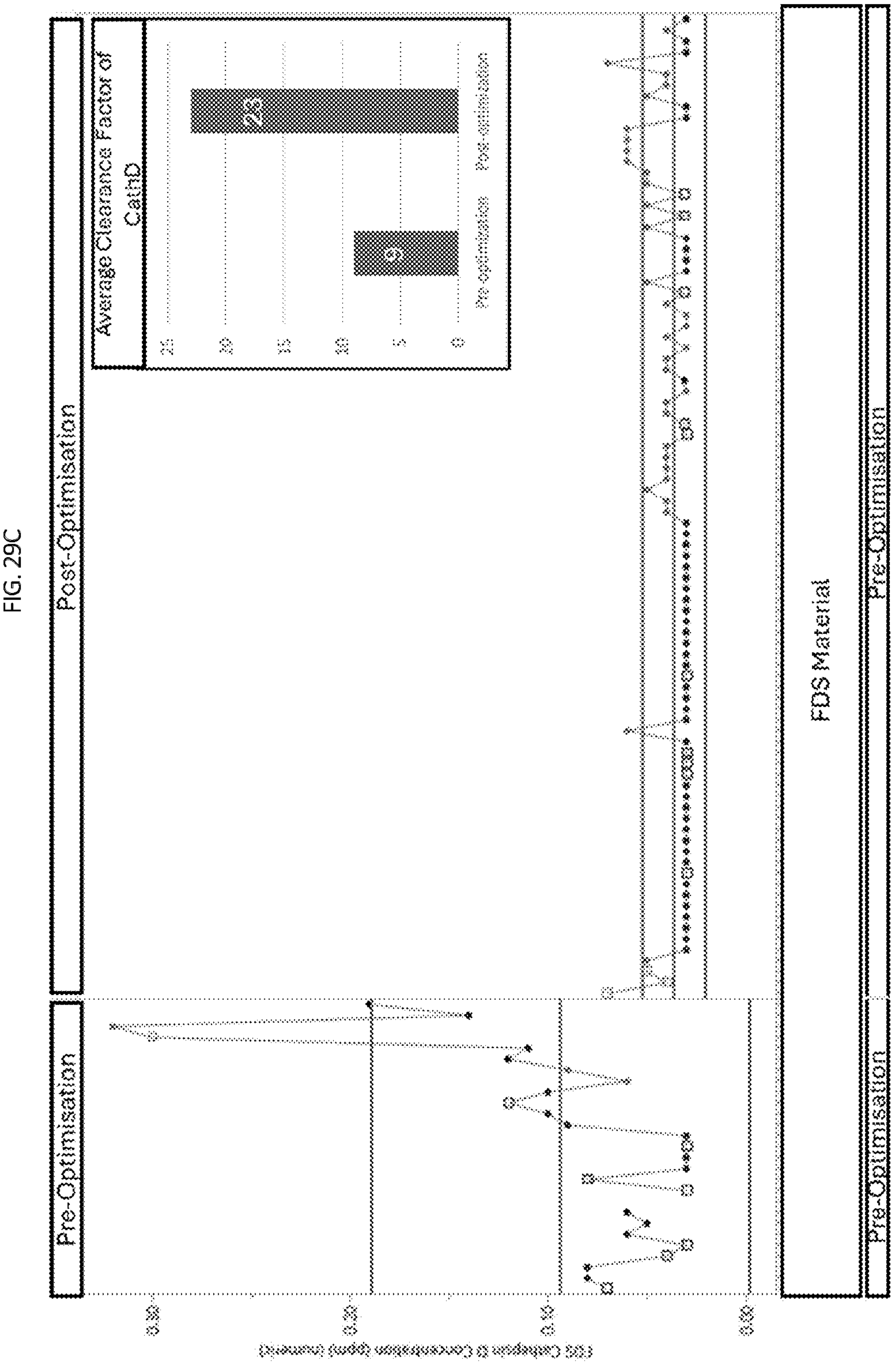
FIG. 29C shows cathepsin D concentration pre- and post-optimization (e.g., an SEC purification step), according to an exemplary embodiment.

As shown in FIG. 26 and FIG. 28, although a certain amount of cathepsin D can be separated from the aflibercept, a certain amount of cathepsin D co-elutes with the aflibercept. FIG. 26 shows an analysis of various fractions of eluting aflibercept and the amount of cathepsin D in the fractions. Even with the higher efficiency column, cathepsin D co-elutes with aflibercept. The amount of cathepsin D is shown on the right axis and it can be seen that certain amounts are co-eluting at the same time as aflibercept on the bottom axis. To further reduce the amount of cathepsin D collected in a sample, the collection criteria for collecting aflibercept eluting from the SEC column was changed. As shown in FIG. 28, aflibercept can be purified from a DSI by truncating the collection of aflibercept eluting from the SEC column. That is, a first eluate from the SEC column that includes the aflibercept and low amount of the cathepsin D, e.g., no more than 0.1 ppm. (collection end earlier in time. i.e. optimized collection end) while excluding a second eluate that includes the aflibercept and significantly more cathepsin D (e.g., between Collection End Optimized and Collection end initial). This process reduces the yield of collected aflibercept, but reduced the amount of cathepsin D in the collected product.

Example 13. Polysorbate 20 for Cathepsin D Removal

Figure 31:
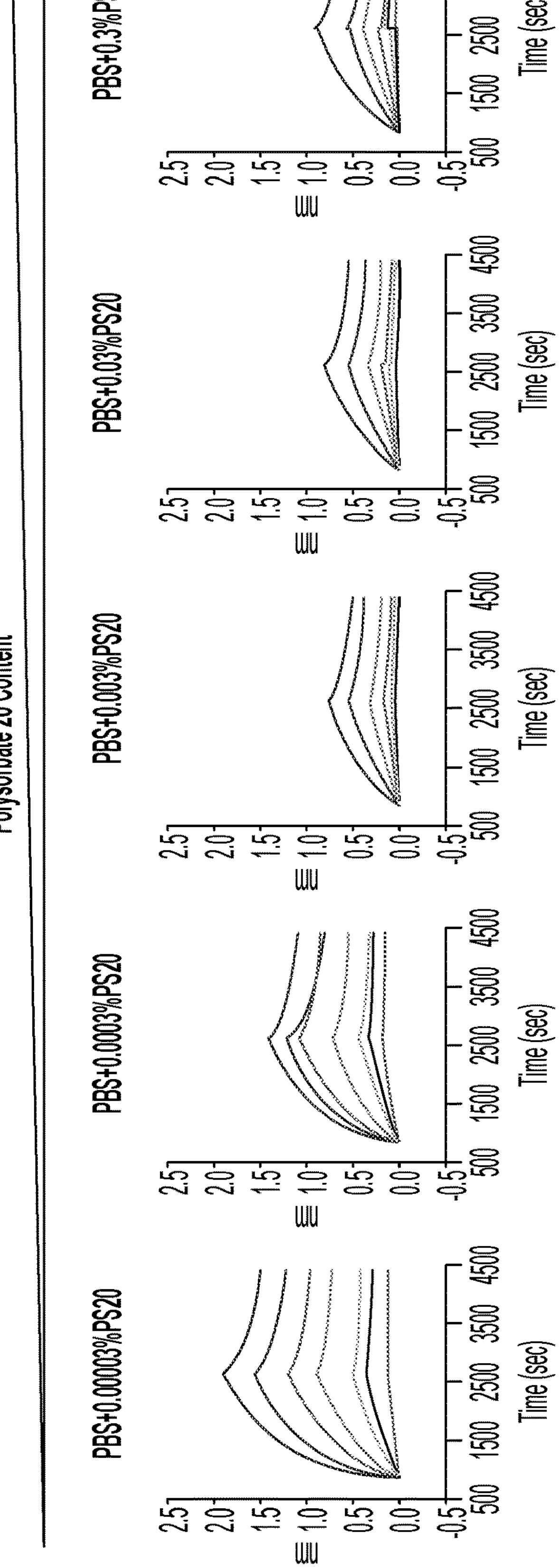
FIG. 31 are Octet HTX sensorgrams of VEGF-Trap and cathepsin D binding in the presence of increasing polysorbate 20 (PS20) buffer concentration, wherein cathepsin D was immobilized to the biosensor, while VEGF-Trap was the analyte (A), according to an exemplary embodiment.
Figure 32:
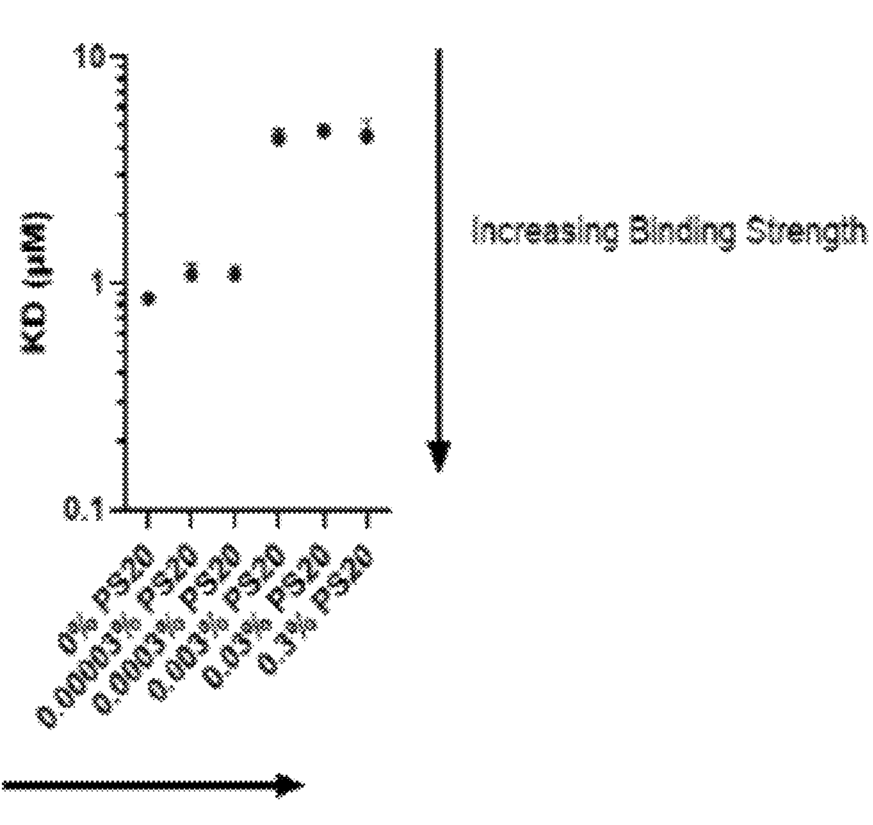
FIG. 32 illustrates a chart showing reduction in steady state binding affinity of VEGF-Trap and cathepsin D binding observed in the presence of PS20, particularly at >0.0003%, according to an exemplary embodiment.

Since cathepsin D can "piggy back" onto aflibercept during purification of aflibercept, in order to reduce the interactions, use of surfactants was implemented. For example, addition of polysorbate 20 (PS20) showed reduction in aflibercept-cathepsin D interaction (FIG. 31) during formulation in the DSI process, providing an opportunity for removal of free cathepsin D during downstream purification, for example the SEC purification discussed above. It was found that at a process relevant concentration of about 0.003% PS20, the $K_D$ of aflibercept-cathepsin D interaction decreased by about 4-fold (FIG. 32).

The results show increased clearance and subsequently lower levels of cathepsin D at FDS post the change. In addition, stability data at 25° C. at 3 months demonstrates LMW levels in line with FDS obtained from low concentration DSI lots.

What is claimed is:

1. A formulation comprising one or more pharmaceutically acceptable excipients, aflibercept at a concentration of from about 100 mg/mL to about 200 mg/mL and a residual amount of cathepsin D of less than about 1 ppm, wherein the formulation exhibits a reduced level of NR1 species relative to a formulation having greater than 1 ppm cathepsin D.

2. The formulation according to claim 1, wherein the residual amount of the cathepsin D is from 0.03 ppm to 0.5 ppm.

3. The formulation according to claim 1, comprising a surfactant.

4. The formulation according to claim 3, wherein the surfactant is polysorbate 20.

5. The formulation according to claim 1, wherein the formulation has a pH greater than about 5.0.

6. The formulation according to claim 1, comprising a surfactant, and a pH of greater than about 5.5.

7. The formulation according to claim 1, wherein the residual amount of the cathepsin D is less than 0.1 ppm.

8. The formulation according to claim 1, wherein the formulation has truncated aflibercept in an amount between about 0.1% to about 10%.

9. The formulation according to claim 1, wherein the one or more pharmaceutically acceptable excipients comprise water, a sugar, and a surfactant.

10. The formulation according to claim 1, wherein the residual amount of the cathepsin D is less than 0.5 ppm, and wherein the one or more pharmaceutically acceptable excipients comprise water, a sugar, and a surfactant.

11. The formulation according to claim 1, wherein the formulation has a pH of greater than about 5.5; and wherein the one or more pharmaceutically acceptable excipients comprise water, a sugar, and a surfactant.

12. The formulation according to claim 1, wherein the formulation is suitable for administration to a human subject.

13. The formulation according to claim 12, wherein the residual amount of the cathepsin D is less than 0.5 ppm; and wherein the formulation has a pH of greater than about 5.5.

14. A syringe including the formulation set forth in claim 1, wherein the one or more pharmaceutically acceptable excipients comprise water, a sugar, and a surfactant.

15. A formulation suitable for administration to a human subject comprising one or more pharmaceutically acceptable excipients, between about 100 mg/mL and 200 mg/mL of aflibercept, and having less than 1 ppm of cathepsin D; wherein the aflibercept is separated from a mixture having the aflibercept and greater than 1 ppm of cathepsin D; and wherein the formulation exhibits a reduced level of NR1 species relative to a formulation having greater than 1 ppm cathepsin D.

16. The formulation according to claim 15, wherein the formulation has less than 0.5 ppm of the cathepsin D.

17. The formulation according to claim 15, wherein the formulation comprises a surfactant.

18. The formulation according to claim 15, wherein the one or more pharmaceutically acceptable excipients is a buffering agent.

19. The formulation according to claim 15, wherein the formulation is suitable for administration to a human subject by intravitreal injection.

20. A concentrated pool comprising aflibercept at a concentration from about 120 mg/mL to about 200 mg/mL, and an amount of less than about 1 ppm of cathepsin D, wherein the concentrated pool exhibits a reduced level of NR1 species relative to a concentrated pool having greater than 1 ppm cathepsin D.

21. The concentrated pool according to claim 20, wherein the aflibercept is at a concentration from about 130 mg/mL to about 200 mg/mL.

22. The concentrated pool according to claim 20, further comprising an non-ionic surfactant.

23. The concentrated pool according to claim 20, further comprising a polysorbate surfactant.

24. The concentrated pool according to claim 20, further comprising a polysorbate surfactant at a concentration of at least about 0.001%.

25. A composition, comprising aflibercept, a pharmaceutically acceptable excipient, and a residual amount of cathepsin D;

wherein the pharmaceutically acceptable excipient is selected from: water, a buffering agent, sugar, salt, surfactant, amino acid, polyol, chelating agent, emulsifier or a preservative;

wherein an amount of the aflibercept in the composition is from about 100 mg/mL to about 200 mg/mL;

wherein the aflibercept in the composition is harvested from a preparation that has between 0.5 ppm to 100 ppm of cathepsin D;

wherein the residual amount of the cathepsin D in the composition is less than 0.5 ppm; and wherein the composition exhibits a reduced level of NR1 species relative to a composition having greater than 0.5 ppm cathepsin D.

26. The composition according to claim 25, wherein the residual amount of the cathepsin D is less than about 0.3 ppm.

27. The composition according to claim 26, wherein the composition has a pH of greater than about 5.5.

28. The composition according to claim 25, wherein the composition has a pH of greater than about 5.5.

29. The composition according to claim 25, wherein the pharmaceutically acceptable excipient includes a buffering agent.

30. The composition according to claim 25, wherein the pharmaceutically acceptable excipient includes water, a sugar, and a surfactant; and wherein the composition has a pH of greater than about 5.0.

* * * * *